United States Patent
Lin et al.

(10) Patent No.: US 10,460,617 B2
(45) Date of Patent: Oct. 29, 2019

(54) TESTING SYSTEM

(71) Applicant: SHL Group Ltd, Surrey (GB)

(72) Inventors: Yin Lin, Surrey (GB); Kenneth Lahti, Surrey (GB); Dave Bartram, Surrey (GB); Ilke Inceoglu, Surrey (GB)

(73) Assignee: SHL Group Ltd, Thames Ditton (GB)

( * ) Notice: Subject to any disclaimer, the term of this patent is extended or adjusted under 35 U.S.C. 154(b) by 23 days.

(21) Appl. No.: 14/395,032

(22) PCT Filed: Apr. 16, 2013

(86) PCT No.: PCT/GB2013/000170
§ 371 (c)(1),
(2) Date: Oct. 16, 2014

(87) PCT Pub. No.: WO2013/156746
PCT Pub. Date: Oct. 24, 2013

(65) Prior Publication Data
US 2015/0072332 A1    Mar. 12, 2015

(30) Foreign Application Priority Data

Apr. 16, 2012 (GB) .................................. 1206728.6
Apr. 25, 2012 (GB) .................................. 1207285.6

(51) Int. Cl.
| | |
|---|---|
| G09B 7/00 | (2006.01) |
| G06Q 30/02 | (2012.01) |
| G09B 7/02 | (2006.01) |
| A61B 5/00 | (2006.01) |
| A61B 5/16 | (2006.01) |
| G06Q 50/00 | (2012.01) |

(52) U.S. Cl.
CPC .......... *G09B 7/00* (2013.01); *G06Q 30/0202* (2013.01); *G09B 7/02* (2013.01); *A61B 5/00* (2013.01); *A61B 5/167* (2013.01); *G06Q 30/02* (2013.01); *G06Q 50/01* (2013.01)

(58) Field of Classification Search
CPC .... G06Q 50/01; G06Q 30/02; G06Q 30/0202; G09B 7/02; G09B 7/00; A61B 5/167; A61B 5/00
USPC ........................................................ 434/320
See application file for complete search history.

(56) References Cited

U.S. PATENT DOCUMENTS

| | | | | |
|---|---|---|---|---|
| 5,954,516 A * | 9/1999 | Heinberg | ............... | G09B 7/066 434/322 |
| 6,000,945 A * | 12/1999 | Sanchez-Lazer | ........ | G09B 7/02 434/118 |
| 6,260,033 B1* | 7/2001 | Tatsuoka | ........ | G01R 31/318371 434/322 |

(Continued)

OTHER PUBLICATIONS

Anna Brown and Alberto Maydeu-Olivares, "Item Response Modeling of Forced-Choice Questionnaires", May 9, 2011, Educational and Psychological Measurement, epm.sagepub.com, pp. 460-502.*

(Continued)

*Primary Examiner* — Jack Yip
(74) *Attorney, Agent, or Firm* — Fish & Richardson P.C.

(57) ABSTRACT

A testing system includes apparatus and methods of testing a subject according to a forced-choice scheme. The scheme is based on Thurstonian Item-Response Theory and is particularly relevant to personality assessment. The invention provides dynamic test generation and scoring for efficient testing of subjects using unique tests.

19 Claims, 32 Drawing Sheets

(56) References Cited

U.S. PATENT DOCUMENTS

| | | | | |
|---|---|---|---|---|
| 6,288,753 B1* | 9/2001 | DeNicola | G09B 5/06 | 348/14.01 |
| 2002/0045154 A1* | 4/2002 | Wood | G06Q 30/02 | 434/350 |
| 2002/0160347 A1* | 10/2002 | Wallace | G09B 7/06 | 434/322 |
| 2003/0129574 A1* | 7/2003 | Ferriol | G09B 5/00 | 434/362 |
| 2003/0232314 A1* | 12/2003 | Stout | G09B 7/00 | 434/322 |
| 2004/0210661 A1* | 10/2004 | Thompson | G06Q 30/02 | 709/228 |
| 2005/0096973 A1 | 5/2005 | Heyse | | |
| 2006/0014129 A1* | 1/2006 | Coleman | G09B 7/02 | 434/322 |
| 2006/0121432 A1* | 6/2006 | Sun | G09B 7/02 | 434/322 |
| 2010/0035225 A1* | 2/2010 | Kerfoot, III | G09B 7/00 | 434/335 |
| 2012/0002848 A1* | 1/2012 | Hill | A61B 5/164 | 382/118 |
| 2012/0231437 A1* | 9/2012 | Fakhrai | G09B 7/00 | 434/350 |
| 2013/0149681 A1* | 6/2013 | Tinkler | G09B 7/04 | 434/167 |

OTHER PUBLICATIONS

Authorized officer Christiaan Gabriel, International Search Report/Written Opinion in PCT/GB2013/000170 dated Nov. 26, 2013, 8 pages.

European Patent Office, Extended European Search Report issued in EP Application No. EP 17194838.3 dated Feb. 9, 2018, 7 pages.

Office Action issued in European Application No. 13724308.5 dated Mar. 11, 2016, 4 pages.

* cited by examiner

Choose which of the two statements below is more true of you.

| a ○ | When I do something wrong, I will admit it. |
|---|---|
| b ○ | I try to keep my promises, but sometimes I am unable to. |

FIG. 1(a)

|  | More | Least |
|---|---|---|
| I enjoy the companionship of others | ○ | ○ |
| I try out new activities | ○ | ✓ |
| I look to the future | ✓ | ○ |

FIG. 1(b)

|  | Most like me | Least like me |
|---|---|---|
| I am exceptionally thorough with my work | ○ | ○ |
| I always feel unprepared for change | ○ | ○ |
| I am more comfortable to let other take charge | ○ | ○ |
| I am the one team members turn to for support | ○ | ○ |

FIG. 1(c)

| Scale ID | Scale name | Scale direction | Number of items |
|---|---|---|---|
| 1 | Persuasive | 1 | 10 |
| 2 | Controlling | -1 | 9 |
| 3 | Outspoken | 1 | 10 |
| 4 | Independent minded | 1 | 9 |
| 5 | Outgoing | 1 | 9 |
| 6 | Affiliative | 1 | 10 |
| 7 | Socially confident | 1 | 9 |
| 8 | Modest | 1 | 10 |
| 9 | Democratic | 1 | 9 |
| 10 | Caring | 1 | 10 |
| 11 | Data rational | 1 | 10 |
| 12 | Evaluative | 1 | 9 |
| 13 | Behavioural | 1 | 10 |
| 14 | Conventional | 1 | 10 |
| 15 | Conceptual | 1 | 10 |
| 16 | Innovative | 1 | 10 |
| 17 | Variety seeking | 1 | 9 |
| 18 | Adaptable | 1 | 10 |
| 19 | Forward thinking | 1 | 10 |
| 20 | Detail conscious | 1 | 10 |
| 21 | Conscientious | 1 | 10 |
| 22 | Rule following | 1 | 10 |
| 23 | Relaxed | 1 | 10 |
| 24 | Worrying | -1 | 9 |
| 25 | Tough minded | 1 | 9 |
| 26 | Optimistic | 1 | 10 |
| 27 | Trusting | 1 | 10 |
| 28 | Emotionally controlled | 1 | 10 |
| 29 | Vigorous | 1 | 10 |
| 30 | Competitive | 1 | 10 |
| 31 | Achieving | 1 | 10 |
| 32 | Decisive | 1 | 10 |

FIG. 3

| Item ID | Scale ID | Item parameters | | Item text | Selection count | Last 2 triplets | Selection allowed |
|---|---|---|---|---|---|---|---|
| | | Loading | Threshold | Social desirability | | | |
| i1 | 10 | 0.599 | 0.732 | 0.732 | I like helping people | 0 | 0 | 1 |
| i2 | 30 | 1.166 | -0.575 | -0.575 | I enjoy competitive activities | 0 | 0 | 1 |
| i3 | 26 | 0.702 | -0.157 | -0.157 | I view things positively | 0 | 0 | 1 |
| i4 | 6 | 1.334 | 0.742 | 0.742 | I enjoy the companionship of others | 0 | 0 | 1 |
| i5 | 1 | 1.291 | -0.980 | -0.980 | I find negotiation easy | 1 | 0 | 0 |
| i6 | 19 | 1.360 | 0.238 | 0.238 | I look to the future | 0 | 0 | 1 |
| i7 | 15 | 0.571 | 0.422 | 0.422 | I like to discuss abstract concepts | 1 | 0 | 0 |
| i8 | 11 | 0.860 | -0.180 | -0.180 | I enjoy interpreting statistics | 0 | 0 | 0 |
| i9 | 27 | 0.857 | -0.242 | -0.242 | I feel that people are honest | 0 | 0 | 1 |
| i10 | 23 | 0.809 | -0.087 | -0.087 | I feel free from pressure | 0 | 0 | 1 |
| i11 | 18 | 0.891 | -0.080 | -0.080 | I behave differently to fit in with other people | 0 | 0 | 1 |
| i12 | 8 | 0.455 | 0.167 | 0.167 | I avoid telling people when I succeed | 0 | 0 | 1 |
| i13 | 25 | 1.053 | -0.002 | -0.002 | I am difficult to offend | 0 | 0 | 1 |
| i14 | 26 | 0.500 | 0.607 | 0.607 | I expect things to turn out well | 0 | 0 | 1 |
| i15 | 29 | 1.052 | -0.605 | -0.605 | I like to have a lot of work | 0 | 0 | 1 |
| i16 | 20 | 1.270 | 0.070 | 0.070 | I keep paperwork in order | 0 | 0 | 1 |
| i17 | 4 | 0.845 | -0.080 | -0.080 | I insist on doing things my own way | 1 | 0 | 0 |
| i18 | 24 | 0.515 | 0.010 | 0.010 | I get worried before a big meeting | 0 | 0 | 1 |
| i19 | 9 | 0.650 | -0.169 | -0.169 | I frequently consult others | 0 | 0 | 1 |
| i20 | 29 | 0.668 | 0.084 | 0.084 | I keep myself busy | 0 | 0 | 1 |
| i21 | 31 | 0.749 | 0.085 | 0.085 | I achieve difficult targets | 0 | 0 | 1 |
| i22 | 21 | 0.722 | 0.526 | 0.526 | I persist with tasks until completed | 0 | 0 | 1 |
| i23 | 28 | 0.669 | -0.160 | -0.160 | I tend to conceal how I feel | 0 | 0 | 1 |
| i24 | 31 | 0.886 | -0.366 | -0.366 | I set myself demanding targets | 0 | 0 | 1 |
| i25 | 32 | 1.213 | -0.367 | -0.367 | I quickly reach a decision | 0 | 0 | 1 |
| i26 | 7 | 1.282 | -0.273 | -0.273 | I feel at ease with new people | 0 | 0 | 1 |
| i27 | 22 | 1.076 | 0.640 | 0.640 | I take care to follow rules | 0 | 0 | 1 |
| i28 | 18 | 1.439 | -0.150 | -0.150 | I change how I act to fit my surroundings | 0 | 0 | 1 |
| i29 | 27 | 1.073 | -0.133 | -0.133 | I have faith in other people | 0 | 0 | 1 |

FIG. 4

| 800 Scales selected | | | 820 | 822 | 814 Item usage constraint | 804 | 816 | 806 Information constraint | 808 | 810 | 802 812 | 818 |
|---|---|---|---|---|---|---|---|---|---|---|---|---|
| Selected counts | Scale ID | Current theta [θ] | Scale selectable status [STATUS] | Scale completion status | # items administered (including repeat) [NADMIN] | # items available [NAVAIL] | Rank (ascending item administered) | Target info [TI] | Prior info | Test info | Info deficiency | Rank (descending required info) |
| 1 | 1 | -0.442 | 0 | TRUE | 10 | 10 | 6 | 9.183 | 1.468 | 3.018 | 4.696 | 4 |
| 2 | 2 | -1.390 | 1 | FALSE | 9 | 9 | 2 | 9.183 | 1.652 | 2.456 | 5.075 | 3 |
| 3 | 3 | -1.025 | 0 | TRUE | 10 | 10 | 6 | 9.183 | 1.605 | 3.992 | 3.586 | 7 |
| 4 | 4 | -0.211 | 1 | FALSE | 9 | 9 | 2 | 9.183 | 1.295 | 3.446 | 4.442 | 5 |
| 5 | 5 | -0.206 | 1 | FALSE | 4 | 9 | 1 | 9.183 | 1.404 | 5.452 | 2.326 | 10 |
| 6 | 11 | 1.191 | 1 | FALSE | 9 | 10 | 2 | 9.183 | 1.233 | 5.524 | 2.426 | 9 |
| 7 | 12 | 0.268 | 1 | FALSE | 9 | 9 | 2 | 9.183 | 1.692 | 3.525 | 3.965 | 6 |
| 8 | 13 | -1.123 | 0 | TRUE | 10 | 10 | 6 | 9.183 | 1.457 | 1.720 | 6.006 | 1 |
| 9 | 14 | 0.964 | 0 | TRUE | 10 | 10 | 6 | 9.183 | 1.290 | 4.492 | 3.401 | 8 |
| 10 | 15 | 1.375 | 0 | TRUE | 10 | 10 | 6 | 9.183 | 1.625 | 1.7888 | 5.770 | 2 |
| 11 | | | | | | | | | | | | |
| 12 | | | | | | | | | | | | |
| 13 | | | | | | | | | | | | |
| 14 | | | | | | | | | | | | |
| 15 | | | | | | | | | | | | |

FIG. 10

Triplet number:

30

| Statement ID | Statement text | Most | Least |
|---|---|---|---|
| 1 | I favour well proven methods | 1 | |
| 2 | I speak up when people are wrong | | 1 |
| 3 | I like to work with numbers | | |

| Check | Code |
|---|---|
| 1 | 2 |
| 1 | 0 |
| 1 | 1 |
| 1 | |

*FIG. 17*

| Triplet responses | | | | | Convert into pairs | |
|---|---|---|---|---|---|---|
| Triplet | Items | Scale | Loading | Threshold | Response | Pairs 1_2 | Response |
| 1 | i197 | 11 | 1.611 | -0.210 | 2 | i197_i244 | 1 |
| 1 | i244 | 14 | 0.500 | 0.007 | 1 | i197_i194 | 1 |
| 1 | i194 | 4 | 0.631 | -0.126 | 0 | i244_i194 | 1 |
| 2 | i211 | 5 | 1.683 | -0.142 | 2 | i211_i95 | 1 |
| 2 | i95 | 13 | 0.638 | 0.305 | 0 | i211_i5 | 1 |
| 2 | i5 | 1 | 1.291 | -0.980 | 1 | i95_i5 | 0 |
| 3 | i142 | 13 | 0.625 | -0.033 | 1 | i142_i138 | 1 |
| 3 | i138 | 3 | 0.802 | -0.120 | 0 | i142_i282 | 0 |
| 3 | i282 | 15 | 0.692 | -0.087 | 2 | i138_i282 | 0 |
| 4 | i196 | 2 | 1.673 | -0.287 | 0 | i196_i239 | 0 |
| 4 | i239 | 12 | 0.987 | 0.009 | 2 | i196_i119 | 0 |
| 4 | i119 | 13 | 1.258 | 0.494 | 1 | i239_i119 | 1 |
| 5 | i265 | 4 | 0.495 | 0.353 | 0 | i265_i221 | 0 |
| 5 | i221 | 14 | 0.500 | 0.167 | 2 | i265_i88 | 0 |
| 5 | i88 | 12 | 0.807 | 0.056 | 1 | i221_i88 | 1 |
| 6 | i193 | 15 | 0.891 | -0.148 | 2 | i193_i83 | 1 |
| 6 | i83 | 1 | 0.535 | -0.243 | 0 | i193_i17 | 1 |
| 6 | i17 | 4 | 0.845 | -0.080 | 1 | i83_i17 | 0 |
| 7 | i181 | 3 | 0.840 | 0.282 | 0 | i181_i165 | 0 |
| 7 | i165 | 1 | 1.037 | -0.371 | 1 | i181_i297 | 0 |
| 7 | i297 | 14 | 0.751 | 0.269 | 2 | i165_i297 | 0 |
| 8 | i7 | 15 | 0.571 | 0.422 | 2 | i7_i274 | 1 |
| 8 | i274 | 13 | 1.105 | 0.002 | 0 | i7_i117 | 1 |
| 8 | i117 | 12 | 0.791 | 0.309 | 1 | i274_i117 | 0 |
| 9 | i118 | 15 | 0.941 | -0.325 | 2 | i118_i69 | 1 |
| 9 | i69 | 4 | 0.741 | -0.295 | 1 | i118_i162 | 1 |
| 9 | i162 | 12 | 0.912 | -0.060 | 0 | i69_i162 | 1 |
| 10 | i233 | 3 | 1.078 | -0.061 | 0 | i233_i185 | 0 |
| 10 | i185 | 4 | 0.808 | 0.247 | 1 | i233_i90 | 0 |
| 10 | i90 | 15 | 0.530 | -0.354 | 2 | i185_i90 | 0 |
| 11 | i140 | 15 | 0.633 | -0.360 | 2 | i140_i105 | 1 |
| 11 | i105 | 2 | 1.043 | 0.003 | 0 | i140_i60 | 1 |
| 11 | i60 | 13 | 0.644 | 0.347 | 1 | i105_i60 | 0 |
| 12 | i304 | 15 | 0.686 | 0.252 | 2 | i304_i209 | 1 |
| 12 | i209 | 3 | 0.806 | -0.032 | 0 | i304_i36 | 1 |
| 12 | i36 | 14 | 0.611 | 0.565 | 1 | i209_i36 | 0 |
| 13 | i238 | 4 | 0.985 | -0.130 | 1 | i238_i246 | 1 |

FIG. 18

| Optimisation | | | | Scale ID | Theta |
|---|---|---|---|---|---|
| Correlation | Composite | Probability (response) | Loglikelihood | | |
| -0.119 | 1.219 | 0.889 | 0.118 | 1 | -0.442 |
| 0.076 | 1.968 | 0.975 | 0.025 | 2 | -1.390 |
| -0.275 | 0.749 | 0.773 | 0.257 | 3 | -1.025 |
| 0.177 | -0.077 | 0.469 | 0.756 | 4 | -0.244 |
| 0.385 | 1.062 | 0.856 | 0.156 | 5 | -0.206 |
| 0.224 | 1.138 | 0.127 | 2.060 | 11 | 1.191 |
| 0.091 | 0.207 | 0.582 | 0.541 | 12 | 0.268 |
| 0.482 | -1.599 | 0.945 | 0.056 | 13 | -1.123 |
| 0.191 | -1.807 | 0.965 | 0.036 | 14 | 0.964 |
| 0.414 | -2.886 | 0.998 | 0.002 | 15 | 1.375 |
| 0.236 | -1.693 | 0.955 | 0.046 | | 0.000 |
| 0.376 | 1.192 | 0.883 | 0.124 | | 0.000 |
| -0.275 | -0.400 | 0.656 | 0.422 | | 0.000 |
| 0.271 | -0.024 | 0.510 | 0.674 | | 0.000 |
| -0.215 | 0.376 | 0.647 | 0.436 | | 0.000 |
| 0.268 | 1.556 | 0.940 | 0.062 | | 0.000 |
| 0.171 | 1.335 | 0.909 | 0.095 | | 0.000 |
| 0.173 | -0.221 | 0.587 | 0.532 | | 0.000 |
| 0.295 | 0.250 | 0.401 | 0.913 | | 0.000 |
| -0.192 | -1.572 | 0.942 | 0.060 | | 0.000 |
| -0.280 | -1.822 | 0.966 | 0.035 | | 0.000 |
| 0.482 | 2.446 | 0.993 | 0.007 | | 0.000 |
| 0.443 | 0.687 | 0.754 | 0.283 | | 0.000 |
| 0.376 | -1.760 | 0.961 | 0.040 | | 0.000 |
| 0.171 | 1.421 | 0.922 | 0.081 | | 0.000 |
| 0.443 | 0.784 | 0.784 | 0.244 | | 0.000 |
| 0.271 | -0.636 | 0.262 | 1.338 | | 0.000 |
| 0.407 | -1.242 | 0.893 | 0.113 | | 0.000 |
| 0.191 | -1.540 | 0.938 | 0.064 | | 0.000 |
| 0.171 | -0.298 | 0.617 | 0.483 | | 0.000 |
| 0.276 | 1.954 | 0.975 | 0.026 | | 0.000 |
| 0.482 | 0.886 | 0.812 | 0.208 | | 0.000 |
| 0.236 | -1.068 | 0.857 | 0.154 | | 0.000 |
| 0.191 | 2.053 | 0.980 | 0.020 | | 0.000 |
| -0.371 | 0.041 | 0.517 | 0.661 | | 0.000 |
| -0.192 | -2.012 | 0.978 | 0.022 | | 0.000 |
| 0.076 | -0.083 | 0.467 | 0.71 | | 0.000 |

*FIG. 18* Cont'd

Report

| Test generation log | | | | |
|---|---|---|---|---|
| | Instrument and responses | | | |
| | Triplet ID | Item ID | Item text | Candidate responses |
| Test generator called: 16/03/2012 16:36:37 | 1 | i197 | I enjoy numerical problem solving | 2 |
| Method: CAT (V1.0) | 1 | i244 | I like established methods | 1 |
| Maximum test length (triplets) [Mmax]: 40 | 1 | i194 | I follow my own approach despite others' | 0 |
| Maximum number of items per scale [Nmax]: 10 | 2 | i211 | I am outgoing in behaviour | 2 |
| Maximum number of times an item can be used [Umax]: 1 | 2 | i95 | I think about people's behaviour | 0 |
| Maximum social desirability difference [Dmax]: 1.5 | 2 | i5 | I find negotiation easy | 1 |
| Maximum absolute scale correlation [Cmax]: 0.5 | 3 | i142 | I consider what motivates people | 1 |
| Minimum total information from a triplet [Imin]: 0.8 | 3 | i138 | I make my opinions known | 0 |
| Target item keyed direction combination proportions [KO]: 0.6, 0.4, 0, 0 | 3 | i282 | I like theoretical discussions | 2 |
| Optimisation index selection: 3 | 4 | i196 | I like to be in control of the group | 0 |
| Optimisation tolerance factor: 0.8 | 4 | i239 | I recognise weak arguments | 2 |
| Test generation... | 4 | i119 | I enjoy trying to understand people | 1 |
| Test generation terminates: 16/03/2012 16:46:47 | 5 | i265 | I need to feel free to do what I want | 0 |
| Loop count: 31 | 5 | i221 | I take a conventional approach | 2 |
| Triplet count: 30 | 5 | i88 | I critically analyse information | 1 |
| StoppingPermit: True | 6 | i193 | I raise hypothetical arguments | 2 |
| StoppingRule1: False | 6 | i83 | I like to sell an idea | 0 |
| StoppingRule2: False | 6 | i17 | I insist on doing things my own way | 1 |
| StoppingRule3: False | 7 | i181 | I say when I disagree | 0 |
| StoppingRule4: True | 7 | i165 | I am effective in negotiations | 2 |
| | 7 | i297 | I favour established approaches | 1 |

FIG. 19

| Measurement | | | | | | | |
|---|---|---|---|---|---|---|---|
| Scale ID | Scale name | # items administered | Theta estimate | Information estimate | Theta SE | Consistency ratio | Consistency sten |
| 1 | Persuasive | 10 | -0.442 | 4.486 | 0.472 | 0.889 | 9 |
| 2 | Controlling | 9 | -1.390 | 4.108 | 0.493 | | |
| 3 | Outspoken | 10 | -1.025 | 5.597 | 0.423 | | |
| 4 | Indendent minded | 9 | -0.211 | 4.741 | 0.459 | | |
| 5 | Outgoing | 4 | -0.206 | 6.856 | 0.382 | | |
| 11 | Data rational | 9 | 1.191 | 6.757 | 0.385 | | |
| 12 | Evaluative | 9 | 0.268 | 5.217 | 0.438 | | |
| 13 | Behavioural | 10 | -1.123 | 3.177 | 0.561 | | |
| 14 | Conventional | 10 | 0.964 | 5.782 | 0.416 | | |
| 15 | Conceptual | 10 | 1.375 | 3.413 | 0.541 | | |

FIG. 19 Cont'd

TESTING SYSTEM

This invention relates to a testing system including apparatus for and methods of testing a subject according to a forced-choice scheme. In particular, a dynamic forced-choice testing system is described, based on Thurstonian item-response theory. This invention has particular relevance to the personality assessment of individuals, but also has potential applications further afield such as in e-commerce.

Psychometric assessments measure psychological constructs as a means of fulfilling certain business needs such as selecting candidates for a job and predicting job performance. Typically, the subject or candidate is presented with a series of statements or "items", each relating to a personality trait or "scale", and asked to rate how well they consider each item reflects their personality. This allows each response to be scored with the intention of determining where the subject lies on each of the personality scales being tested.

Dominance and Ideal-Point Response Models

The design (and subsequent scoring) of an assessment is a reflection of the way the response of the subject is modelled. Two common models are referred to as "ideal-point" and "dominance" schemes. Each uses different items and requires different mathematical models to describe them.

"Ideal-point" models have items designed to be preferred by subjects with a specific trait level. In such models, an item such as "I keep an averagely tidy sock drawer" would be preferred only by those subjects who score averagely in Conscientiousness.

By contrast, in a "dominance" model, the utility of an item increases (decreases) monotonically for positively (negatively) keyed items. A positively-keyed item (commonly indicated by '+') such as "I keep a tidy sock drawer" would be preferred by subjects who score highly in a trait such as Conscientiousness, whereas, a negatively-keyed item (commonly indicated by '-') such as "My sock drawer is untidy" would be preferred by subjects with low Conscientiousness.

Hence in an "ideal-point" scheme, a subject is more likely to agree with a statement if the statement is close to their perceived trait level on a scale; in a "dominance" scheme, the higher (lower) the trait level of a subject, the more likely the subject is to agree with a positively (negatively) keyed statement for that scale.

There are several drawbacks with "ideal point" schemes, including:
- potential vagueness of terms, requiring a frame of reference
- resulting interpretation issues and variety between candidates
- difficulty in translating into different languages By contrast, "dominance" schemes have certain advantages:
- it is easier to generate clear statements rather than relative ones
- item properties are easier to model and discern 'Liked' and Forced-Choice Test Formats A common format in personality assessment or testing uses single-stimulus responses and a rating or Likert scale, with categories ranging from "strongly disagree" to "strongly agree"; alternatively, numerical rating may be used.

However, there are known issues with single-stimulus testing, usually arising from inherent biases introduced by the test format, such as:

- differences in the interpretation of categories by subjects
- avoidance of extreme categories by subjects
- "halo" effects arising from a generalised view of personality and/or competence
- socially desirable responses In order to reduce these biases, there has therefore been a move in personality assessment to the use of the forced-choice response format. This presents the subject with groups of items (typically described as "blocks", which usually comprise pairs of items, but may comprise triplets or quads) at a time, and requires the subject to make comparative judgements between some or all of the items. Each constituent item may be from the same or different scales.

Scoring

Two main scoring methods are used in practice:
- Classical Test Theory (CTT) scoring—which may be as simple as directly coding the responses and determining a sum score for each scale
- Item-Response Theory (IRT) scoring—which involves to some extent modelling the expected response pattern, and determining the most likely trait level that would result in the response obtained. This score is typically presented as a theta [$\theta$] value on the appropriate scale, with an underlying assumption that for any scale the population is normally distributed about $\theta=0$ with standard deviation 1, the majority lying between −3 and +3.

Although IRT scoring is more complicated than CTT scoring it has certain advantages, such as not being affected by the assumption that the response categories are equally spaced.

Traditional CTT scoring of forced-choice tests is said to produce "ipsative" data, wherein each subject has the same total test score. This can result in the masking of consistent high or low scores by a subject across multiple scales, with subjects typically having the same average score, making comparisons between subjects taking the same test meaningless.

Recent efforts have therefore sought to find suitable IRT frameworks for scoring forced-choice questionnaires.

The Dominance Thurstonian IRT Model

One suggestion for a scoring methodology is based on adapting the work of Thurstone in the 1920s and 1930s, which considered how the result of a comparative judgement relates to the latent utility of the items being compared.

Aspects of such an approach are described in two recent academic papers (the content of which is herein incorporated by reference):

Brown, A (2010). Item Response Modelling of Paired Comparison and Ranking Data. *Multivariate Behavioural Research*, 45:935-974

Brown, A & Maydeu-Olivares, A (2011). Item Response Modelling of Forced-Choice Questionnaires. *Educational and Psychological Measurement*, 71(3) 460-502

The dominance Thurstonian IRT model is developed to capture the response process when a person or subject is faced with a forced-choice question involving several statements (items). The Thurstonian IRT is formulated as follows:

When a person is faced with an item (e.g. 'I am outgoing.'), they can evaluate it and decide how preferable it is. This degree of preferability is defined to be the utility of the item for that person.

How preferable an item i is for a person j is determined by:
- The item content
- The person's trait level on some psychological construct/scale (e.g. a sociability scale)

This relationship is captured by $$t_i = \mu_i + \lambda_i \eta_j + \varepsilon$$

where
- $t_i$=utility of item i.
- $\mu_i$=mean latent utility of item i. This is how preferable the item is for the average person. (this may also be referred to as a 'threshold').
- $\lambda_i$=loading of item i on the underlying psychological construct/scale. This is how strongly the item differentiates between people at different latent trait levels on the underlying construct. For example, the item 'I find negotiation easy' may differentiate low and high persuasiveness better than the item 'I enjoy making a sale'.
- $\eta_j$=latent trait level of person j on the underlying psychological scale. These are similar to theta scores (although the metric differs, the measured quantity is essentially the same).
- $\varepsilon$=residual variance of utility.

So each item is characterised by two IRT parameters: mean latent utility and loading. These parameters interact with a candidate's latent trait levels to produce utility judgements. Then in a forced-choice comparison, a person compares utilities from different items, and is more likely to prefer items with higher utilities.

The present invention aims to address how a forced-choice testing system based on the Thurstonian IRT methodology may be implemented in practice, and demonstrates how several problems which arise in attempting to do so may be solved. In particular, the invention presents a dynamic system which may not only score but also create subject-specific forced-choice tests.

Test Generator

According to one aspect of the invention, there is provided apparatus (or means, such as a test construction engine, residing within an assessment server) for generating a forced-choice assessment test, the test comprising a sequence of item blocks, each item block comprising a plurality of items to which the subject is required to respond, the apparatus (or means) comprising: means for accessing a database (or content bank), the database adapted to store (for example, in a scale bank) information pertaining to a plurality of scales, each scale being related to a characteristic of the subject to be assessed, and a plurality of items (for example, in an item bank), each item being associated with at least one scale and representing a stimulus to which the subject may respond; and processing means (such as a test construction engine), adapted to generate an item block from items obtained from the database; wherein the processing means is adapted to generate an item block using Thurstonian Item-Response Theory.

The use of Thurstonian Item-Response Theory in the generation of item blocks may allow for the generation of a plurality of unique yet consistent forced-choice assessment tests, each comprising a plurality of item blocks, thereby improving test efficiency, accuracy and enhancing test security. It may also provide for meaningful comparisons to be made between test scores of different subjects or candidates.

Furthermore, the construction of item blocks in accordance with the claimed invention may obviate the need for extensive input from psychologists, as would be required in the traditional method of generation of large numbers of equivalent test forms. This potentially removes a source of human error and enhances test uniformity. It may also facilitate on-the-fly testing.

Typically, an item block comprises at least two (an item pair), preferably three (a triplet), four (a quad) or more items.

Preferably, an item is a stimulus, for example, a statement or question, preferably referring to a characteristic or property. The stimulus may comprise one or more of: an image, a sound, a taste, a texture or a smell. An item may comprise a combination or sequence of stimuli.

Preferably, a scale is a characteristic or a property referred to by an item. Scales may, for example, describe personality traits of individuals or groups. Alternatively, scales may, for example, describe properties of objects. In some embodiments an item may refer to a range of characteristics or properties. The scales, items and scores may relate to preference traits of individuals or groups and/or be used to determine preference traits and/or determine recommendations, optimisations and the like.

Preferably, the processing means is adapted to generate an item block in dependence on a predetermined scale combination or fixed-scale selection plan.

Alternatively, the processing means may be adapted to rank or prioritise the scales. The scales may be ranked according to determined information deficiency.

Preferably, the processing means is adapted to rank the scales according to an assignment of the scales to tiers, wherein the tier to which a scale is assigned relates to the degree of determined information deficiency and/or the number of corresponding items administered or available and/or other relevant measurement targets/constraints suitable for the designed purpose.

Preferably, the processing means is adapted to preferentially select a scale so as to optimise measurement information, preferably to reduce an information deficiency in the test.

Preferably, the processing means is adapted to generate a plurality of scale combinations in dependence on the scale ranking.

Preferably, the processing means is adapted to generate an item block for the most highly ranked scale combination; yet more preferably, for a plurality of ranked scale combinations in order of ranking.

Preferably, the processing means is adapted to maintain a test generation log.

Preferably, the processing means is adapted to terminate at least one of: the test generation, the selection and/or generation of item blocks, the ranking of scales in dependence on a plurality of stopping rules.

According to another aspect of the invention, there is provided a method of generating a forced-choice assessment test, the test comprising a sequence of item blocks, each item block comprising a plurality of items to which the subject is required to respond, the method comprising: accessing a database, the database adapted to store information pertaining to a plurality of scales, each scale being related to a characteristic of the subject to be assessed, and a plurality of items, each item being associated with at least one scale and representing a stimulus to which the subject may respond; and generating an item block from items obtained from the database; wherein the method is adapted to generate an item block using Thurstonian Item-Response Theory.

Preferably, the method further comprises generating an item block in dependence on a predetermined scale combination or fixed-scale selection plan.

Alternatively, the method comprises ranking or prioritising the scales. The scales may be ranked according to determined information deficiency.

Preferably, the method further comprises the ranking of the scales according to an assignment of the scales to tiers, wherein the tier to which a scale is assigned relates to the degree of determined information deficiency and/or the number of corresponding items administered or available and/or other relevant measurement targets/constraints suitable for the designed purpose.

Preferably, scales are preferentially selected so as to optimise measurement information, preferably to reduce an information deficiency in the test.

Preferably, the method further comprises generating a plurality of scale combinations in dependence on the scale ranking.

Preferably, the method further comprises generating an item block for the most highly ranked scale combination; yet more preferably, generating an item block for a plurality of ranked scale combinations in order of ranking.

Preferably, the method further comprises maintaining a test generation log. This may allow the steps in the generation of a particular test to be reconstructed.

Preferably, the method further comprises a plurality of stopping rules for determining whether to terminate at least one of: the test generation, the selection and/or generation of item blocks, the ranking of scales. This may aid test optimisation and/or prevent runaway processes.

In some embodiments, one or more elements of the test may be determined in dependence on data provided by an external source, for example by a requirements characterisation system such as a job analysis tool. In some embodiments, the external source may determine, either directly or indirectly:

The selection of scales for assessment from all available scales in the item bank; and/or The measurement targets and constraints for each scale for assessment, leading indirectly to how scales are prioritised and ranked during a test generation session.

Preferably, the test generation method further comprises:
selecting scales during the assessment generation, such as the selection of scales for item blocks from a predetermined set of scales for assessment; and/or
directly providing information on the ranking of scales/items.

Scale Ranking

According to another aspect of the invention, there is provided apparatus (or means, such as a test construction engine, residing within an assessment server) for generating a forced-choice assessment test, the test comprising a sequence of item blocks, each item block comprising a plurality of items to which the subject is required to respond, the apparatus comprising: means for accessing a database, the database adapted to store information pertaining to a plurality of scales, each scale being related to a characteristic of the subject to be assessed, and a plurality of items, each item being associated with at least one scale and representing a stimulus to which the subject may respond; and processing means, adapted to generate an item block from items obtained from the database; wherein the processing means is adapted to generate the item block in dependence on a ranking of the scales.

Preferably, the processing means is adapted to determine an information deficiency; more preferably, the processing means is adapted to rank the scales according to the determined information deficiency.

Preferably, the processing means is adapted to determine the number of items generated in the test, preferably associated with each scale to be ranked; more preferably, the processing means is adapted to rank the scales according to the number of items generated in the test, preferably determined to be associated with each scale to be ranked.

Preferably, the processing means is adapted to rank the scales in dependence on the determined information deficiency in combination with the number of items generated in the test, preferably determined to be associated with each scale. Preferably, ranking may be done using a combination of information, number of items selected so far and/or other measurement targets and/or constraints relevant for the purpose of the assessment.

Preferably, the processing means is adapted to generate and preferably rank a plurality of scale combinations in dependence on the scale ranking.

Preferably, the processing means is adapted to generate an item block for the most highly ranked scale combination; yet more preferably, for a plurality of ranked scale combinations in order of ranking.

Alternatively, the processing means is adapted to generate a plurality of item blocks for a random subset of possible scale combinations. This may ensure variation between generated assessment tests.

According to another aspect of the invention, there is provided a method of generating a forced-choice assessment test, the test comprising a sequence of item blocks, each item block comprising a plurality of items to which the subject is required to respond, the method comprising: accessing a database, the database adapted to store information pertaining to a plurality of scales, each scale being related to a characteristic of the subject to be assessed, and a plurality of items, each item being associated with at least one scale and representing a stimulus to which the subject may respond; and generating an item block from items obtained from the database; wherein the generating of the item block is in dependence on a ranking of the scales.

Preferably, the method further comprises determining an information deficiency; more preferably, the method further comprises ranking the scales according to the determined information deficiency.

Preferably, the method further comprises determining the number of items generated in the test, preferably associated with each scale to be ranked; more preferably, the method further comprises ranking the scales according to the number of items generated in the test, preferably determined to be associated with each scale to be ranked.

Preferably, the method further comprises ranking the scales in dependence on the determined information deficiency in combination with the number of items generated in the test, preferably determined to be associated with each scale. Preferably, ranking may be done using a combination of information, number of items selected so far and/or other measurement targets and/or constraints relevant for the purpose of the assessment.

Preferably, the method further comprises generating and preferably ranking a plurality of scale combinations in dependence on the scale ranking.

Preferably, the method comprises generating an item block for the most highly ranked scale combination; yet more preferably, generating an item block for a plurality of ranked scale combinations in order of ranking.

Alternatively, the method comprises generating a plurality of item blocks for a random subset of possible scale combinations.

Item Block Construction

According to another aspect of the invention, there is provided apparatus for constructing an item block for use in a forced-choice assessment test of a subject, the item block comprising a plurality of items to which the subject is required to respond, the apparatus comprising: means for accessing a database, the database adapted to store information pertaining to a plurality of scales, each scale being related to a characteristic of the subject to be assessed, and a plurality of items, each item being associated with at least one scale and representing a stimulus to which the subject may respond; means for receiving a request for an item block; and processing means, adapted to construct an item block in dependence on the request; wherein the processing means is adapted to construct the item block from a plurality of items in dependence on the request.

Preferably, the request comprises a set of requested scales of interest.

Preferably, the items are pre-allocated to a plurality of bands according to item properties. The item properties may relate to a scale. More preferably, the processing means is adapted to construct the item block of items from a subset of the bands. This initial selection of suitable items for the scales of interest may result in a further gain in computation efficiency.

Preferably, the processing means is adapted to select items in dependence on the correlation between scales; more preferably, the processing means is adapted to select items within at least one scale correlation tolerance or limit.

Preferably, the processing means is adapted to filter out the least desirable item blocks. In some embodiments, the processing means is adapted to filter out scale combinations according to further criteria.

According to another aspect of the invention, there is provided a method of constructing an item block for use in a forced-choice assessment test of a subject, the item block comprising a plurality of items to which the subject is required to respond, the apparatus comprising: accessing a database, the database adapted to store information pertaining to a plurality of scales, each scale being related to a characteristic of the subject to be assessed, and a plurality of items, each item being associated with at least one scale and representing a stimulus to which the subject may respond; receiving a request for an item block; and constructing an item block in dependence on the request; wherein the method further comprises constructing the item block from a plurality of items in dependence on the request.

Preferably, the request comprises a set of requested scales of interest.

Preferably, the items are pre-allocated to a plurality of bands according to item properties. The item properties may relate to a scale. More preferably, the method further comprises constructing the item block of items from a subset of the bands. This initial selection of suitable items for the scales of interest may result in a further gain in computation efficiency.

Preferably, the method further comprises selecting items in dependence on the correlation between scales; more preferably, the method further comprises selecting items within at least one scale correlation tolerance or limit.

Preferably, the method further comprises filtering out the least desirable item blocks. In some embodiments, the method is adapted to filter out scale combinations according to further criteria.

Item Block Selector

According to another aspect of the invention, there is provided apparatus (or means) for selecting an item block for use in a forced-choice assessment test, the item block comprising a plurality of items to which the subject is required to respond, the apparatus (or means) comprising: means for accessing a database, the database adapted to store information pertaining to a plurality of scales, each scale being related to a characteristic of the subject to be assessed, and a plurality of items, each item being associated with at least one scale and representing a stimulus to which the subject may respond; means for receiving a request for an item block; and processing means, adapted to select an optimum item block (or one of the optimum item blocks) in dependence on the request; wherein the processing means is adapted to select the optimum item block (or one of the optimum item blocks) from a plurality of item blocks in dependence on an information optimisation index.

Preferably, the processing means is adapted to determine the information optimisation index for an item block from the potential information gain from the subject being required to respond to the item block.

Preferably, the information optimisation index is determined from one or more of:
  i) maximising the total information;
  ii) maximising the capped total information;
  iii) minimising the total squared information deficiency;
  iv) maximising the weighted total information;
  v) maximising the product information;
  vi) maximising the product information capped;
  vii) other optimisation index or indices.

Preferably, the processing means is adapted to rank the plurality of item blocks in dependence on the information optimisation index. More preferably, the processing means is adapted to discard from consideration those item blocks for which the information optimisation index is below or above a threshold. In some embodiments, the processing means is adapted to filter out item blocks according to further criteria.

Preferably, the processing means is adapted to rescale and/or relax determination of the item block filling criteria in the event no optimum item block meeting the criteria can be determined.

Typically, the processing means is adapted to select the optimum item block in dependence on the information optimisation index and filtering criteria. Alternatively, the processing means is adapted to randomly select one of the optimum item blocks, preferably in dependence on the information optimisation index and filtering criteria.

In some embodiments, the processing means is adapted to randomly select an item block.

Preferably, the processing means is adapted to construct the plurality of item blocks from which the optimum item block is to be selected.

Preferably, the processing means is adapted to check for item suitability, more preferably to filter the plurality of item blocks in order to remove undesirable item blocks, preferably subject to constraints comprising one or more of:
  i) whether the constituent items of the item block have been used previously;
  ii) the last time the item was used;
  iii) whether constituent pairs of items have been used previously;
  iv) social desirability range/maxima;
  v) total information/minima;
  vi) the number of times an item can be picked in a test;
  vii) the minimum number of intermediate blocks between two blocks containing the same item;

viii) recycling constraints placed on a second test session, which may avoid repetition of contents in the first test session;
ix) items which preferably should not be paired in a test session; and
x) whether non-scored items are allowed, and if so how many are allowed per test form.

Preferably, the processing means is adapted to check for correlation between scales. More preferably, the processing means is adapted to select items in dependence on the correlation between scales, for example within scale correlation tolerances or limits.

Preferably, the processing means is adapted to select scales subject to constraints, preferably including one or more of:
i) the number of times a scale can be picked in a test;
ii) the minimum number of intermediate blocks between two blocks containing the same scale;
iii) the number of times a scale pair can be selected in a test;
iv) the minimum number of intermediate blocks between two blocks containing the same scale pairs;
v) constraints placed on a second test session to avoid repetition of contents in the first test session;
vi) scales which preferably should not be paired under any circumstances in the test session; and
vii) a maximum absolute scale correlation allowed in a forced-choice block, which may avoid comparing scales which are too similar.

Preferably, the processing means is adapted to check scale-level constraints at the scale ranking/selecting phase, preferably resulting in input to item block constructing/selecting phase.

Preferably, the processing means is adapted to select item blocks in dependence upon their item keyed direction combination.

The keyed-direction of an item may relate to the likelihood of a subject preferring an item as determined by the related trait of the subject. A positively-keyed item may be preferred by a subject with a high score for the related trait; a negatively-keyed item may be preferred by a subject with a low score for the related trait.

In some embodiments, the keyed-direction of an item may be defined as follows: Given an item can be in a negating (negative) or in an affirming (positive) relationship (direction) to the underlying scale, and a scale itself can be positive or negative, in a grouping of items such as an item block, the combination of 'negative' and 'positive' items is referred to as the item keyed direction combination. The item keyed direction is akin to a 'polarity' of an item. In particular, ++ or -- (combinations of uniform item keyed directions) and +- (combinations of mixed item keyed directions) groupings of negative and positive items are distinguished.

Preferably, the processing means is adapted to: select a desired item keyed direction combination from a plurality of item keyed direction combinations; and select an item block with the desired item keyed direction combination.

In some embodiments, as an alternative to considering the above two criteria sequentially (as described above), the trade-off between i) desired item keyed direction, and ii) desired item information gain, is considered. In some embodiments, the item keyed direction combination is prioritised and a less optimal item block is selected (according to information optimization index). In other embodiments, the item information gain is prioritised and an optimal item block is selected (according to information optimization index), potentially not necessarily with the desired item keyed direction combination. The decision as to which to prioritise may be controlled by 'Item keyed direction optimisation tolerance factor', an input to the system. The prioritising decision may be calculated for each block, taking into account blocks already generated and measurement target.

Preferably the processing means is adapted to select the desired item keyed direction combination from a plurality of item keyed direction combinations at random and preferably according to a plurality of selection probabilities, each associated with a respective one of the plurality of item keyed direction combinations.

Preferably, the processing means is adapted to modify the selection probability in response to the selection of an item block, the selection probability preferably corresponding to the item keyed direction combination of the selected item block. Preferably, the selection probabilities for all item keyed direction combinations are updated after the selection of one block. This may ensure correct account is taken of the probabilities, such that they sum to unity.

According to another aspect of the invention, there is provided a method of selecting an item block for use in a forced-choice assessment test, the item block comprising a plurality of items to which the subject is required to respond, the method comprising: accessing a database, the database adapted to store information pertaining to a plurality of scales, each scale being related to a characteristic of the subject to be assessed, and a plurality of items, each item being associated with at least one scale and representing a stimulus to which the subject may respond; receiving a request for an item block; and selecting an optimum item block (or one of the optimum item blocks) in dependence on the request; wherein the selecting of the optimum item block (or one of the optimum item blocks) from a plurality of item blocks is in dependence on an information optimisation index.

Preferably, the method further comprises determining the information optimisation index for an item block from the potential information gain from the subject being required to respond to the item block.

Preferably, determining the information optimisation index comprises one or more of:
i) maximising the total information;
ii) maximising the capped total information;
iii) minimising the total squared information deficiency;
iv) maximising the weighted total information;
v) maximising the product information;
vi) maximising the product information capped;
vii) other optimisation index or indices.

Preferably, the method further comprises ranking the plurality of item blocks in dependence on the information optimisation index. More preferably, the method further comprises discarding from consideration those item blocks for which the information optimisation index is below or above a threshold. In some embodiments, item blocks are filtered out according to further criteria.

Preferably, the method further comprises rescaling and/or relaxing determination of the item block filling criteria in the event no optimum item block meeting the criteria can be determined.

Typically, the method comprises selecting the optimum item block in dependence on the information optimisation index and filtering criteria. Alternatively, the method comprises randomly selecting one of the optimum item blocks, preferably in dependence on the information optimisation index and filtering criteria.

In some embodiments, the method comprises randomly selecting an item block.

Preferably, the method further comprises constructing the plurality of item blocks from which the optimum item block is to be selected.

Preferably, the method further comprises checking for item suitability, more preferably, the method further comprises filtering the plurality of item blocks in order to remove undesirable item blocks, preferably in dependence on one or more of:
 i) whether the constituent items of the item block have been used previously;
 ii) the last time the item was used;
 iii) whether constituent pairs of items have been used previously;
 iv) social desirability range/maxima;
 v) total information/minima;
 vi) the number of times an item can be picked in a test;
 vii) the minimum number of intermediate blocks between two blocks containing the same item;
 viii) recycling constraints placed on a second test session, which may avoid repetition of contents in the first test session;
 ix) items which preferably should not be paired in a test session; and
 x) whether non-scored items are allowed, and if so how many are allowed per test form.

Preferably, the method further comprises checking for correlation between scales. More preferably, the method further comprises selecting items in dependence on the correlation between scales, for example within scale correlation tolerances or limits.

Preferably, the method further comprises selecting scales subject to constraints, preferably including one or more of:
 i) the number of times a scale can be picked in a test;
 ii) the minimum number of intermediate blocks between two blocks containing the same scale;
 iii) the number of times a scale pair can be selected in a test;
 iv) the minimum number of intermediate blocks between two blocks containing the same scale pairs;
 v) constraints placed on a second test session to avoid repetition of contents in the first test session;
 vi) scales which preferably should not be paired under any circumstances in the test session; and
 vii) a maximum absolute scale correlation allowed in a forced-choice block, which may avoid comparing scales which are too similar.

Preferably, the method further comprises checking scale-level constraints at the scale ranking/selecting phase, preferably resulting in input to item block constructing/selecting phase.

Preferably, the method further comprises selecting item blocks in dependence upon their item keyed direction combination.

Preferably, the method further comprises: selecting a desired item keyed direction combination from a plurality of item keyed direction combinations; and selecting an item block with the desired item keyed direction combination.

Preferably the method further comprises selecting the desired item keyed direction combination from a plurality of item keyed direction combinations at random and preferably according to a plurality of selection probabilities, each associated with a respective one of the plurality of item keyed direction combinations.

Preferably, the method further comprises modifying the selection probability in response to the selection of an item block, the selection probability preferably corresponding to the item keyed direction combination of the selected item block.

Testing System

According to another aspect of the invention, there is provided a system for assessing a subject by means of a forced-choice assessment test, comprising: means for constructing a test, the test comprising a plurality of item blocks, wherein each item block comprises a plurality of items to which the subject is required to respond, and each item is associated with at least one scale and represents a stimulus to which the subject may respond; means for applying the test to the subject; means for scoring the subject response to the test; and means for assessing a subject characteristic based on the subject test response score; wherein the means for constructing the test and the means for scoring the subject response to the test use dominance Thurstonian Item-Response Theory.

Preferably, the means for constructing a test is adapted to construct at least one item block at the start of the test. In some embodiments, the means for constructing a test is adapted to construct all the items blocks for the test at the start of the test. In other embodiments, the means for constructing a test is adapted to construct groups of item blocks during the test. Preferably, the means for constructing a test is adapted to construct item blocks during the test in dependence upon the system receiving (and preferably scoring) at least one subject response.

Preferably, the means for constructing a test is adapted to at least partially construct a test in dependence upon receiving (and preferably scoring) at least one subject response.

In some embodiments, the means for constructing a test is adapted to construct a test from a pre-determined input, such as a fixed form, or a random selection from several equivalent fixed forms.

According to another aspect of the invention, there is provided a method of assessing a subject by means of a forced-choice assessment test, comprising: constructing a test, the test comprising a plurality of item blocks, wherein each item block comprises a plurality of items to which the subject is required to respond, and each item is associated with at least one scale and represents a stimulus to which the subject may respond; applying the test to the subject; scoring the subject response to the test; and assessing a subject characteristic based on the subject test response score; wherein constructing the test and scoring the subject response to the test uses dominance Thurstonian Item-Response Theory.

Preferably, constructing a test comprises constructing at least one item block at the start of the test. In some embodiments, all the items blocks for the test may be constructed at the start of the test. In other embodiments, groups of item blocks may be constructed during the test. Preferably, item blocks constructed during the test are determined in dependence upon receiving (and preferably scoring) at least one subject response.

Preferably, the constructing of the test comprises at least partially constructing the test in dependence upon receiving (and preferably scoring) at least one subject response.

In some embodiments, the test is constructed from a pre-determined input, such as a fixed form, or a random selection from several equivalent fixed forms.

Testing Server

According to another aspect of the invention, there is provided a system for assessing a subject by means of a forced-choice assessment test, comprising: a server, adapted to interact with the subject to be tested; a database, adapted to store a plurality of scales, each scale representing a characteristic, and a plurality of related items, each item being associated with at least one scale and representing a stimulus to which the subject may respond; means for retrieving an item from the database; means for constructing a test, the test comprising a plurality of item blocks, wherein each item block comprises a plurality of items to which the subject is required to respond; means for applying the test to the subject; means for scoring the subject response to the test; and means for assessing a subject characteristic based on the subject test response score; wherein the means for constructing the test and the means for scoring the subject response to the test use dominance Thurstonian Item-Response Theory.

According to another aspect of the invention, there is provided a method of assessing a subject by means of a forced-choice assessment test, comprising: interacting with the subject to be tested; accessing a database, the database being adapted to store a plurality of scales, each scale representing a characteristic, and a plurality of related items, each item being associated with at least one scale and representing a stimulus to which the subject may respond; retrieving an item from the database; constructing a test, the test comprising a plurality of item blocks, wherein each item block comprises a plurality of items to which the subject is required to respond; applying the test to the subject; scoring the subject response to the test; and assessing a subject characteristic based on the subject test response score; wherein the constructing the test and scoring the subject response to the test uses dominance Thurstonian Item-Response Theory.

Aspects of the invention may provide one, some or all of the following, in any appropriate combination:
  promotion of computational efficiency
  on-demand, dynamic generation of triplets (or alternatively pairs, quads, or other multiplets) from an item bank
  use of Linear On-the-Fly Testing (LOFT) and/or input of Multiple Pre-determined Test Forms (MPTF) to create forced-choice questionnaires for determination of traits (preferably personality traits), wherein generally MPTF/LOFT result in equivalent tests, and CAT in tailored tests
  adaptation for use online or offline
  the construction and scoring of equivalent tests, or tailored tests dependent on test subject responses, comprising multidimensional triplets or alternatively pairs, quads, or other multiplets (preferably in combination with MPTF, LOFT or CAT)
  adaptation of a test in dependence on test subject responses, in order to target the test to the individual being tested i.e. use of Computer Adaptive Testing (CAT)
  modularity, through the ability to choose a subset of traits to be measured from a set of predetermined scales
  the adaptive selection of suitable scales and/or items and/or triplets or alternatively pairs, quads, or other multiplets according to ranking by information deficiency and/or other indices such as social desirability
  the adaptive adjustment of scale and/or item and/or item block filtering constraints dependent on item availability
  the (optional) pre-selection of suitable scales and/or items and/or triplets for further consideration by use of an initial coarse filter
  traits being measured may include: personality traits; competencies; product characteristics; or other traits.

The invention may provide a system with one or more of the following features: configurable, dynamic, computer adaptive, forced-choice, multidimensional, pairs, triplets, quads (and higher multiplets), Thurstonian IRT.

The terms subject, candidate and respondent are used herein interchangeably.

The term assessment is to be understood in its broader, general meaning as relating to evaluation or estimation and not limited to personality assessment.

Where an example embodiment demonstrates the use of triplets of items, many of the techniques described can also be applied to pairs and extended to quads and higher orders.

Further features of the invention are characterised by the dependent claims, where appended.

The invention also provides a computer program and a computer program product for carrying out any of the methods described herein, and/or for embodying any of the apparatus features described herein, and a computer readable medium having stored thereon a program for carrying out any of the methods described herein and/or for embodying any of the apparatus features described herein.

The invention also provides a signal embodying a computer program for carrying out any of the methods described herein, and/or for embodying any of the apparatus features described herein, a method of transmitting such a signal, and a computer product having an operating system which supports a computer program for carrying out the methods described herein and/or for embodying any of the apparatus features described herein.

The invention extends to methods and/or apparatus substantially as herein described with reference to the accompanying drawings.

Any feature in one aspect of the invention may be applied to other aspects of the invention, in any appropriate combination. In particular, method aspects may be applied to apparatus aspects, and vice versa.

Equally, the invention may comprise any feature as described, whether singly or in any appropriate combination.

Furthermore, features implemented in hardware may generally be implemented in software, and vice versa. Any reference to software and hardware features herein should be construed accordingly.

The invention will now be described, purely by way of example, with reference to the accompanying drawings, in which:

FIG. 1 shows examples of item blocks in forced-choice instruments;

FIG. 3 shows an example of scale information;

FIG. 4 shows an example of item bank information;

FIG. 10 shows an example of scale ranking;

FIG. 17 shows an example of a subject response;

FIG. 18 shows an example of subject response scoring;

FIG. 19 shows an example of a test report; and

TECHNICAL TERMINOLOGY

Figure 2:
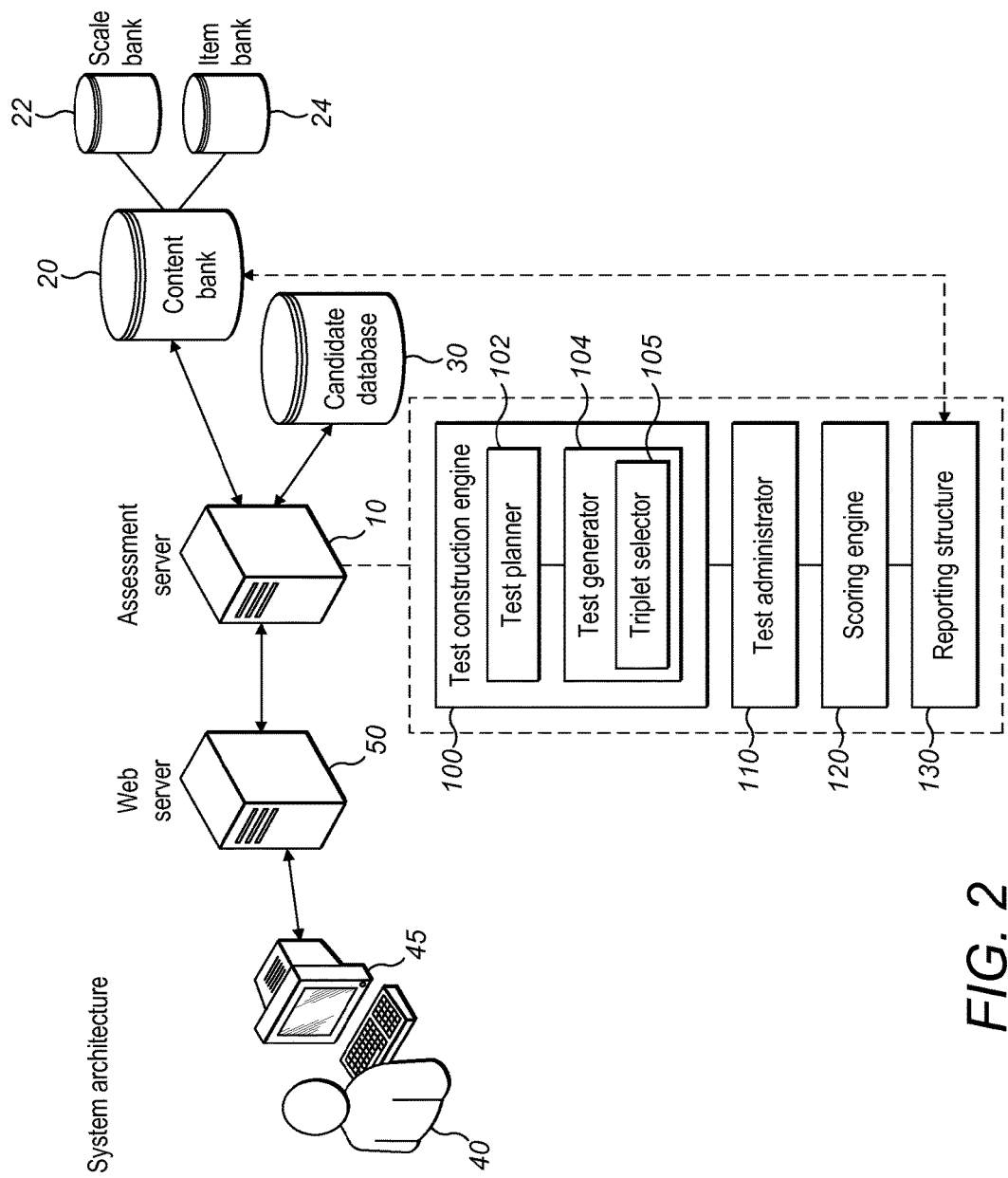
FIG. 2 shows a high-level overview of the system architecture.

The following are preferred definitions of terms:

Item—A statement/single stimulus with IRT parameters contributing to measurement of a particular scale.

Scale/Construct—A psychological construct that can be measured by items (e.g. openness and conscientiousness are scales of personality). The terms scale and construct are used interchangeably.

Forced-Choice—A question format in which candidates are required to make comparison of multiple items and indicate preferences.

Pair/Triplet/Quad—Two/three/four items presented in forced-choice format requiring comparison. These may also be referred to as an item block, generally multiplets. Triplets are sometimes referred to as "triads"; Quads are sometime referred to as "tetrads".

Instrument—whole test consisting of many multiplets.

Thurstonian IRT—An IRT model developed by Brown & Olivares (2011) that is specifically designed to score forced-choice data.

Multidimensional/Uni-dimensional Comparison—Questions comparing items coming from different/the same scale or construct.

CAT—Computer (or Computerised) Adaptive Testing, wherein the subject responses are scored as the test progresses, with subsequent test instruments determined from the scores obtained from responses to earlier instruments, the purpose preferably being to maximise the precision of the test outcome. Requires constant subject input as the test proceeds.

LOFT—Linear On-the-Fly Testing, wherein a different test is created 'on-the-fly' for each subject, typically using an IRT model to select from a bank of items, the purpose preferably being to ensure candidates sit equivalent yet ideally unique tests. This may help to reduce test fraud. A LOFT format is also useful where constant subject input is impossible or may be intermittent, for example due to lack of or breaks in communication with the assessment server. LOFT forms may, for example, be printed on paper. This may allow for unique yet consistent printed tests, or ones which are workable even if internet connectivity is poor (as may be the case, for example, in some developing countries). In practice, the LOFT approach typically involves creating items targeted at the average person and setting a threshold so that say 90% of the population will be measured accurately.

MPTF—Multiple Pre-assembled Test Forms, wherein one or more equivalent, for example LOFT, forms are created for the target population before the test session. LOFT forms may, for example, be printed on paper. This may allow for unique yet consistent printed tests, or ones which are workable even if internet connectivity is poor (as may be the case, for example, in some developing countries).

FIXED—A single fixed form.

P&P—Pen and Paper.

Overview

A typical assessment or testing process or project has three main stages:

I. Measurement Decision

The first stage of the assessment project is to determine what psychological constructs (scales) are important for the specific business needs of the project. In selection this is typically done through job analysis. Both data analytics and expert judgements can be used to make the measurement decision. For example, the following three specific constructs (scales) may be selected to predict performance in a sales role: Persuasive, Conscientious, Achieving.

II. Measurement

Instruments are created (either on-the-fly during a test session or prior to test candidate log-in) that measure the key psychological constructs identified in stage I (e.g. Persuasive, Conscientious, Achieving). The system creates instruments that:

Measure the selected scales only (enhance measurement efficiency);

Are forced-choice (reduce biases and faking);

Are different for each candidate (provide better test security);

Are created and scored using Thurstonian IRT (enhance measurement efficiency and accuracy).

Constructs suitable for psychometric testing with forced-choice instruments (such as this new assessment system) include those which are typically measured through self-report such as personality, competency, motivation, engagement and other similar psychological constructs. The forced-choice format is also suitable for measuring situational judgement and performance. These may be measured using the Thurstonian IRT testing system outlined in this document.

Constructs which are less suitable (or entirely unsuitable) for psychometric testing with forced-choice instruments include for example verbal comprehension, numerical ability, inductive reasoning, oral communication and other similar psychological constructs. These will be measured using other testing systems or alternative means.

III. Reporting

Measurement results (e.g. scale scores on Persuasive, Conscientious, Achieving) from the psychometric test are collated in a feedback report.

FIG. 1 shows examples of item blocks in forced-choice instruments, including (a) a pair, (b) a triplet and (c) a quad. Higher order item blocks are also possible.

System Architecture

FIG. 2 shows a high-level overview of the system architecture.

Assessment server 10 has access to a content bank 20 and a candidate or subject database 30. These databases may be combined into a single database or separated, potentially geographically. A user or subject 40 typically accesses the assessment server 10 over the internet via web server 50 from a user terminal 45.

Content Bank 20 comprises a scale bank 22, storing scale properties and an item bank 24, storing item properties and also further information regarding the relationships between items and scales.

The terms 'item bank' and 'content bank' are sometimes used interchangeably.

An item bank (or content bank) contains scale information and item information, and information on how scales and scales/scales and items relate to each other. It may require two or more sub-datasets to store all such contents.

Typically, the following information is stored in elements of the content bank 20:

Scale bank: scale ID, scale name, scale direction (positive or negative);

Item bank: item ID, item text, scale(s) measured by item, item parameters, item keyed direction, social desirability Scale relationship: covariance matrix of scales Depending on the number of scales that can be measured, an item bank 24 can comprise for example approximately 2,000 to 3,000 items, each item being for example a statement such as "I keep a tidy sock drawer".

FIG. 3 shows an example of scale bank information. Here scale ID 300, scale name 302, scale direction 304 and the number of items 306 associated with each scale are indicated.

In some embodiments, additional fields are also stored e.g. correlation between scales, whether a scale is applicable to particular job levels etc.

FIG. 4 shows an example of item bank information. Here item ID 400, item text 410, scale(s) measured by item 402, item parameters (loading 404 and threshold 406), and social desirability 408 are indicated.

In some embodiments, additional fields are also stored e.g. item uniqueness variance, whether an item is applicable to particular job levels, etc.

In the illustrated example further variables associated with items are shown, including the number of times 412 an item has been selecting in a test being generated, a flag 414 indicating whether the item was selected in the last 2 triplets in the test being generated, and a flag 416 indicating whether the item is available for selection in the test being generated. In some embodiments, these variables are stored elsewhere, for example in the test generation system.

In some embodiments, the content bank 20 may be independent of the other system parts, making the system suitable for use with other content banks where the format of the test is similar.

Candidate Database 30 stores candidate information, tests, responses, scores (such as theta scores), etc. Multiple datasets may be required to store different types of candidate information.

Assessment server 10 further comprises the following modules:

Test Construction Engine module 100 generates dynamic test forms according to the test construction specifications or parameters.

Test Planner or Configurator module 102 provides test configuration inputs to the testing system, indicating what the test should measure (scales), how accurate the measurement needs to be, how long the test should be, etc. The information can come from job analysis, client specification, professional services recommendation, requirements generation systems etc.

Test generator module 104 comprises an embedded triplet selector 105.

Test administrator module 110 controls interaction with the subject during the test-taking process.

Scoring Engine module 120 uses IRT scoring to score the dynamically generated test forms. The system uses a scoring process and (optional) response consistency checker. The system can iterate between test construction, test administration and scoring to produce computer adaptive testing.

Reporting Structure module 130 creates reports suitable for project need based on test results. The reporting structure sits independent of the test constructing and scoring system parts but is likely to have association with the content bank.

These various modules may be implemented on one or more computer servers.

Suitable computer servers may run common operating systems such as the Windows systems provided by Microsoft Corporation, OS X provided by Apple, various Linux or Unix systems or any other suitable operating system.

Suitable databases include ones based on SQL, for example as provided by Microsoft Corporation or those from Oracle or others.

Embodiments of the invention may also be implemented in Microsoft Excel or similar business software.

Optional web server 50 provides remote access to the assessment system via a website or other remotely-accessible interface. Web interfaces and other code may be written in any suitable language including PHP and JavaScript. A Microsoft .Net based stack may be used.

System Operation Overview

Figure 5:
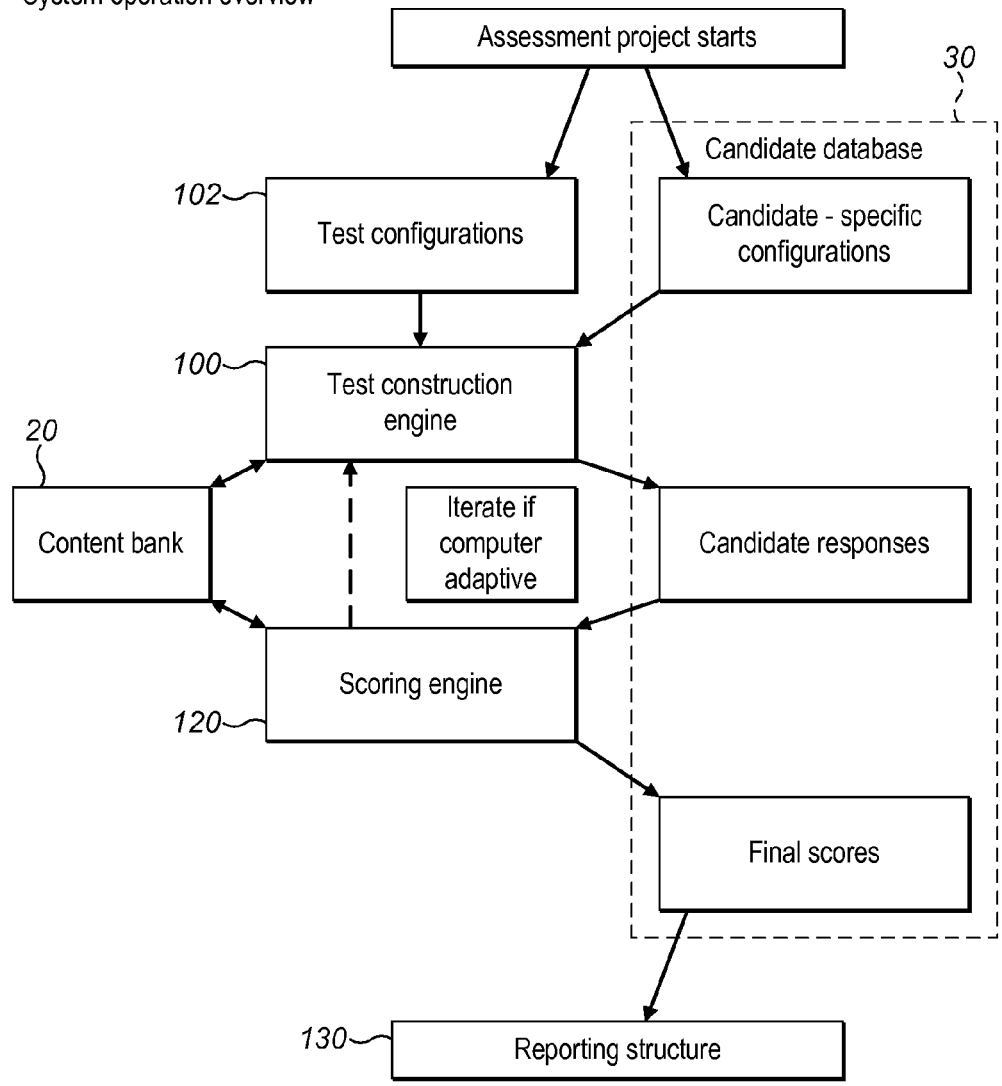
FIG. 5 shows the system operation in overview.

FIG. 5 shows the system operation in overview.

At the top level, the steps involved are:

Select constructs (from an overall set) to measure and determine assessment configurations Identify which candidates should complete the assessment and determine any additional candidate-specific assessment configurations Candidate sits assessment Test construction engine draws content from Content Bank based on pre-defined parameters; and connects with Scoring Engine (if a computer adaptive (CAT) model is applied)

The candidate responds to the assessment and the assessment is scored (either iteratively, after each question for a CAT application; or after all questions have been completed for a LOFT/MPTF/FIXED application)

The scoring engine 120 produces a final theta score estimate

Candidate score is stored in the candidate database 30

User can view candidate scores and/or obtain reports from the Reporting structure module 130.

In some embodiments, a hybrid CAT and LOFT sequence may be employed, for example with sequences of one separated by instances of the other. An example of this would be as in the following steps:

1. Subject answers a LOFT sequence, say five blocks of triplets
2. The results are scored
3. Based on the score, a further five blocks of triplets are selected for the next LOFT sequence (effectively a CAT instance)
4. If test complete condition not satisfied, Return to step 1, else
5. Compute overall test score The test complete condition may be the completion of a set number of LOFT or CAT sequences and/or the convergence of the resulting calculated subject characteristics. In a CAT application, conditions may be defined for the system to commence the scoring; for example, it may be more efficient to commence scoring only after the first 10 triplets have been completed by the subject. Similarly, in a hybrid CAT and LOFT application conditions may be defined for the system to commence scoring.

Figure 6A:
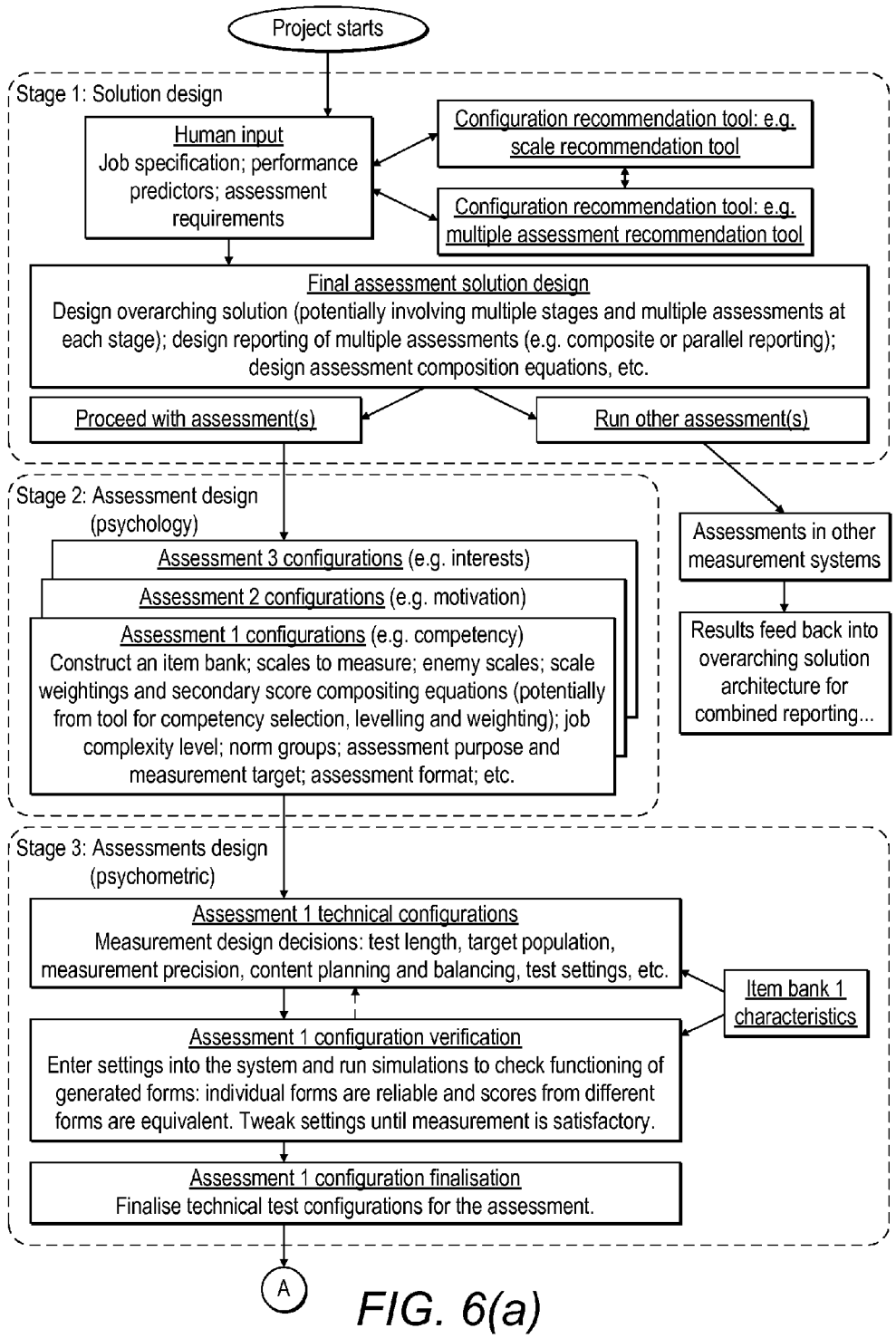
FIG. 6 shows the system overview of an alternative embodiment.
Figure 6B:
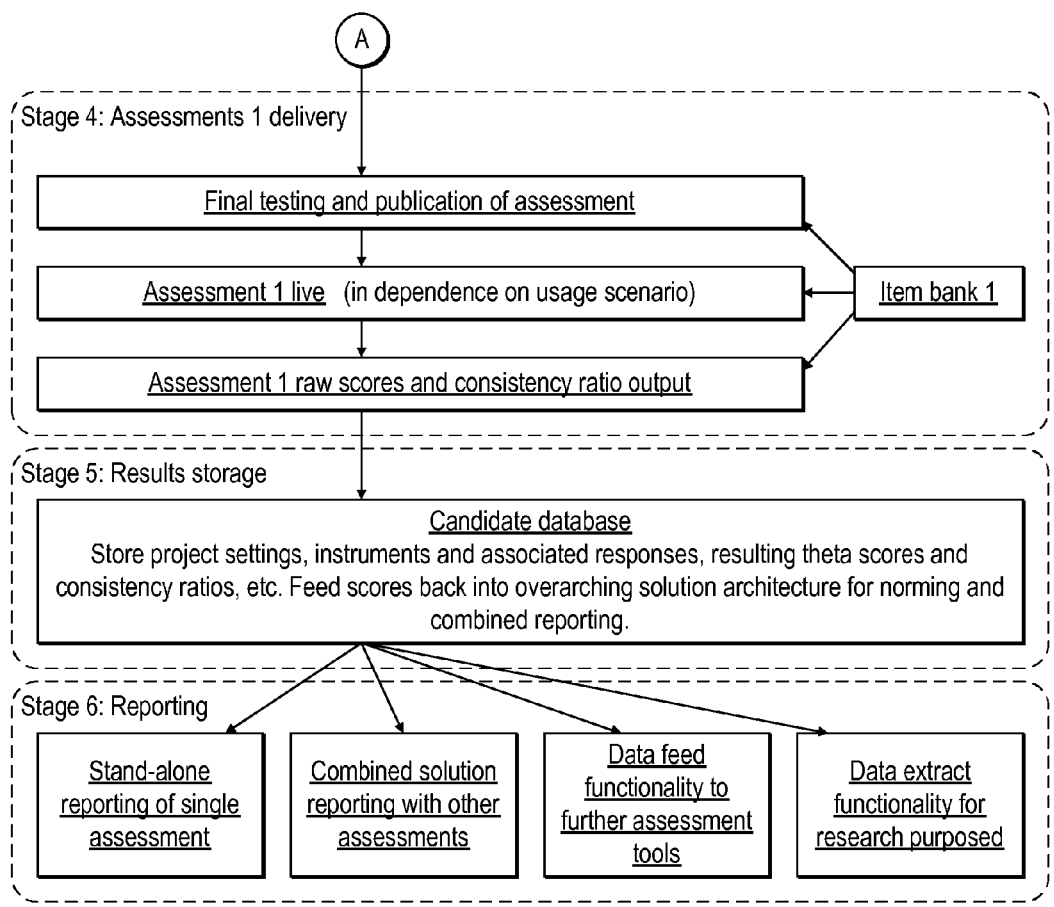
Figure 7A:
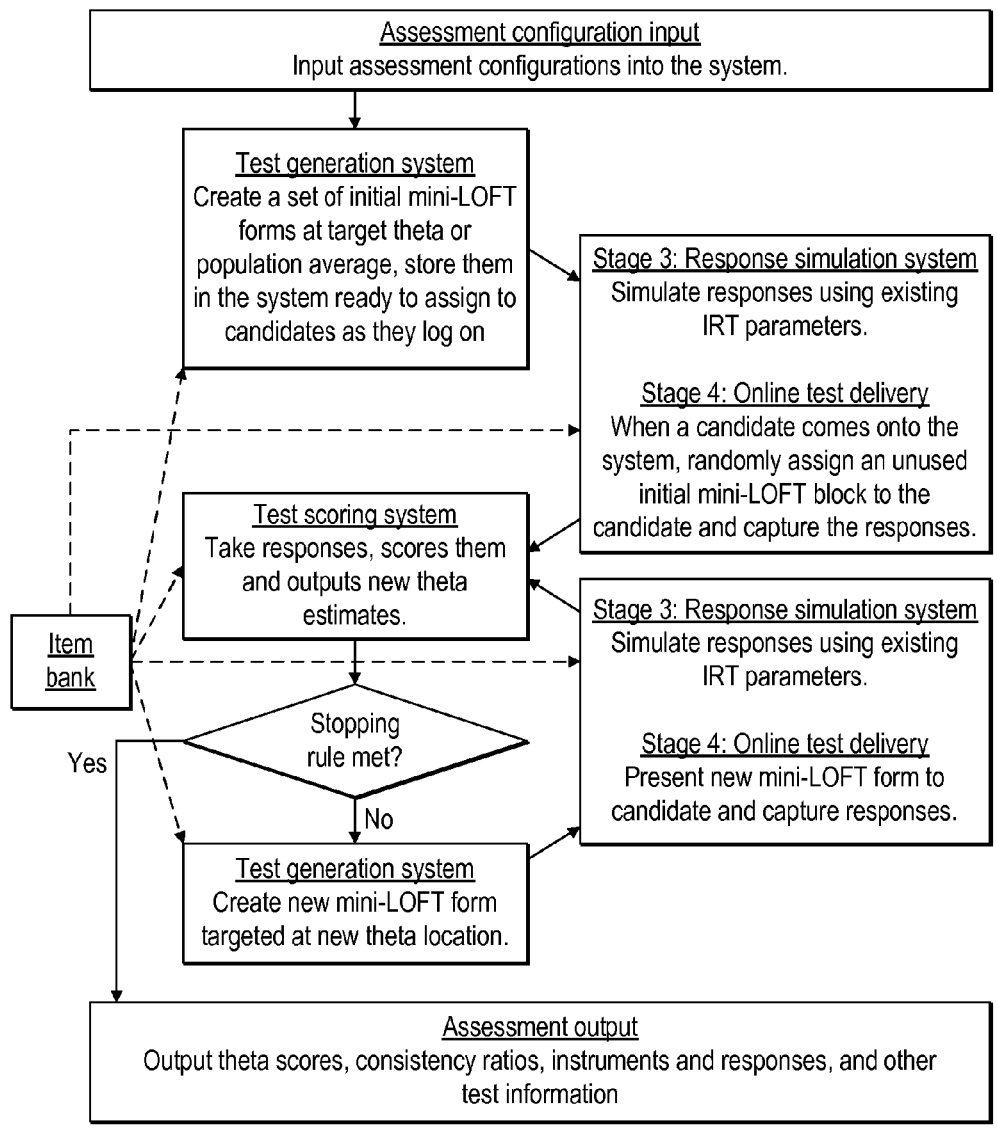
FIGS. 7 (a-e) show examples of various usage scenarios.
Figure 7B:
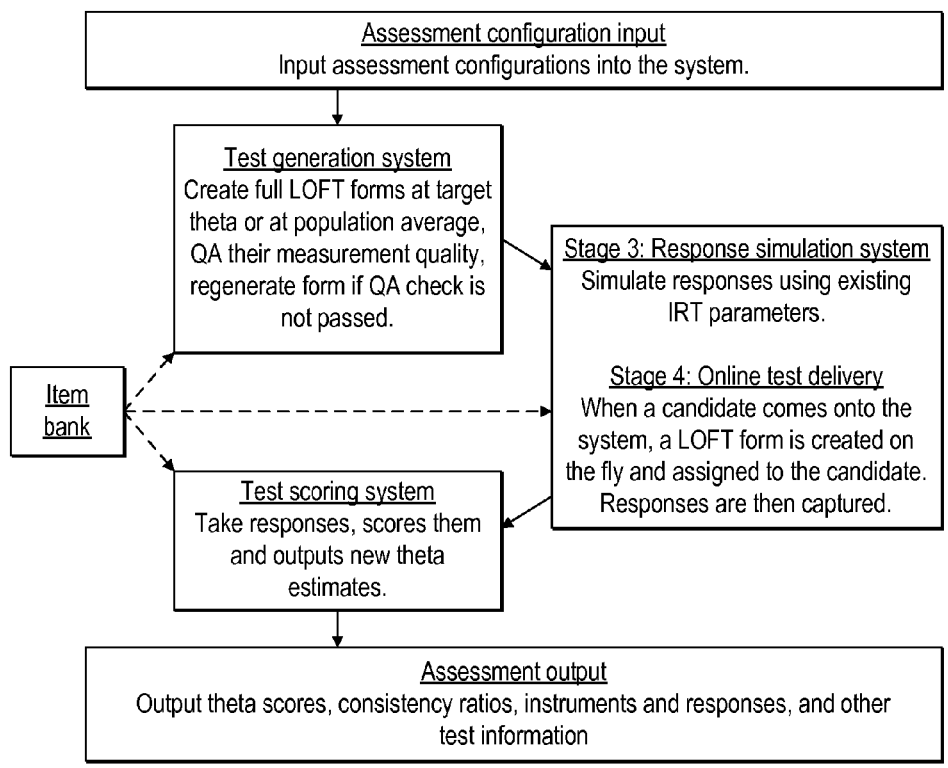
Figure 7C:
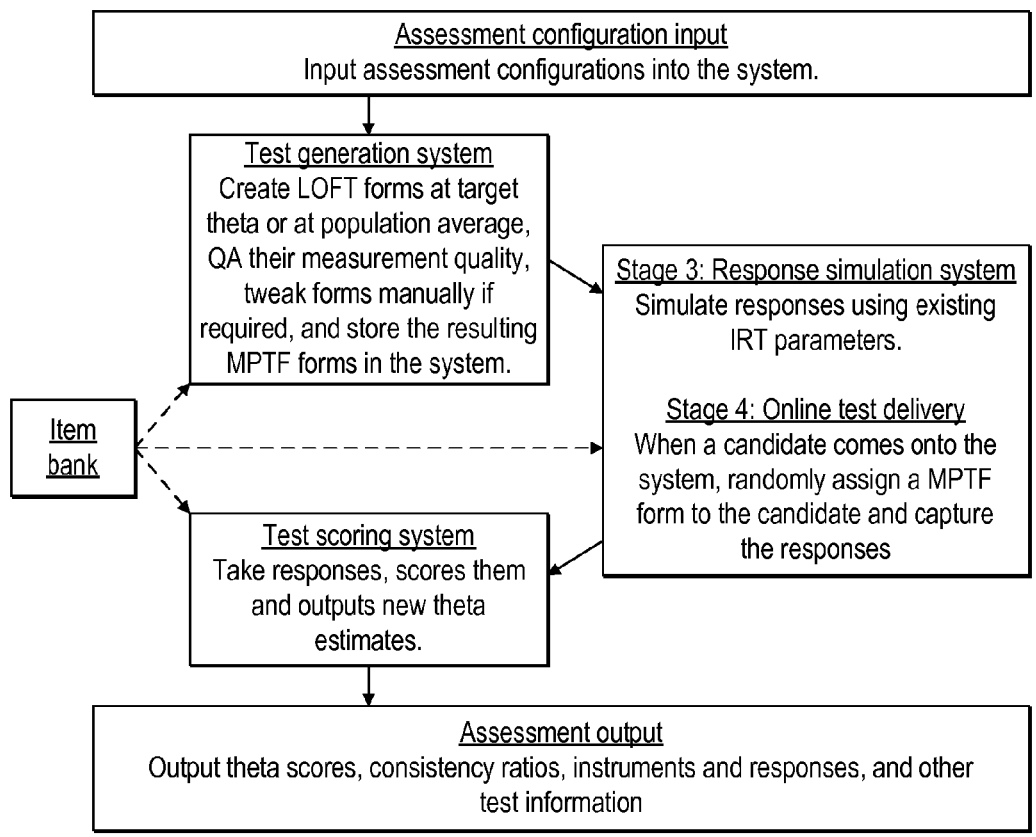
Figure 7D:
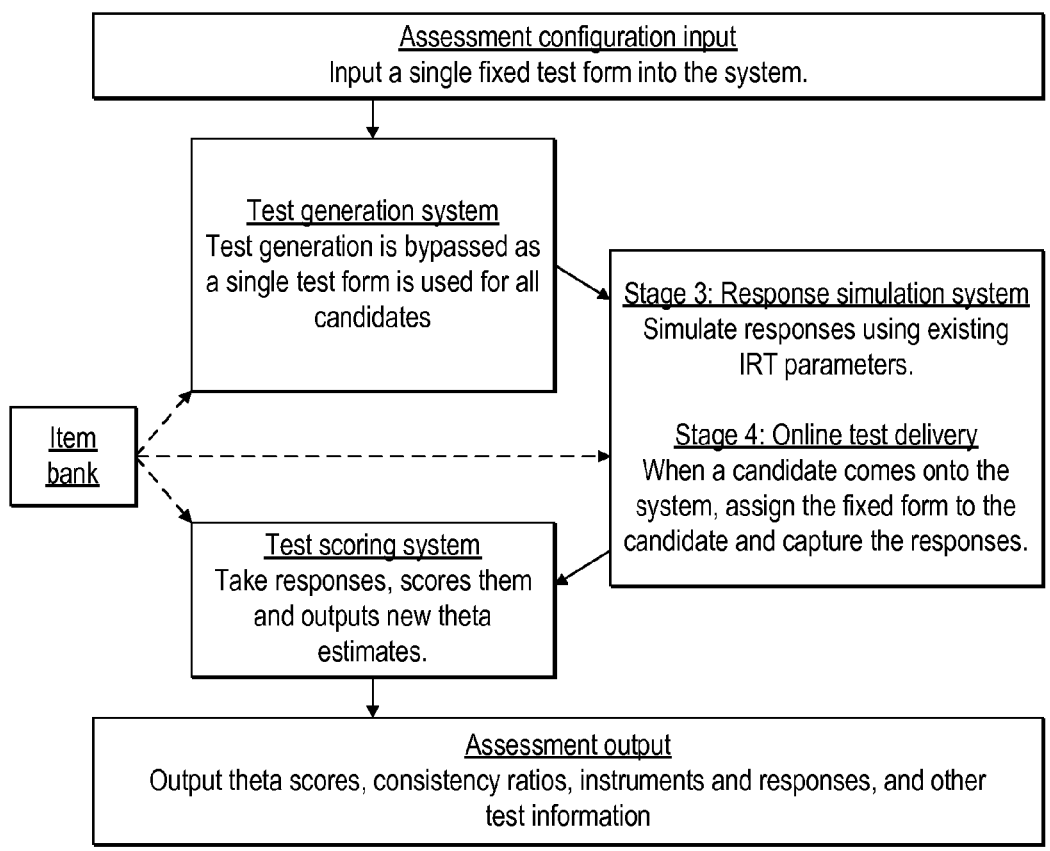
Figure 7E:
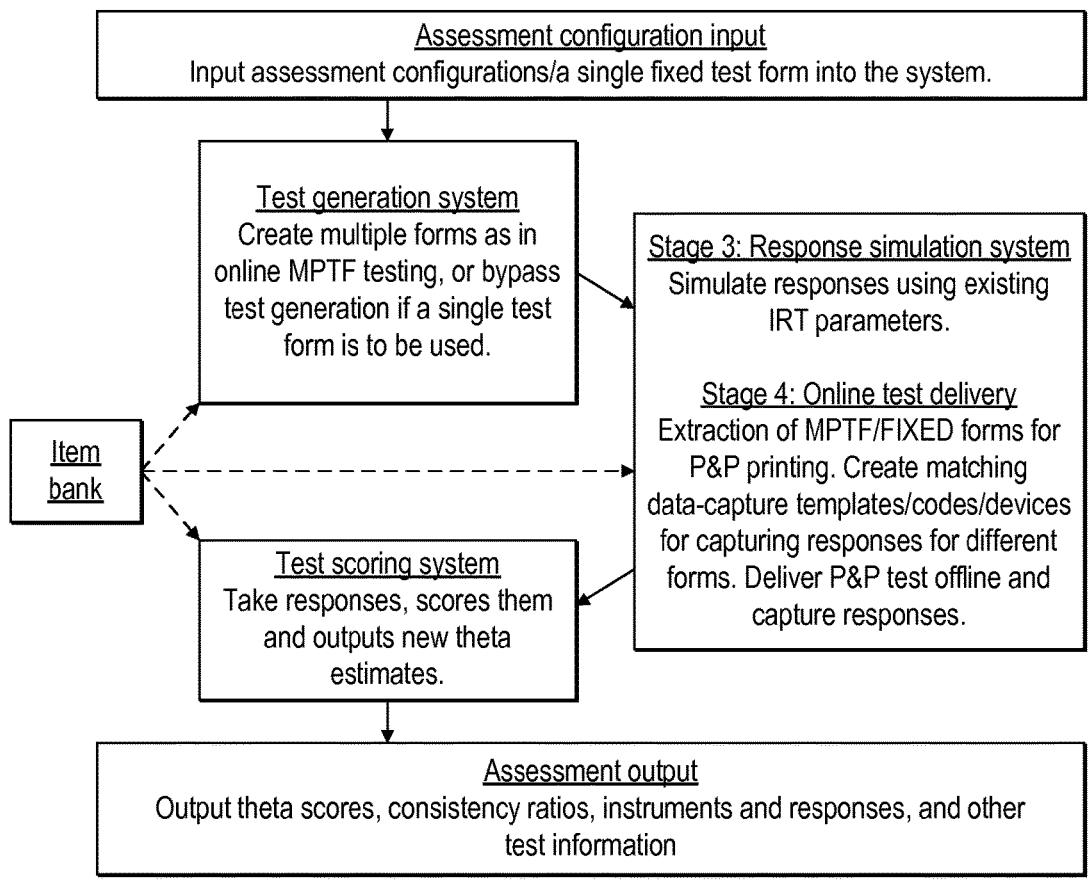

FIG. 6 shows the system overview of an alternative embodiment.

Each stage in the human-computer integrated usage workflow is controlled by and requires input from different users. The stages in the illustrated workflow are:

| Stage | Workflow Tasks |
|---|---|
| 1 | Determine and clarify project targets and requirements. Design assessment solutions to meet project need. |
| 2 | Determine detailed measurement requirements and general configurations for the assessments. |
| 3 | Determine detailed technical configurations for the assessments. |
| 4 | Test and publish the assessment on the live system. Conduct regular checks to ensure system functioning while test is live. |
| 5 | Ensure the assessments and results are recorded properly in the database. |
| 6 | Report and interpret results in assessment project. Utilise assessment results to further develop and refine assessment offerings. |

The assessment that is produced and delivered in Stage 4 ('Assessment 1 Live') depends on the usage for which the assessment is intended. A number of usage scenarios are now described in more detail.

Usage Scenarios

Each assessment can adopt one of the following main usage scenarios:

Computer Adaptive Testing (CAT) online

Linear on-the-fly Testing (LOFT) online

Multiple Preassembled Test Forms (MPTF) online

One single fixed form (FIXED) online

Paper and Pencil (P&P) administration offline (i.e. MPTF/FIXED offline)

Repeated Testing (ReTest)

In addition, it is possible to conduct assessments in more than one time points using any combination of the above usage scenarios.

The following table gives more details on the features of each of these usage scenarios.

| Scenario | Test Form Generation | Pros | Cons |
|---|---|---|---|
| CAT | Test consists of mini-LOFT blocks which are created on the fly during the test session, adapting to candidate responses. | Maximise measurement precision for each individual. Can have fixed or varying test length. | Tests adaptive so not equivalent for all. Very computer intensive. Requires constant internet access. |
| LOFT | A LOFT form is created on-the-fly as each candidate logs onto the system. | Maximise measurement precision at target scale locations. Can have fixed or varying test length. Tests equivalent for all. Do not require constant internet access. | Measurement less accurate for the extreme profiles. |
| MPTF | One or more equivalent forms are created for the target population before the test session. The test construction algorithm for LOFT may be utilised to generate the initial forms. The forms may be manually checked and tweaked when needed. Resulting forms are then assigned, preferably randomly, to candidates as they log onto the system. | Maximise measurement precision at target scale locations. Good control over test length and measurement equivalence. Do not require constant internet access. | Measurement less accurate for the extreme profiles. Test security is lower than in the cases of dynamic assessments. |
| FIXED | A single fixed form is entered into the system. The test generation part of the system is bypassed and only the Thurstonian IRT scoring functionality is utilised. | Maximise measurement precision at target scale locations. Fixed test length. Greatest measurement equivalence. Do not require constant internet access. Useful when usage of multiple forms is not desirable. | Measurement less accurate for the extreme profiles. |
| P&P | Forms created as in MPTF/FIXED scenario, then administered on P&P at some test centre. | Minimum technological requirement from candidate. Good control over test length and measurement equivalence. Do not require internet access. | Measurement less accurate for the extreme profiles. Administrative burdens and technological complexities relating to printing test forms and capturing responses. |

-continued

| Scenario | Test Form Generation | Pros | Cons |
|---|---|---|---|
| ReTest | Choose one or more of the above delivery methods and use them in different test sessions, depending on the purpose of each test session. Candidate responses in earlier sessions could be used to guide test generation in later sessions. Responses from different sessions can be combined or kept separate for scoring. | Flexible multi-stage assessment design suited to project requirements. | Results from different test sessions may differ. |

The choice of usage scenario is largely driven by assessment purposes and constraints. For example:

| Situation | Recommendation |
|---|---|
| An assessment where the candidates are unlikely to have access to the internet (at home or at a test centre). | P&P |
| An assessment where the candidates are likely to have some access to the internet but the speed and stability cannot be guaranteed. | MPTF or LOFT |
| An assessment for sieving out candidates using some cut scores. | MPTF or LOFT |
| An assessment where standardising the test experience across all candidates is more important than the gain in measurement precision using adaptive testing. | MPTF or LOFT |
| An assessment requiring comprehensive profile measurement for each candidate. | CAT |
| A two-stage assessment, with a quick first test targeted at pass/fail cut scores, followed by a detailed comprehensive profile measurement for candidates who passed the first test. | ReTest (LOFT then CAT) or (Session 1: LOFT; Session 2: CAT. Based on results from session 1, only selected candidates are passed through to session 2) | human administrative input from test administrators, although the system needs an actual candidate to respond to the questions in a live test session.

The ReTest scenario is not shown here, but it is essentially a sequence of some logical combination of the main usage scenarios plus potential human administrations in between. Note that in a ReTest design the scores from earlier tests could be used as starting points of later tests, if it is desired to do so.

FIGS. 7 (*a-e*) show examples of various usage scenarios.

FIG. 7(*a*) shows Computer Adaptive Testing (CAT) online.

FIG. 7(*b*) shows Linear on the Fly Testing (LOFT) online.

FIG. 7(*c*) shows Multiple Preassembled Test Forms (MPTF) online.

FIG. 7(*d*) shows One single fixed form (FIXED) online.

FIG. 7(*e*) shows Paper and Pencil (P&P) administration offline (i.e. MPTF/FIXED offline).

System Features and Advantages

The system offers a configurable assessment tool with a Forced-Choice format and the application of Thurstonian IRT to create and score dynamic test forms, with the following key features and advantages (the system can comprise any of these features, either singly or in any appropriate combination):

| Key Features | Advantages |
|---|---|
| Configurable construct selection | Content is configurable to measurement need, questionnaire is bespoke to business requirements, greater flexibility, reduced assessment time. |
| Item Bank | Improved test security, greater flexibility, potentially different test for each candidate. |
| Dynamic Linear-on-the-fly (LOFT) or Adaptive (CAT) test construction (from item bank) | Test forms are created on-the-fly, IRT test construction reduces assessment time and improves measurement efficiency, adaptive testing tailors test to each individual. |
| Thurstonian IRT Scoring | Reduced assessment time, improved measurement efficiency and accuracy |
| Forced choice format | Enhanced resistance to faking and response biases |
| Multidimensional | Blocks of items may be constructed from different scales or constructs, allowing for greater resistance to faking and improved test efficiency and accuracy |
| Triplets, can be extended to pairs, quads or other multiplets | Reduces testing time and hence improves measurement efficiency |

The following flowcharts expand the workflow for each of the main usage scenarios. Note that apart from assessment set-up and testing, P&P administering, and P&P data capture, all other processes are automated and do not require Combining all of these together allows users to achieve the greatest efficiency of measurement a focused tool, which is quicker to complete, yet maintains (or increases) precision of measurement.

The purpose of the system is to allow the quick and efficient creation of focussed assessments which are more robust to response distortions, thereby providing the most efficient measurement tool for the application in question.

For many clients a short assessment time is key a tool designed in this way can minimise assessment time, without losing precision of measurement.

This system design can be applied to a range of "constructs" (e.g. competencies, personality, interests, motivation, values, performance).

The system can potentially be used across the employee life cycle in both selection and development contexts. It may be of particular value in high volume sifting and selection contexts.

The system can be used internationally, allowing for a multinational corporation to conduct assessments and compare outcomes across its entire business.

The system is aimed at both experienced users of psychometrics (e.g. occupational/industrial psychologists) and at line managers who are looking for outputs to support their people decision-making processes.

To the best of the inventors' knowledge, the system outlined in this document is the first ever dynamic forced-choice testing system employing the Thurstonian IRT measurement model.

Because the IRT measurement model used is different from those in existing dynamic forced-choice testing systems, the underlying test construction structure and logic are innovative. Moreover, the system will be able to dynamically create triplets and quads from an item bank using IRT, whereas so far in the market only pairs were created dynamically.

Generation of triplets (and higher-order blocks) on-the-fly by the system described ensures that the triplets are essentially pseudorandom; with each test being effectively unique, a subject is highly unlikely to sit the same test twice and no two subjects are likely to sit the same test. This can reduce cheating and/or faking by test takers and generally increases the reliability of the tests.

The system is intended for next-generation personality competency measurement products, which will use a forced-choice multidimensional triplet question format. The system can be extended to additional applications, including (but not limited to):

Measuring other psychological constructs, such as motivation, engagement, interests, values, situational judgement, performance, etc.

Constructing and scoring forced-choice tests that use one or a combination of pairs, triplets, quads or any other multidimensional and/or uni-dimensional comparison format.

The system allows for use of a LOFT approach to personality assessment via forced-choice questionnaires.

In summary, key aspects of the test specifications are broadly as follows:

Instrument format:
  Forced-choice
  Multidimensional triplets (Each item measures one scale; each triplet combines three items measuring three different scales.)
  Complete ranking (e.g. Respondent select item 'most like me' and item 'least like me'.)
Administration format:
  Dynamic item selection from item bank
  Potentially computer adaptive
Measurement model:
  Dominance Thurstonian IRT Key elements of the system will now be described in further detail.

Components of system make use of the following variables:

| Variable | Format | Location | Content |
|---|---|---|---|
| d | Scalar (1x1) | Content bank | Number of scales in content bank. |
| SCALE | Vector (dx1) | Content bank | Array of scale IDs. |
| COR | Matrix (dxd) | Content bank | Correlation matrix for the d scales. |
| SELECT | Vector (dx1) | Test planner | Vector indicating scale selected for measurement (0 = not selected, 1 = selected). |
| TI | Vector (dx1) | Test planner | Vector of target accuracy level (information) by scale. |
| PLAN | Matrix (3 columns) | Test planner | Fixed scale selection plan for content balancing. Each row contains three scale IDs. Could be completely defined, defined for part of the test (possibly the beginning), or completely empty. |
| $M_{min}$ | Scalar (1x1) | Test planner | Minimum number of triplets required or allowed in test. |
| $M_{max}$ | Scalar (1x1) | Test planner | Maximum number of triplets required or allowed in test. |
| $N_{min}$ | Scalar (1x1) | Test planner | Minimum number of triplets required or allowed per scale. |
| $N_{max}$ | Scalar (1x1) | Test planner | Maximum number of triplets required or allowed per scale. |
| $U_{max}$ | Scalar (1x1) | Test planner | Maximum number of times an item can be used. |
| $R_{min}$ | Scalar (1x1) | Test planner | Minimum number of intermediate triplets before an item can be recycled. |
| $D_{max}$ | Scalar (1x1) | Test planner | Maximum social desirability range required or allowed in a triplet. |
| $C_{max}$ | Scalar (1x1) | Test planner | Maximum absolute scale correlation required or allowed in a triplet. |
| $I_{min}$ | Scalar (1x1) | Test planner | Minimum total information required or allowed from a triplet. |

-continued

| Variable | Format | Location | Content |
|---|---|---|---|
| $K_0$ | Vector (4x1) | Test planner | $(K_{01}, K_{02}, K_{03}, K_{04})$, target proportion of triplets with each of the item keyed direction combinations (+++, ++−, +−−, −−−). |
| CAT | Scalar (1x1) | Test planner | Compute Adaptive Testing switch (1 = CAT, 0 = LOFT). |
| NADMIN | Vector (dx1) | Test generator | Test generation process variable: number of items administered so far (including repeats, by scale). |
| NAVAIL | Vector (dx1) | Test generator | Test generation process variable: number of items available for selection (by scale). |
| STATUS | Vector (dx1) | Test generator | Test generation process variable: vector indicating scale status (0 = inactive in test, 0.5 = initially active in test but currently inactive, 1 = available for selection; alternatively, 0 = inactive, 1 = available for selection). Initially, ACTIVE or STATUS = SELECT |
| CI | Vector (dx1) | Test generator | Test generation process variable: vector of current test information (prior information plus test information obtained so far) by scale. |
| II | Vector (3x1) | Test generator | Test generation process variable: vector of information from triplet being constructed for the three selected scales. |
| $\theta_0$ | Vector (dx1) | Test generator | Starting theta values for scales being measured. |
| $\theta$ | Vector (dx1) | Test generator | Test generation process variable: current theta values for scales being measured. |
| TEST | Matrix (3 columns) | Test generator | Test generation process variable: matrix for recording test constructed. Each row contains three items forming a triplet. Would normally be empty at the beginning of the test unless it is a retest session. |
| n | Scalar (1x1) | Test generator | Test generation process variable: loop count. |
| M | Scalar (1x1) | Test generator | Test generation process variable: generated triplet count (some loops may return no triplet). |
| K | Vector (4x1) | Test generator | Test generation process variable: $(K_1, K_2, K_3, K_4)$, current sampling probability for each of the item keyed direction combinations (+++, ++−, +−−, −−−). |

Test Construction Engine

Test Construction Engine module 100 comprises Test Planner module 102 and Test generator module 104.

Test Construction Considerations

Balancing contents and ensuring triplet quality are traditionally the preserve of psychologist experience; an alternative is to make use of content constraints and information functions.

| Criteria | Constraints | Rationale |
|---|---|---|
| Content balancing | Pre-defined test plan with fixed scale selections [PLAN] | It is not desirable to have respondents always compare scale A to scale B. Triplets should be selected to cover a reasonably balanced set of scale comparisons. |
| Keyed direction of items | Target proportion of triplets with each of the item keyed direction combinations [$K_0$] | Comparing statements keyed in the same direction (++ or −−) contributes to measuring trait differences. Comparing statements keyed in opposite directions (+−) contributes to measuring trait absolute locations. The aim is to have comparisons of items keyed in the same and in opposite directions. |
| Social desirability | Maximum social desirability range constraint [$D_{max}$] | Statements in the same triplet should have similar social desirability. Note that social desirability is likely to vary with job level/job type. |
| Scale correlations | Maximum absolute correlation constraint [$C_{max}$] | Correlation considerations are taken into account in information calculations. However, generally, it is not desirable to compare scales that are too highly correlated as the comparison then becomes more or less unidimensional. |
| Triplet information | Minimum triplet total information constraint [$I_{min}$] + Information optimisation index for triplet selection | Triplet information depends on item parameters (loading and threshold), scale scores (thetas) and scale correlations. |

Item Keyed Direction Combination Codes

| Code | Item keyed direction (for positive scales) |
| --- | --- |
| 1 | +++ Three positively keyed items. |
| 2 | ++− Two positively keyed items and one negatively keyed item. |
| 3 | +−− One positively keyed item and two negatively keyed items. |
| 4 | −−− Three negatively keyed items. |

Positively keyed items from negative scales work similar to negatively keyed items from positive scales. For some applications it may be desirable for all scales to be positive.

Test Planner

Test planner module 102 collects essential parameters for the test generator. Values of the parameters can be set manually or obtained from job analysis tools (default values in brackets). The configurations should remain the same for all respondents in any particular assessment project where the respondents are applying for/working in the same job.

Scales selected for measurement for the project, select at least 3 [SELECT] (e.g. a standard set of core scales, or a subset of especially relevant scales from all possible scales)
  Target accuracy level (information) by scale [TI] (e.g. all scales measured to the same accuracy level)
  Fixed scale selection plan for content balancing [PLAN]
  Minimum [$M_{min}$] and maximum [$M_{max}$] number of items allowed in test (and, in some embodiments, number or triplets in test, e.g. Min=3 items, Max=10 items, divide by 3 to get number of triplets; alternatively, Minimum [$M_{min}$] and maximum [$M_{max}$] number of triplets allowed in test e.g. Min=3 items, Max=10 items, divide by 3 to get number of triplets)
  Minimum [$N_{min}$] and maximum [$N_{max}$] number of items allowed per scale (e.g. Min=3 items per scale, Max=10 items per scale)
  Maximum number of times an item can be used [$U_{max}$] (e.g. 1)
  Minimum number of intermediate triplets before an item can be recycled [$R_{min}$]
  Maximum social desirability range allowed in a triplet [$D_{max}$]
  Maximum absolute scale correlation allowed in a triplet [$C_{max}$] (e.g. 0.6)
  Minimum total information required or allowed from a triplet [$I_{min}$]
  Target proportion of triplets for each of the item keyed direction combinations [$K_0$] (e.g. (0.5, 0.5, 0, 0), might depend on number of traits measured)
  Computer Adaptive Testing switch [CAT] (e.g. 1)
  Information Optimisation Index selection Test configuration parameters such as the number of and specific selection of scales, and the duration of test may be specified by an external source such as a requirements generator.

Test Generator

Test generator module 104 generates tests based on configurations received from the test planner module 102 and on additional candidate-specific settings (default values in brackets):

Initial theta [$\theta_0$] (0 for all scales)
  Test seen so far [TEST] (empty)
  Note that unless it is a retest session following some initial test, all candidates should start at the same $\theta_0$ and TEST should be empty.

Generally, candidate specific characteristics (based on previous test or other background information) may give an indication of where scores are likely to be and can therefore be used to pre-seed the starting theta values.

Throughout the processes, if CAT is selected, test information will be calculated at the estimated theta scores; otherwise, test information will be calculated at the initial theta values.

Figure 8:
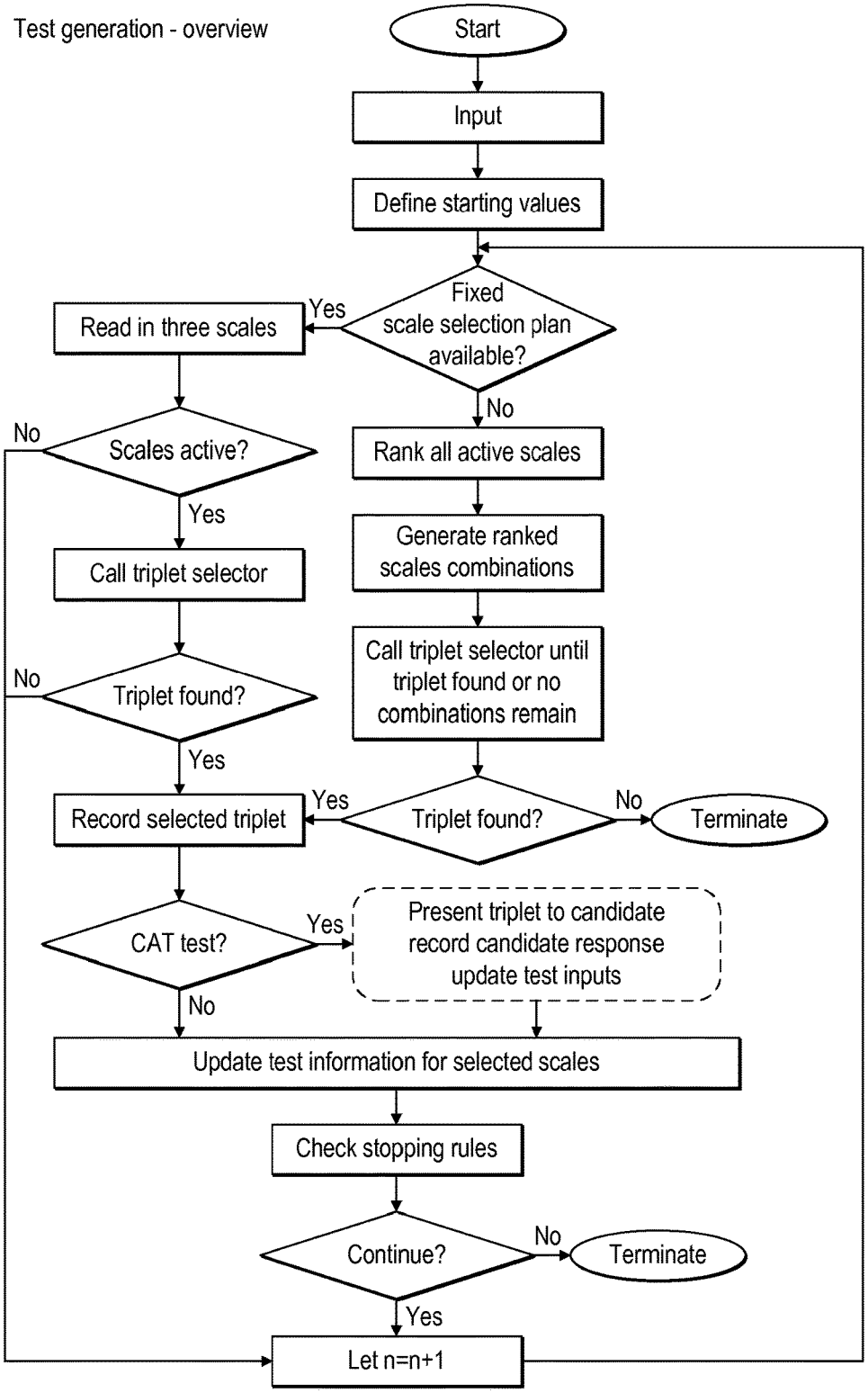
FIGS. 8 and 9 show an example of the test generation process in overview and detail, respectively.
Figure 9:
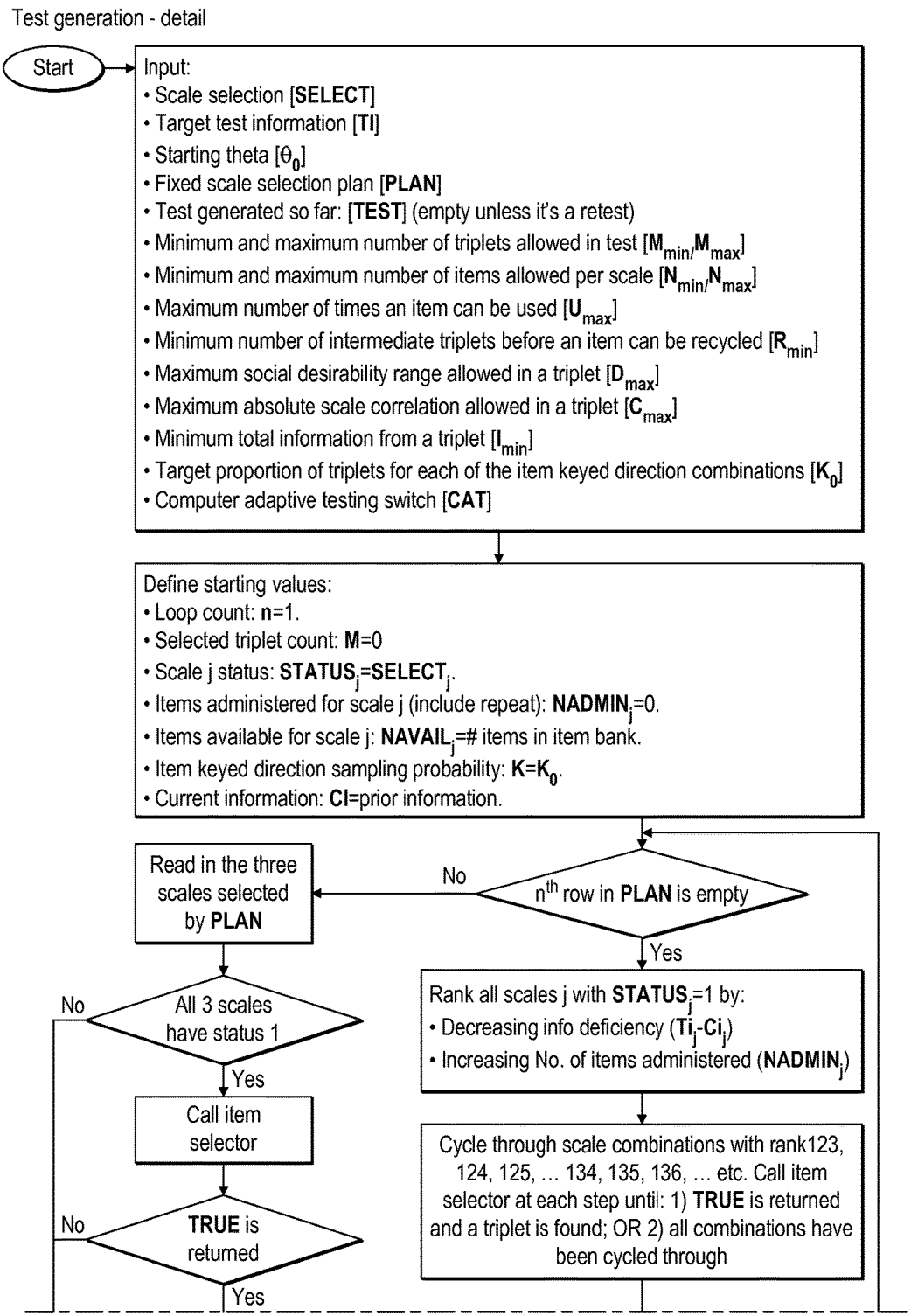
Figure 9:
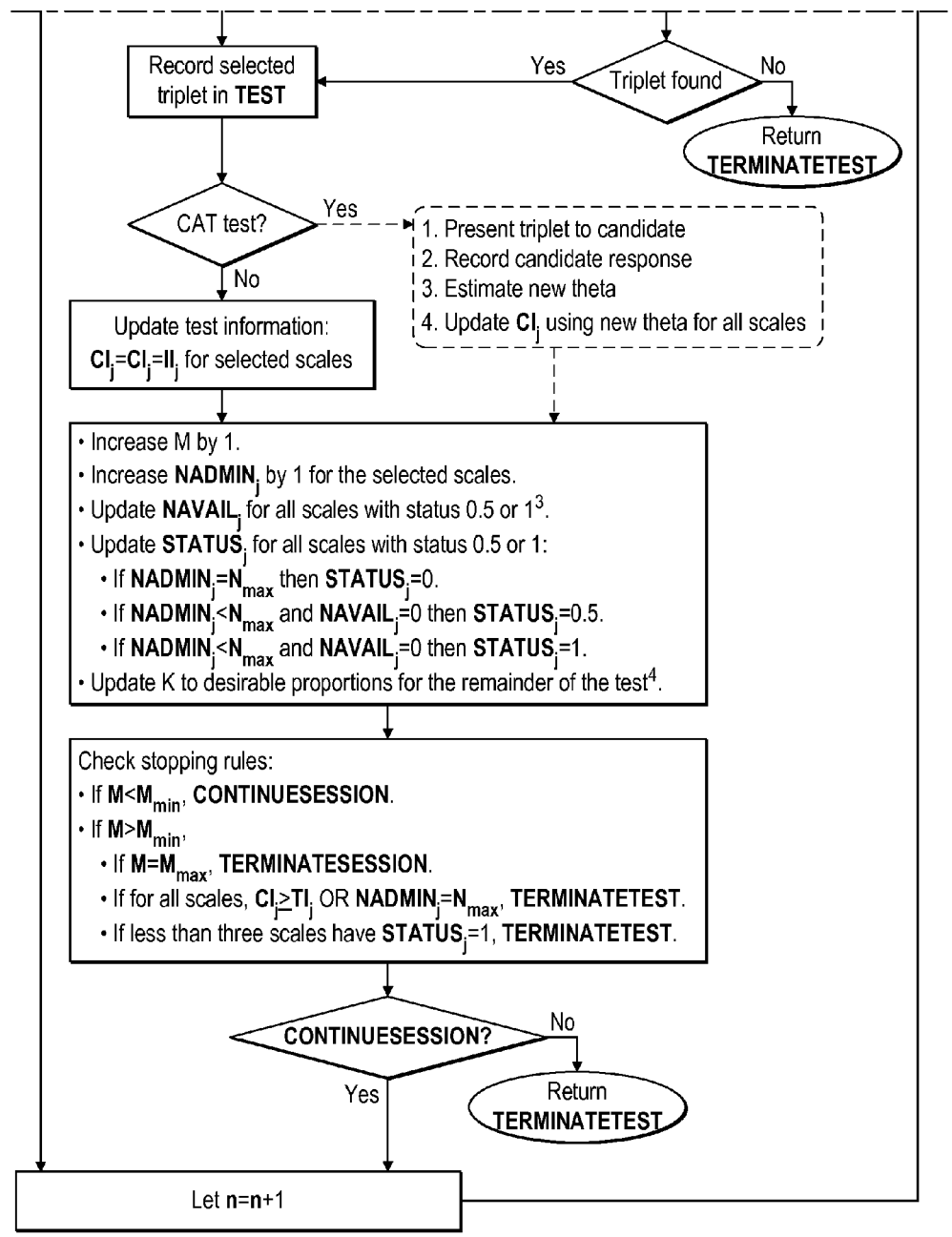

FIGS. 8 and 9 show an example of the test generation process in overview and detail, respectively.

Input of Parameters

The test generator starts with input of parameters and definition of starting values. A selection of possible input parameters includes:

Scale selection [SELECT]
  Target test information [TI]
  Starting theta [$\theta_0$]
  Scale correlations [COR]
  Fixed scale selection plan [PLAN]
  Test generated so far: [TEST] (initialise to be empty, unless the test is a retest, in which case it contains the previously generated test)
  Minimum and maximum number of triplets allowed in test [$M_{min}$, $M_{max}$]
  Minimum and maximum number of items allowed per scale [$N_{min}$, $N_{max}$]
  Maximum number of times an item can be used [$U_{max}$]
  Minimum number of intermediate triplets before an item can be recycled [$R_{min}$]
  Maximum social desirability range allowed in a triplet [$D_{max}$]
  Maximum absolute scale correlation allowed in a triplet [$C_{max}$]
  Minimum total information required from a triplet [$I_{min}$]
  Target proportion of triplets for each of the item keyed direction combinations [$K_0$]
  Computer Adaptive Testing switch [CAT]

Input parameters may be pre-determined or may be user-defined.

The scale correlations [COR] are based on theoretical constructs and data obtained from a sample population. In more detail, an initial model of the constructs is validated by the actual data or modified to fit the actual data until a good model is defined for the underlying construct (i.e. what the scales are) and the covariance structure (i.e. how the scales correlate with each other). The correlations are embedded in many of the calculations (including information from a triplet/the test and estimation of theta scores) as well as used in relation to $C_{max}$.

Regarding the social desirability, if subjects are influenced in their choices by the perceived social desirability of the items, then this can be detrimental to the quality of the assessment results. Therefore it is undesirable for the items in a triplet to have too large a social desirability range. The following is a simplistic set of items with differing social desirability values:

A. I am a very good person (social desirability=2)
  B. I am a good person (social desirability=1)
  C. I am a friendly person (social desirability=1)
  D. I am a kind person (social desirability=1)
  E. I am a bad person (social desirability=−1)

To make triplets robust to social desirability responding, the pairing of items is discouraged or avoided if the difference between their social desirability values is greater that a threshold value $D_{max}$. If for the items listed above the threshold is $D_{max}=0.5$, then the table below shows the evaluation of the social desirability range for some exemplary combinations of items:

| Triplet | Social desirability values | Social desirability range | Dmax threshold satisfied? |
|---|---|---|---|
| A/B/C | 2/1/1 | 2 − 1 = 1 | No |
| B/C/D | 1/1/1 | 1 − 1 = 0 | Yes |
| C/D/E | 1/1/−1 | 1 − (−1) = 2 | No |
| A/B/E | 2/1/−1 | 2 − (−1) = 3 | No |

The social desirability values of items may depend on the context of the assessment. Social desirability may be specific to certain job roles, for example it may be highly desirable for a waiter to be personable, while it may be more desirable for a crime reduction officer to be assertive. The $D_{max}$ threshold may depend on factors such as the range of social desirability in the item bank, the number of items available, and other factors that determine the balance between limitation of available items and test quality.

Define Starting Values

A selection of possible starting value definitions includes:

Loop count: n=1.

Selected triplet count: M=0.

Scale j status: $STATUS_j=SELECT_j$.

Items administered for scale j (include repeat): $NADMIN_j=0$.

Items available for scale j: $NAVAIL_j$=number of items in item bank for scale j.

Item keyed direction sampling probability: $K=K_0$.

Current information: CI=information available prior to test construction.

Regarding test information, each additional question (triplet) provides some information (II) as to where the subject lies (θ) on the scales measured by the particular triplet; previous questions also provide information (CI) on the scales being measured. The current triplet information (II) contributes accumulatively to the existing test information (CI). The current triplet information (II) depends on item properties, scale covariance structure (and hence on other items in the triplet and their scale correlations, as the evaluation is based on comparative judgement modelling) and candidate theta scores. For CAT, candidate theta score estimates are updated during a test session and feed into the calculation of information (both CI and II); for LOFT, no scoring is performed during the test and the theta of subject is assumed to be average (θ=0). The exact formulae are described in more detail in the recent academic papers cited above.

In some embodiments, the current triplet information (II) may be more relevant for CAT, less for LOFT; for LOFT no scoring is performed during the test and the theta of subject is assumed to be average (θ=0).

Target test information (TI) represents the ideal target measurement accuracy to be achieved by the end of the test session. Useful information on the candidate may come from the test session, and may also come from prior knowledge about the candidate and/or about the population to which the candidate belongs. In other words:

Total information=Prior information+Test Session information and one of the measurement aims during test construction is to optimise total information to achieve target test information (TI).

In some embodiments, Target test information (TI) may represent the amount of information intended to be gained to achieve the ideal target measurement accuracy of the test session. This may include prior knowledge (what is already known about the candidate/population), where:

Prior information+information from session=target test information.

The specific IRT model and IRT information are intimately tied together; IRT information represents how much information would be gleaned from the test if the candidate behaved according to the response process described by the IRT model. It is also used here, in some embodiments, to influence how the triplets are generated.

As the test progresses, Current information (CI) will tend to Target test information (TI) as information increases with each question. The IRT model is such that even conflicting responses are modelled properly and measurement accuracy improves as the test progresses.

Studying the response patterns or tracking the evolution of theta scores in one or across several tests can flag up inconsistent behaviour of a subject, potentially detecting random responding and/or fraud.

Regarding keyed direction of items, for two positive scales:

comparison of two items keyed in the same direction (+/+ or −/−) contributes to measuring the difference between the two theta scores comparison of two items keyed in opposite directions (+/−) contributes to measuring the sum of the two theta scores.

Both types of comparisons are required to accurately recover relative theta differences and absolute theta locations. Therefore at triplet level, a proportion of triplets ($K_0$) with each of the item keyed direction combinations (+++, ++−, +−−, −−−) may be used. Positively/negatively keyed items from negative scales work similar to negatively/positively keyed items from positive scales.

Given the input parameters and starting values, the test generator begins generating the test.

Check for Fixed-Scale Selection Plan

The test generator first checks if a fixed scale selection plan [PLAN] is available. A fixed scale selection plan defines the sequence of the scale combinations that are to be tested. In the fixed scale selection plan a or each row defines a combination of three scales. If the row is empty, there is no plan available.

If Fixed-Scale Selection Plan Exists

Read in Three Scales

If a fixed scale selection plan defines a combination of three scales, the next step is to read in the three selected scales that are specified in the current row of the plan. It is possible that only some rows of the plan are populated and other rows are empty; for example only the first few rows of the plan may be populated.

Check Scales are Active

Once the three selected scales have been read in, they are checked to ensure that the selected scales are active scales (a scale j is active if STATUSj=1). If the input parameters include a selection of scales [SELECT] for measurement (in which case the non-selected scales would be flagged as inactive), then this step prevents the inclusion of inappropriate scales in the test. Moreover, particularly towards the end of the test, some selected scales would have already reached the target measurement accuracy and/or the maximum number of items allowed, and would no longer be flagged as active. Then this step prevents the compromise of the test due to inappropriate planning. If any of the three scales is not active, then the test generator returns to the beginning to check the next row in PLAN, or, say, of the test generation for a new set. If all three scales are active, the test generator proceeds to the triplet selector.

Select Triplets

The triplet selector (described in further detail below) selects a triplet of items for the three scales. The triplet selector may fail to identify a suitable triplet, in which case the triplet selector returns FALSE and the test generator returns to the beginning to check the next row in PLAN, or, say, of the test generation for a new set. If the triplet selector successfully identifies a suitable triplet, it returns TRUE and the identified items in the suitable triplet. The selected triplet is then recorded in the test being generated [TEST].

OR if Fixed-Scale Selection Plan does NOT Exist

Rank Scales

Returning to the test generator checking if a fixed scale selection plan [PLAN] is available, if no fixed scale selection plan is available, then the test generator proceeds to select scales. In this case the test generator ranks all the scales that are active. The available (active) scales can be ranked according to a variety of measures, for example:

Decreasing IRT information deficiency ($TI_j - CI_j$)
Increasing number of items administered ($NADMIN_j$)

FIG. 10 shows an example of scale ranking according to both 'information deficiency' 802 and 'item usage' 804.

In the illustrated example, 10 scales 800 are included for the test being generated. Each scale has a scale selectable status 820 which indicates if a scale is still available for selection or not. Each scale further has a scale completion status 822 which indicates if a scale has already been completely addressed in the test generated so far. In the example illustrated in FIG. 10, the number of items per scale is capped at 10 items, and the scales that already have 10 items in the test generated so far are labelled as completed.

In the case of ranking according to 'information deficiency' 802, scales 800 are ranked 818 according to an 'information deficiency' value 812, where:

'information deficiency'='target information'−'current information' with

'current information'='prior information'+'test information'.

'Prior information' 808 may be obtained from previous testing sessions and/or known scale distributions of the population. 'Test information' 810 is the information achieved from the test generated so far. The 'Test information' 810 is the sum of all triplet information (II) of triplets already in the test relating to the scale.

In the example illustrated in FIG. 10, 'Target information' 806 is the same for all scales 800. Alternatively, the 'Target information' 806 may be different for different scales, for example, it may be desired to know much about sociability, and only a little about punctuality.

In the case of ranking according to 'item usage' 804, scales 800 are ranked 816 according to the number of items already administered 814 to that scale.

Figure 11:
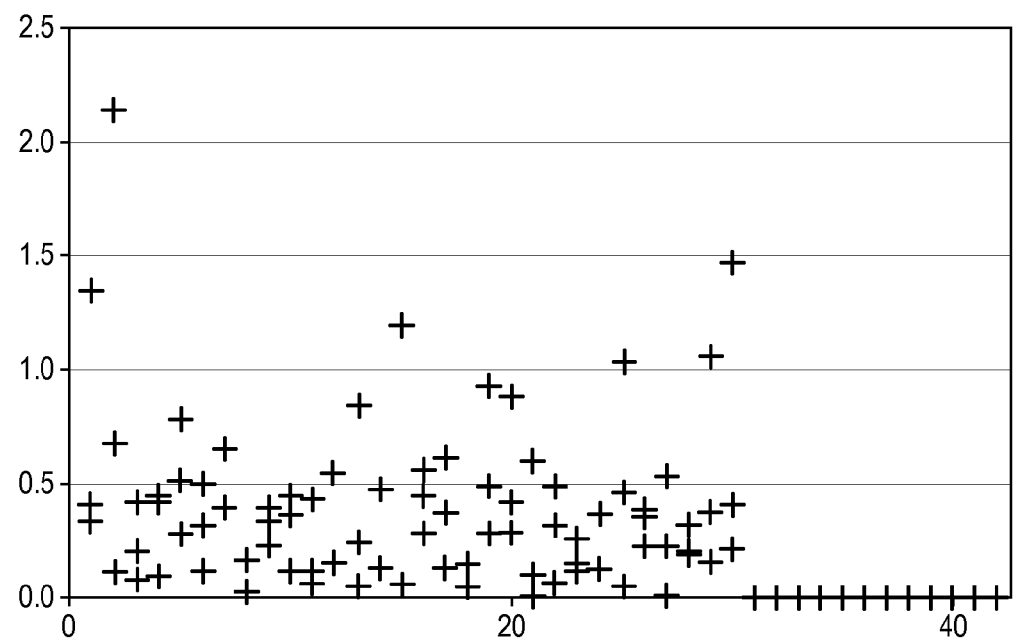
FIGS. 11 and 12 show examples of information metrics.

FIG. 11 shows for a sample test comprising 30 triplets for each triplet the three values of triplet information (one value for each item/scale) that the triplet contributes.

The x-axis represents triplet number, and the y-axis the test i.e. triplet information value.

Figure 12:
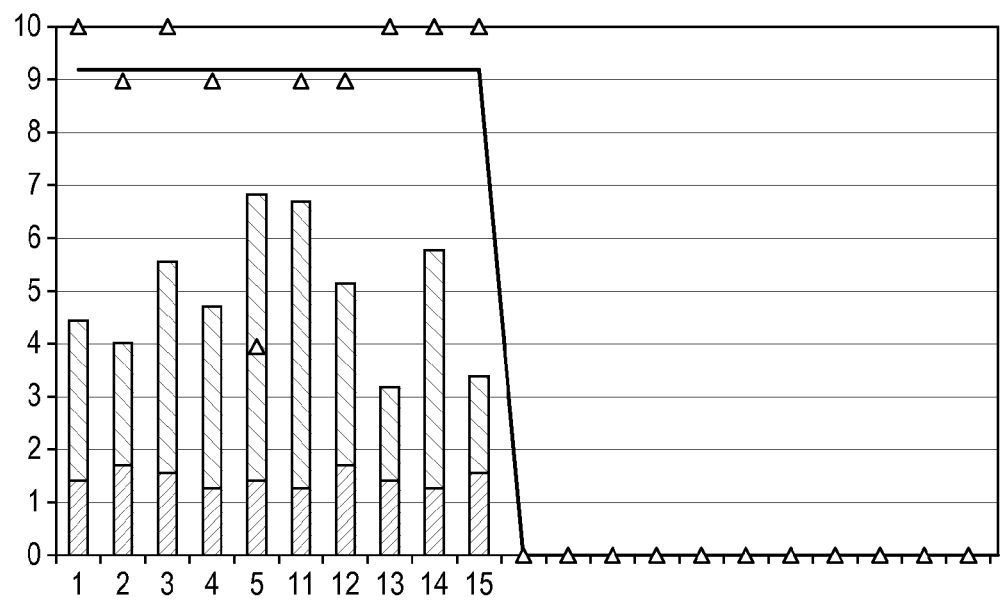

FIG. 12 shows for a sample test comprising 10 or 15 scales for some of the scales the prior information 808 (lower bar), the test information 810 after the last triplet (upper bar), the target information 806 (solid line), and the number of items 814 administered to that scale (triangle symbol). The prior information 808 added to the test information 810 after the last triplet give the total information available at the end of the test regarding the scale. For example scale number 5 has fewer items administered than the other scales, and has a higher total information value at the end of the test than the other scales.

Generate Scale Combinations

Once the available scales are ranked, scale combinations are generated. In the example here, and assuming 6 scales are available with 1 denoting the highest ranking and 6 the lowest ranking, the scale combinations sequence is generated according to the scale rankings in the following order: 123, 124, 125, 126, 134, 135, 136, 145, 146, 156, 234, 235, and so forth.

Select Triplets

Starting with the first scale combination in the sequence, the triplet selector (described in further detail below) attempts to identify a suitable triplet of items; if successful, it returns the triplet; if unsuccessful, triplet selection is attempted for the next scale combination. This continues until either a triplet has been identified, or all combinations have failed to return a triplet. If a triplet is identified, then the selected triplet is then recorded in the test being generated [TEST]. If all combinations of scales fail to return a triplet, then the test generator terminates [TERMINATETEST].

Record Selected Triplets

Check Whether the Test should be Adaptive

Assuming a triplet has been identified and recorded by either route, the next step depends on whether the test is a CAT test or not [CAT].

If CAT, Present Triplet to Candidate and Update Parameters

If the test is a CAT test, then the triplet is presented to the candidate. The candidate's response is recorded, and in dependence on the response the estimate of the theta value is updated.

Given the updated theta values, triplet information (II) and the existing test information (the existing test information being the sum of all triplet information (II) of triplets already in the test) are updated accordingly. Subsequently the current information (CI) is updated for all scales by summing for each scale the existing test information and triplet information (II) from the newly administered triplet.

In some embodiments, given the updated theta value, the triplet information (II) is updated, subsequently the triplet information (II) is added to the existing test information (the existing test information being the sum of all triplet information (II) of triplets already in the test relating to the scale), and finally the current information CI parameter is updated for all scales.

Although CI for all scales would need updating after each response in a CAT session, the impact on CI of scales not being measured by the current triplet is likely to be small, and it may be preferable to update only the scales being measured by the current triplet.

OR if NOT CAT, Update Current Information

If the test being generated is not a CAT test, then the current information (CI) is updated for the selected scales with $CI_j=CI_j+II_j$.

Update System Variables

Next the values of some test generation parameters are updated, in the illustrated example as follows:

Increase M by 1.

Increase $NADMIN_j$ by 1 for the selected scales.

Update $NAVAIL_j$ for all items belonging to scales with status 0.5 or 1. An item is available if:
  Number of times item used $<U_{max}$
  Item not used in the last $R_{min}$ triplets Update STATUS for all scales with status 0.5 or 1:
  If $NADMIN_j=N_{max}$ then $STATUS_j=0$.
  If $NADMIN_j<N_{max}$ and $NAVAIL_j=0$ then $STATUS_j=0.5$.
  If $NADMIN_j<N_{max}$ and $NAVAIL_j>0$ then $STATUS_j=1$.

Update K to desirable proportions for the remainder of the test.

Regarding update K, the desirable item keyed direction proportions for remainder of test:
  (i) Target proportion of triplets with each of the item keyed direction combinations: $K_0=(K_{01}, K_{02}, K_{03}, K_{04})$
  (ii) So the expected numbers of triplets with each of the item keyed direction combinations are: $M_{max}*(K_{01}, K_{02}, K_{03}, K_{04})$
  (iii) Suppose $X=(X_1, X_2, X_3, X_4)$ triplets have been administered for each of the item keyed direction combinations, then for the remainder of the test we set: $K=(K_1, K_2, K_3, K_4)$ with $K_i$ proportional to max $(M_{max}*K_{0i}-X_i, 0)$.

Check Stopping Rules

Once the parameters have been updated, the stopping rules are checked to determine if the test generation is to be continued or terminated. In the illustrated example the stopping rules are:

If $M<M_{min}$ CONTINUESESSION
if $M \geq M_{min}$
  if $M=M_{max}$, TERMINATETEST
  if for all scales, $CI_j \geq TI_j$ OR $NADMIN_j=N_{max}$, TERMINATETEST
  If less than three scales have $STATUS_j=1$, TERMINATETEST stopping rules may also be used.

Check Whether Test Generation has Terminated

If the test generation process has not terminated, then the test generator returns to the beginning of the test generation to check the next row in PLAN for generating the next triplet, or, say, for a new set.

Triplet Selector

Figure 13:
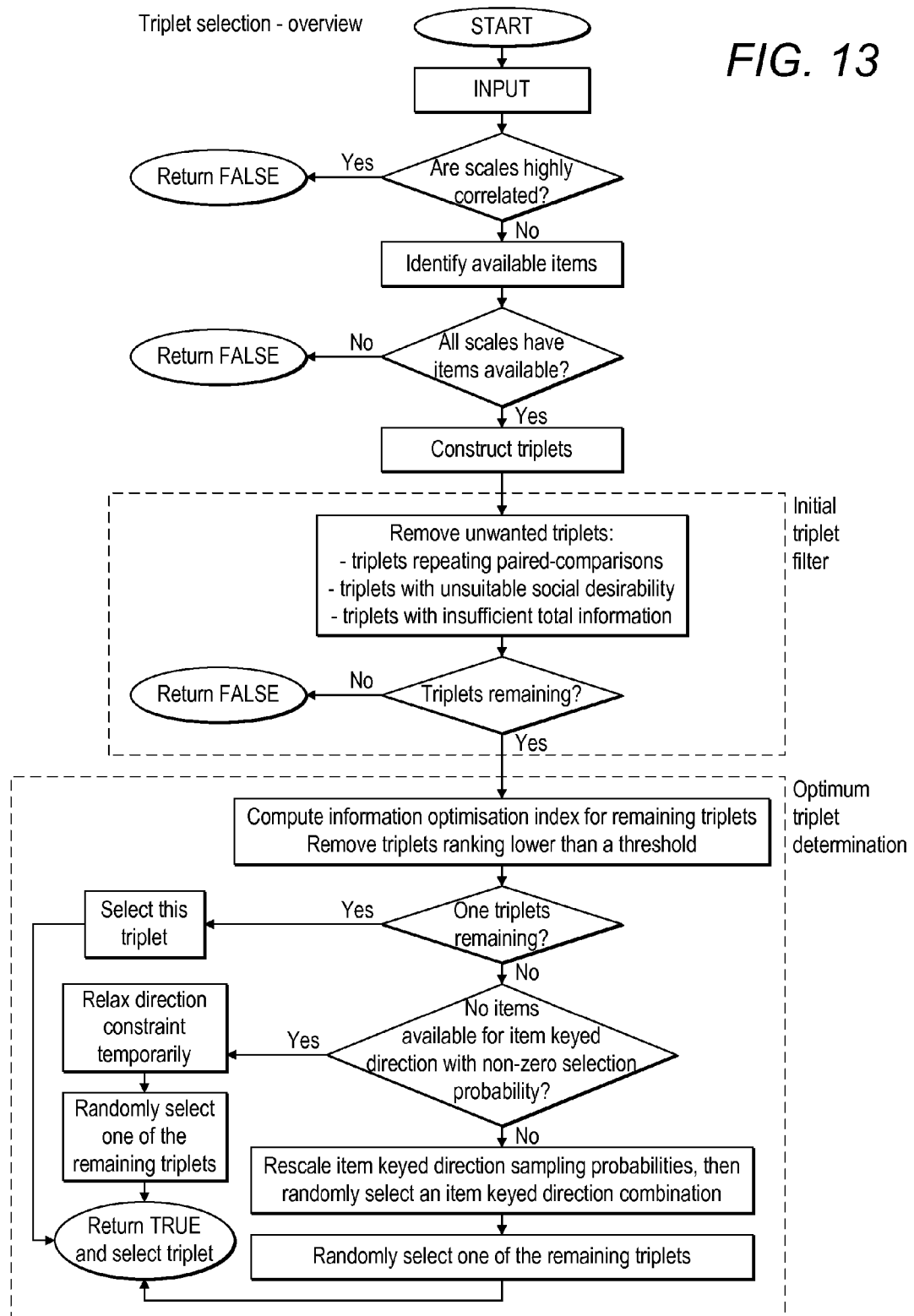
FIGS. 13 and 14 show the triplet selection process in overview and detail, respectively.
Figure 14:
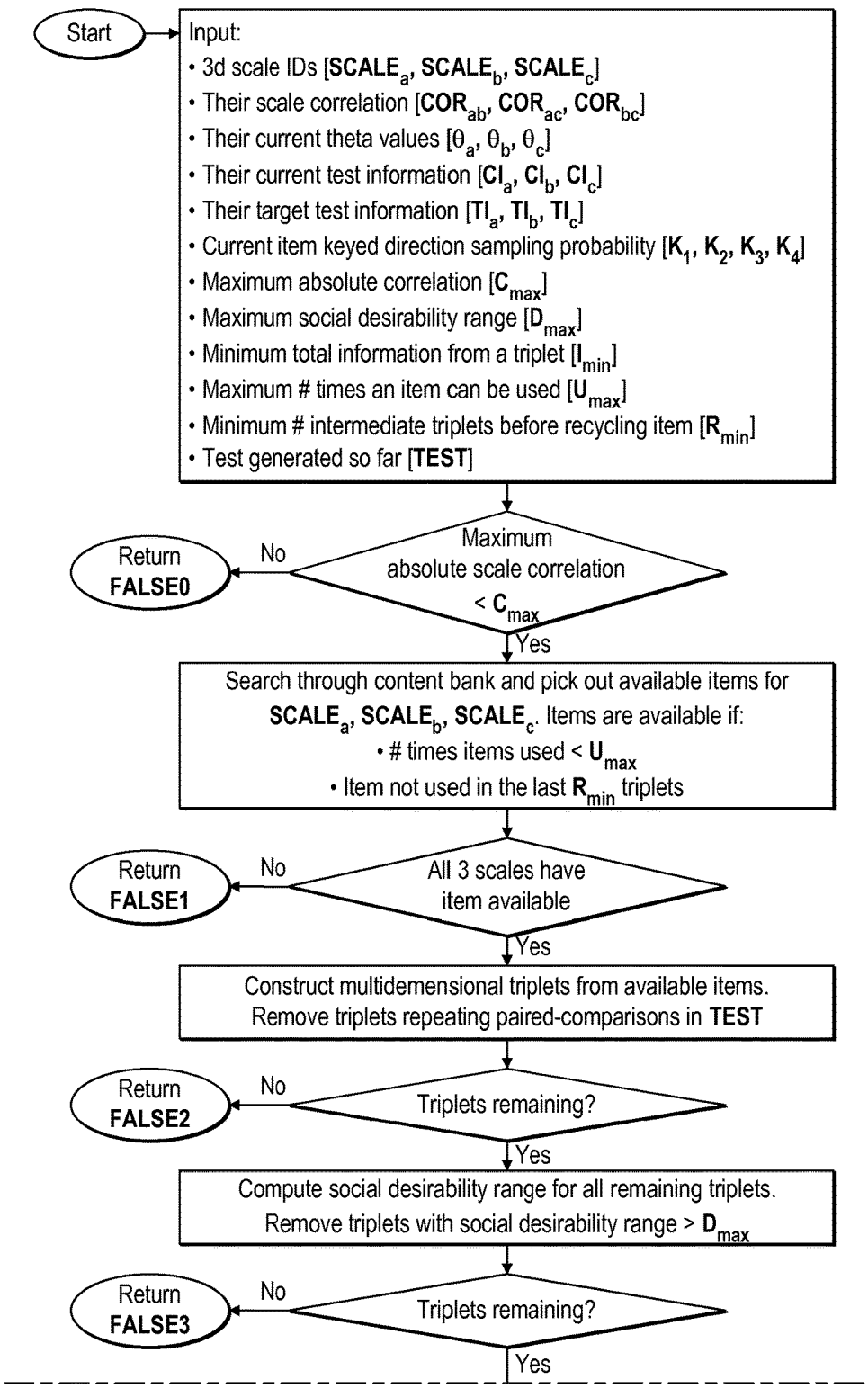
Figure 14:
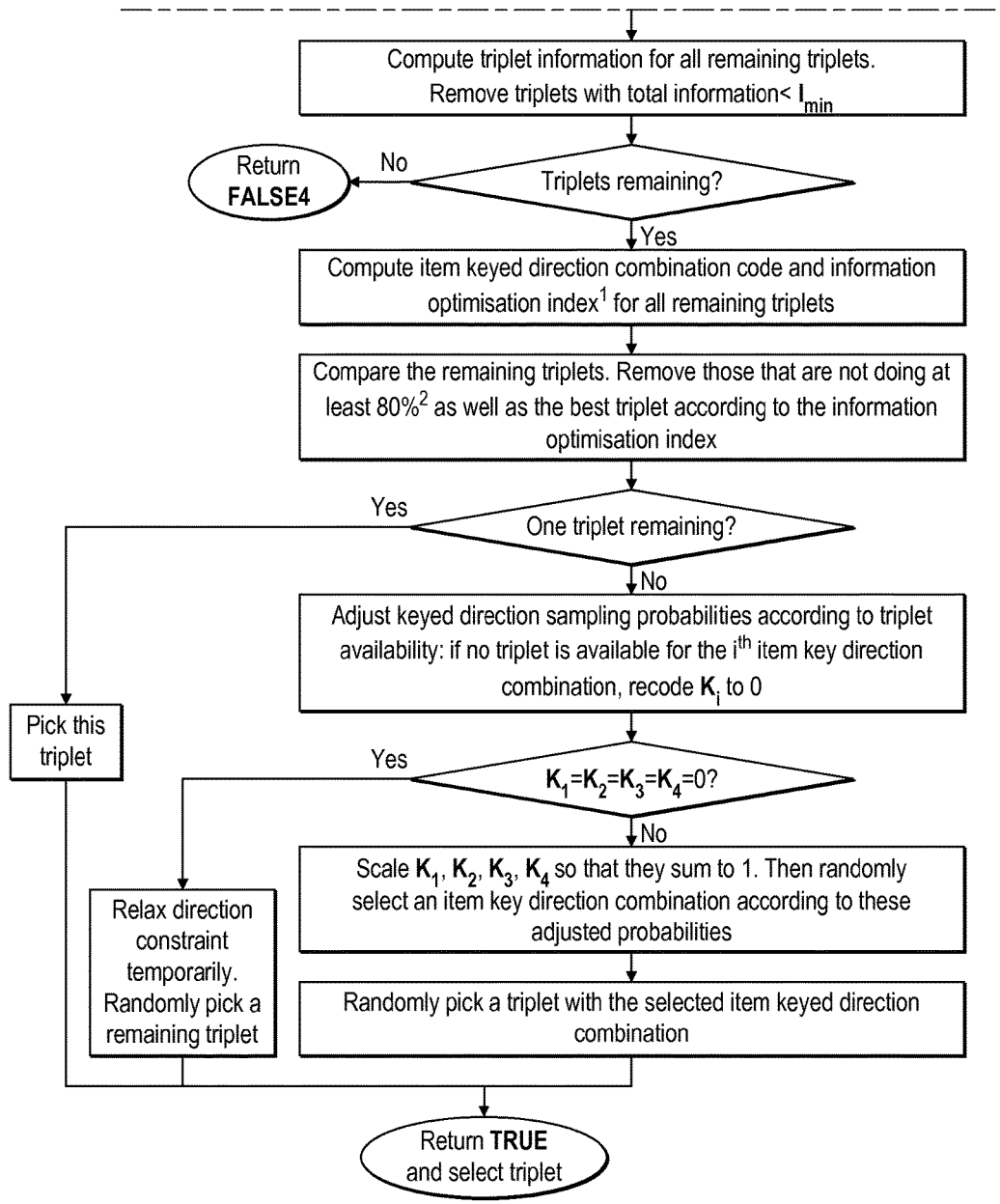

FIGS. 13 and 14 show the triplet selection process (as performed by the triplet selector 105) in overview and detail, respectively.

Input of Parameters

The triplet selector 105 is called by the test generator and passed at least some of the following arguments:
  3 scale IDs [$SCALE_a$, $SCALE_b$, $SCALE_c$]
  Their scale correlations [$COR_{ab}$, $COR_{ac}$, $COR_{bc}$]
  Their current theta values [$\theta_a$, $\theta_b$, $\theta_c$]
  Their current information [$CI_a$, $CI_b$, $CI_c$]
  Their target information [$TI_a$, $TI_b$, $TI_c$]
  Current item keyed direction sampling probability [$K_1, K_2, K_3, K_4$]
  Maximum absolute correlation [$C_{max}$]
  Maximum social desirability range [$D_{max}$]
  Minimum total information from triplet [$I_{min}$]
  Maximum number of times an item can be used [$U_{max}$]
  Minimum number of intermediate triplets before recycling item [$R_{min}$]
  Test generated so far [TEST]

Check if Scales are Highly Correlated

If triplets were constructed from highly correlated scales (representing highly correlated traits such as sociability and friendliness) it would be easier for subjects to bias their response to what they think may be 'right' or more desirable to the purpose of the test, than if the scales are not as highly correlated (representing less correlated traits such as sociability and analytical thinking). The allowed correlation value range or allowable correlation between the scales is set according to a maximum absolute correlation limit $C_{max}$.

Identify Available Items

Search through content bank and pick out available items for $SCALE_a$, $SCALE_b$, $SCALE_c$. Items are available if:
  number of times item used $<U_{max}$
  Item not used in the last $R_{min}$ triplets Construct Triplets If all three scales have items available, multidimensional triplets are constructed from the available items.

In order to return a (most) suitable triplet to the test generator, a two-stage process is employed.

Initial Triplet Filter/Removal of Unwanted Triplets

Various triplet filter steps may be used, for example:
  Removal of triplets repeating paired-comparisons in TEST.
  Removal of triplets with social desirability range $>D_{max}$
  Removal of triplets with total information $<I_{min}$.

Typically, the filters are applied in sequence in the above order. Alternatively, the filters may be applied in any order, with some orders being computationally more efficient than others in some applications Regarding social desirability, the degree to which this can be taken into account when assembling a triplet depends on the context. The baseline social desirability may vary depending on job context, culture, age group, etc. and may be set by further parameters.

In some embodiments, a crude information check, such as one using a minimum total information constraint $I_{min}$, may be used to eliminate certain, say suboptimal, triplets. Each triplet provides three pieces of information, one for each related scale. Discounting those triplets with excessively low total information reduces the number of triplets requiring consideration in the optimisation stage later, and hence saves computation time. It also provides a rough standard or threshold on triplet quality and avoids construction of triplets with unacceptably low information gain. Alternatively, instead of imposing a standard on the value of the total triplet information, a filtering standard may be imposed on the value of the information optimisation index. In some embodiments, instead of removing triplets with total information $<I_{min}$, triplets with information optimisation index $<I_{min}$ are removed.

Optimum Triplet Determination

Once the initial triplet filter has been applied, the optimisation may begin. The optimum triplets are those which when processed by the candidate will yield the maximum amount of information about the candidate. Ideally, the optimum triplets would contribute most to areas where there is least information about the subject. The aim is to have an efficient test which is as short as possible.

Each triplet provides three pieces of IRT information, one for each of the scales being measured. In order to compare the effectiveness of different triplets, the general principle is to transform these three pieces of information in the 3-dimensional information space into a single optimisation index on a 1-dimensional scale. Each triplet can then be ranked by potential information gain according to the optimisation index. Examples of possible information optimisation indices are discussed in further detail below.

An example of a typical optimum triplet determination process is as follows:
Compute item keyed direction combination code and information optimisation index for all remaining triplets.
Compare the remaining triplets.
Remove those that are not doing at least, typically, 80% as well as the best triplet according to the information optimisation index. The figure of 80% may be adjustable.
If one triplet remains, pick this triplet.
else
Adjust keyed direction sampling probabilities according to triplet availability: if no triplet is available for the $i^{th}$ item key direction combination, recode $K_I$ to 0.
If $K_1=K_2=K_3=K_4=0$, Relax keyed direction constraint temporarily and randomly pick a remaining triplet.
else
Scale $K_1$, $K_2$, $K_3$, $K_4$ so they sum to 1 and randomly select an item keyed direction combination according to these adjusted probabilities. Then randomly pick a triplet with the selected item keyed direction combination.
Return TRUE and selected triplet
This optimum triplet determination process is illustrated in the case of a simple test of 15 triplets and measuring 10 scales, with different scenarios as follows.

A proportion of {++} pairs and a proportion of {+−} pairs are desired so that trait differences and trait locations are covered. As discussed above {−+} pairs essentially work as {+−} pairs and enable recovery of the trait sum; {−−} pairs essentially work as {++} pairs and enable recovery of the trait difference.

The following table lists the break down of triplets into pairs, and the keyed direction sampling probabilities ($K_0$) necessary to generate the desired proportions of pairs (other proportions than those shown here may be used):

| Triplet keyed direction | Pair keyed direction | $K_0$ | Expected number of triplets out of 15 triplets | Overall pair keyed direction count |
|---|---|---|---|---|
| +++ | ++<br>++<br>++ | 1/3 | 5 | 15 ++ pairs |
| ++− | ++<br>+−<br>+− | 2/3 | 10 | 10 ++ pairs,<br>20 +− pairs |
| +−− | +−<br>+−<br>−− | 0 | 0 | |
| −−− | −−<br>−−<br>−− | 0 | 0 | |

According to the above table the test construction engine aims to pick 5+++ triplets and 10++− triplets, giving 25++ pairs and 20+− pairs.

Starting with the first triplet (with no update from previous test generation and hence $K=K_0$), and assuming that there are items available for all triplet keyed directions so no adjustment to K is needed the triplet determination process selects triplets as follows:

1. Randomly select an item keyed direction combination according to K (i.e. the probability of picking +++ is 1/3 and ++− is 2/3). In the example illustrated here ++− is selected.
2. Within the selected item keyed direction combination, randomly pick any good triplet (i.e. triplets passing through all content constraints and measurement optimisation filters). The table below lists the numbers of suitable triplets for the different item keyed direction combinations for the first triplet (with given scales). Given the selection made in step 1 above, one of the 20 triplets with ++− is selected at random.

| Triplet keyed direction | Available good triplets count | K | Adjusted K | Scaled adjusted K |
|---|---|---|---|---|
| +++ | 30 | 1/3 | 1/3 | 1/3 |
| ++− | 20 | 2/3 | 2/3 | 2/3 |
| +−− | 50 | 0 | 0 | 0 |
| −−− | 40 | 0 | 0 | 0 |

Continuing with the second triplet, now there is already a ++− triplet in the test, hence the sampling probabilities are updated as follows:

| Triplet keyed direction | $K_0$ | Expected number of triplets out of 15 triplets | Selected number of triplets with this combination | Expected number of triplets for rest of test | K |
|---|---|---|---|---|---|
| +++ | 1/3 | 5 | 0 | 5 | 5/14 |
| ++− | 2/3 | 10 | 1 | 9 | 9/14 |
| +−− | 0 | 0 | 0 | 0 | 0 |
| −−− | 0 | 0 | 0 | 0 | 0 |

The table below lists suitable triplets for the different item keyed direction combinations for the second triplet (with given scales, the scales being different from those in (or than for) the first triplet). The selection process is similar as for the first triplet. In the example shown here, there happen to be no ++− items, therefore K is adjusted (to 0 for ++−) and rescaled to sum to 1 (for the remaining item keyed direction combinations). The triplet selection resumes after the rescaling. Here, +++(with probability 1) is selected, and one of the 10 triplets is selected at random.

| Triplet keyed direction | Available good triplets count | K | Adjusted K | Scaled adjusted K |
|---|---|---|---|---|
| +++ | 10 | 5/14 | 5/14 | 1 |
| ++− | 0 | 9/14 | 0 | 0 |
| +−− | 20 | 0 | 0 | 0 |
| −−− | 40 | 0 | 0 | 0 |

Continuing with the third triplet, again, first K is updated:

| Triplet keyed direction | $K_0$ | Expected number of triplets out of 15 triplets | Selected number of triplets with this combination | Expected number of triplets for rest of test | K |
|---|---|---|---|---|---|
| +++ | 1/3 | 5 | 1 | 4 | 4/13 |
| ++− | 2/3 | 10 | 1 | 9 | 9/13 |
| +−− | 0 | 0 | 0 | 0 | 0 |
| −−− | 0 | 0 | 0 | 0 | 0 |

The suitable triplets for the different item keyed direction combinations for the third triplet are evaluated (table below). In this particular example there are no triplets with the desired item keyed direction combinations, so the item direction combination constraint are relaxed and one of the 15+20=35 available triplets is selected at random. In the example here a triplet with +−− is selected.

| Triplet keyed direction | Available good triplets count | K | Adjusted K |
|---|---|---|---|
| +++ | 0 | 4/13 | 0 |
| ++− | 0 | 9/13 | 0 |
| +−− | 15 | 0 | 0 |
| −−− | 20 | 0 | 0 |

Continuing with the fourth triplet K is updated (table below), and the process continues along the same lines as for the first three triplets.

| Triplet keyed direction | $K_0$ | Expected number of triplets out of 15 triplets | Selected number of triplets with this combination | Expected number of triplets for rest of test | K |
|---|---|---|---|---|---|
| +++ | 1/3 | 5 | 1 | 4 | 4/13 |
| ++− | 2/3 | 10 | 1 | 9 | 9/13 |
| +−− | 0 | 0 | 1 | 0 | 0 |
| −−− | 0 | 0 | 0 | 0 | 0 |

The triplet determination process illustrated above is one way of handling item keyed direction combinations, however alternatives are possible. For example, the item keyed direction may be considered by scale (described in more detail below) in stead of by test (as in the illustrated example).

Potential Information Optimisation Indices

Various alternatives may be used for the information optimisation indices. Different indices may be used for different settings, potentially switching indices between different tests and/or during a test.

(i) Maximise Total Information $$II_a + II_b + II_c$$

This is the simplest way of linearizing the three-dimensional triplet information. As this does not consider information deficiency by scale it is not necessarily the best index, but it has the advantage of simplicity.

(ii) Maximise Capped Total Information:

$$\min(CI_a + II_a, TI_a) + \min(CI_b + II_b, TI_b) + \min(CI_a + II_c, TI_c)$$

This is equivalent to minimising total information deficiency.

Once the target information is reached for some scales, it is no longer desirable to improve measurement of these scales. In this case a capped version of index (i) gives priority to scales that have not yet reached their target information, particularly toward the end of the testing process.

Capping the information at the target information level is equivalent to considering information deficiency, i.e. minimising $$\max(TI_a - CI_a - II_a, 0) + \max(TI_b - CI_b - II_b, 0) + \max(TI_c - CI_c - II_c, 0)$$

(iii) Minimise Total Squared Information Deficiency:

$$\max(TI_a - CI_a - II_a, 0)^2 + \max(TI_b - CI_b - II_b, 0)^2 + \max(TI_c - CI_c - II_c, 0)^2$$

This gives priority to larger information deficiencies.

The logic is similar to index (ii), but the information deficiency terms are squared so priorities are given to larger deficiencies.

(iv) Maximise Weighted Total Information:

$$w_a * II_a + w_b * II_b + w_c * II_c$$

(where for example, $w_j = \max(TI_1 - CI_j, 0)$)

The logic is similar to index (i), but some weights are used to assign priorities to some scales over others. Priorities may be given to where information deficiency is higher (giving more weight to larger deficiencies), and/or depend on the purpose of the assessment.

(v) Maximise Product Information:

$$(CI_a + II_a) * (CI_b + II_b) * (CI_c + II_c)$$

This is equivalent to minimising volume of confidence ellipsoid.

The standard error for a scale score is inversely proportional to the square root of information on that scale. So to minimise the volume of the confidence ellipsoid for the three scales in a triplet, we need to maximise the product information.

(vi) Maximise Product Information Capped:

$$\min(CI_a + II_a, TI_a) * \min(CI_b + II_b, TI_b) * \min(CI_c + II_c, TI_c)$$

The logic is similar to index (v), but the information terms are capped as improvements beyond the or our target information is not of interest.

(vii) Other Possibilities

Other possibilities may also be used. In multidimensional IRT-based ability testing different linearizations of the Fisher Information Matrix have been considered. These methods do not use Thurstonian IRT, but their parallels under the Thurstonian IRT model may be developed.

If no triplet is found for a particular scale combination, the triplet selector returns FALSE and may later be recalled by the test generator with a different scale combination.

Alternative Test Generator

Figure 15A:
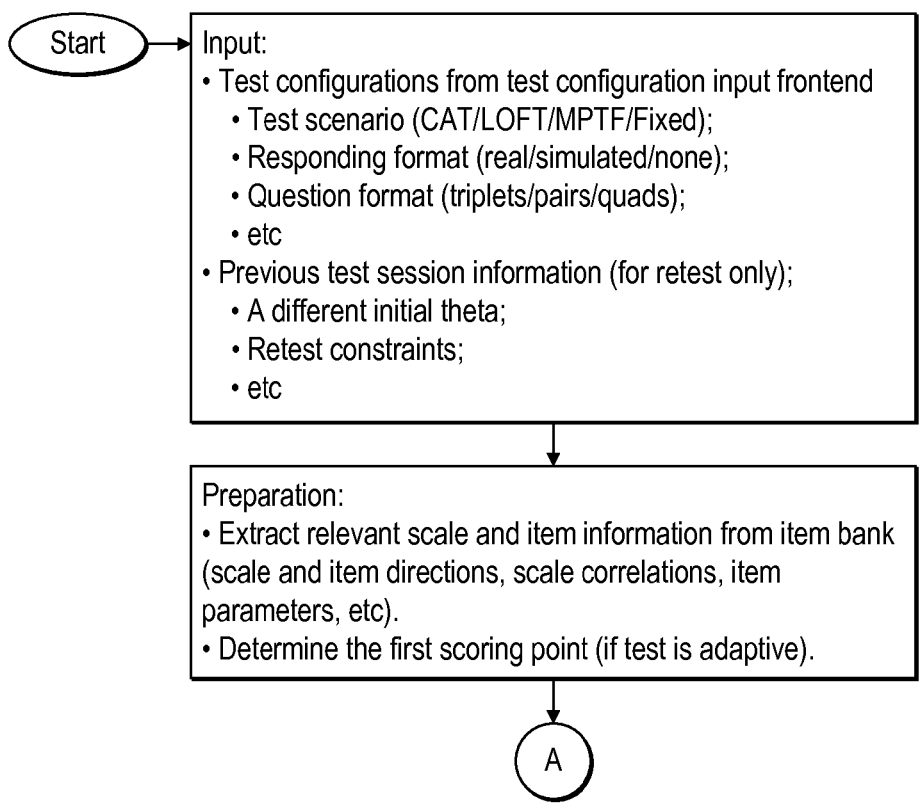
FIGS. 15 (a-c) show another example of the test generation process.
Figure 15B:
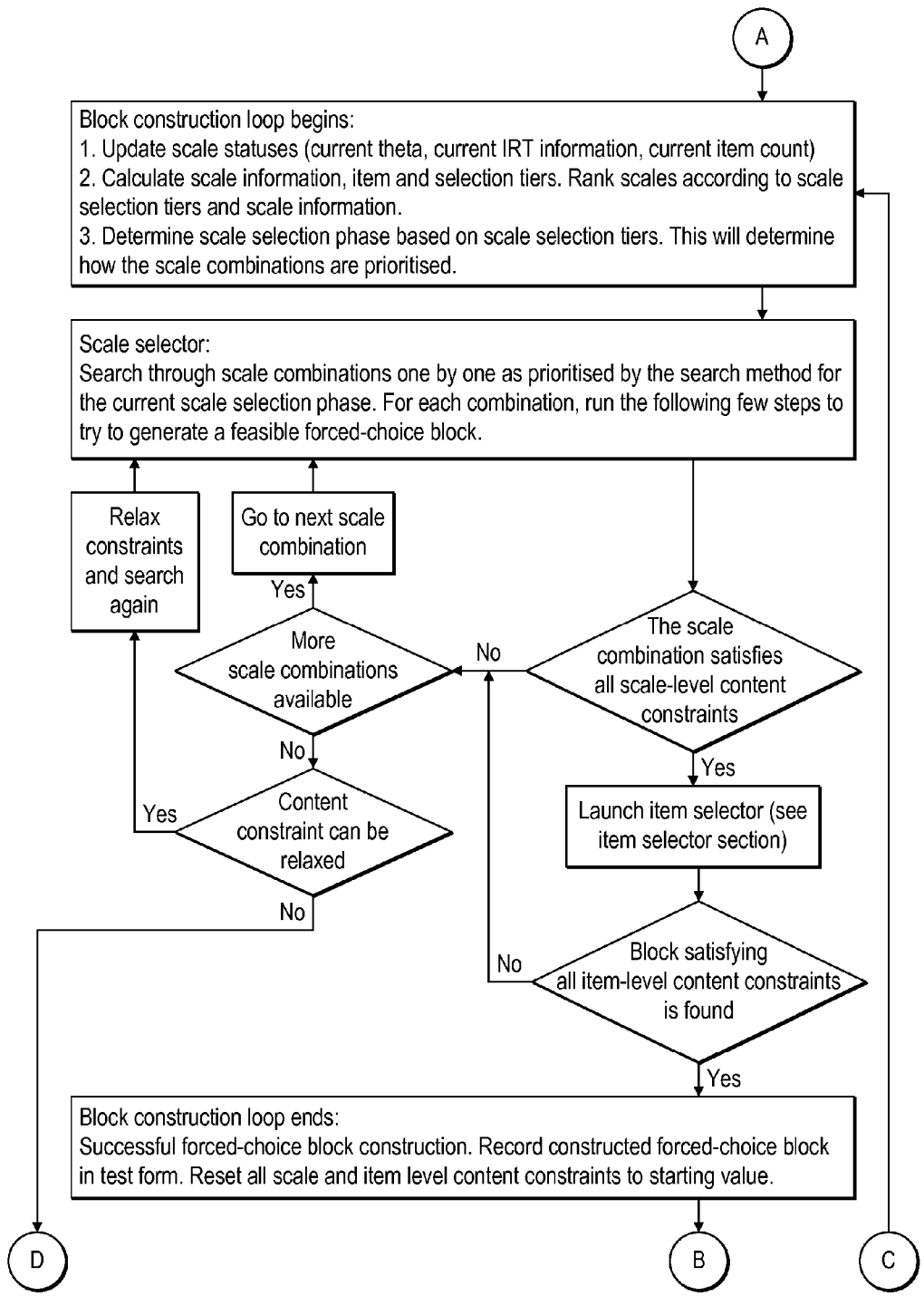
Figure 15C:
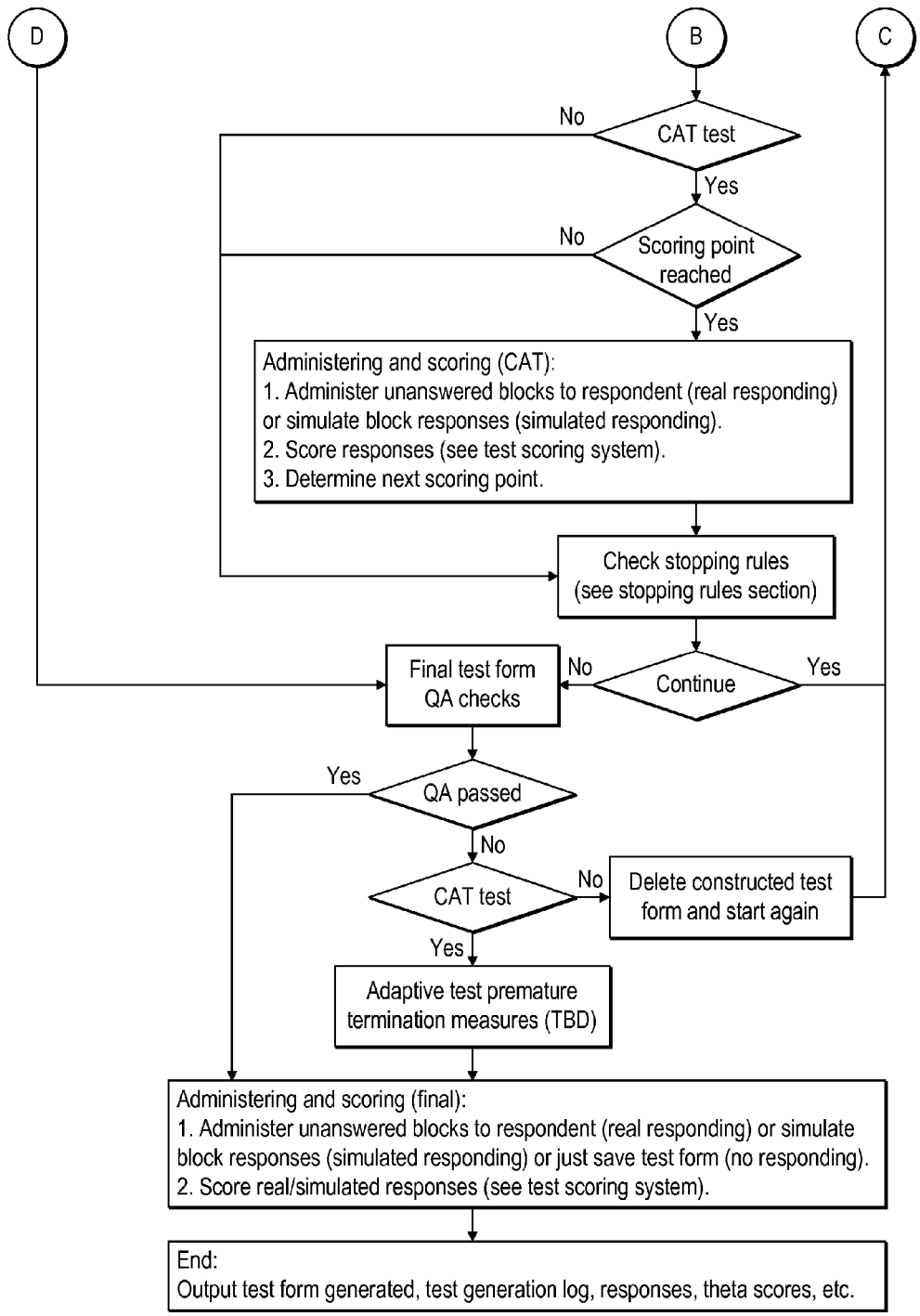

FIGS. 15 (a-c) show another example of the test generation process.

Apart from the test form itself, the test generator also creates a test generation log. This log is saved together with the generated test form in a test form database. The log allows reconstruction of what occurred during each step or stage of test generation, and may be useful for:

informing assessment design decisions;
providing data for further research into test generation methodologies;

The test generation log may cover information such as which sub procedure was called at which step, the time taken to run each triplet search, the intermediate scoring points and theta scores in a CAT test session, etc.

Optionally, instead of all candidates starting their assessments at the same project-specific theta location, the system may have the capability of using candidate-specific prior test theta scores in test generation (e.g. ReTest scenarios).

The test construction process includes the scale selector and the item selector which are now described in more detail.

Scale Selector

When (in the case of triplet blocks) more than three scales are involved, the scale selector determines which three scales to pass onto the item selector to generate the next triplet, taking into account measurements from test constructed so far, content constraints, and item availability.

Scales are prioritised for selection according to their information values and item utilisation statuses. During the assessment configuration stage, each scale is assigned the following:

Standard error target for each scale
    Maximum allowed SE (i.e. minimum information target)
    Ideal SE (i.e. ideal information target)
Item target for each scale
    Minimum number of items
    Maximum number of items During scale selection, each scale is assigned separate information and item tiers as follows:

Scale Information Tier [Tier_Info]

| | |
|---|---|
| 1 | Minimum information not met |
| 2 | Minimum information met, ideal information not met |
| 3 | Ideal information met |

Scale Item Tier [Tier_Item]

| | |
|---|---|
| 1 | Minimum number of items not met |
| 2 | Minimum number of items met, maximum number of items not met |
| 3 | Maximum number of items met |

These two tiers are then combined, whist also taking into account remaining item availability in the item bank, to give a final scale selection tier as follows:

Scale Selection Tier [Tier_ScaleSelect]

| | | Scale Information Tier | | |
|---|---|---|---|---|
| | | 1 | 2 | 3 |
| Scale Item Tier | 1 and items available | 1 | 2 | 3 |
| | 2 and items available | 2 | 4 | 6 |
| | 3 or no items available | 9 | 9 | 9 |

| Scale Selection Tier | Measurement Target | | Selection Priority | Non-scored Items |
|---|---|---|---|---|
| | Minimum | Ideal | | |
| 1, 2, 3 | Not satisfied | Not satisfied | Highest | Not allowed |
| 4 | Satisfied | Not satisfied | Medium | Not allowed |
| 6 | Satisfied | Satisfied | Lowest | Allowed |
| 9 | Measurement limit reached, scale cannot be improved further. | | N/A | N/A |

Scales with different selection tiers are treated differently in the scale selector. The lower the selection tier, the higher the priority of the scale. When two scales have the same selection tier, the one with higher information deficiency to the ideal information target is prioritised. If the tie is still not broken, the one with lower total information (sum of current test information and prior information) is prioritised.

Scales with tiers 1, 2, 3 require more information/items to reach the acceptable measurement target. Scales with tier 4 have reached the acceptable measurement target but not the ideal measurement target. Scales with tier 6 have reached the ideal measurement target but are still selectable for boosting information on other scales or administering non-scored trial items. Scales with tier 9 are not selectable. The smaller the scale selection tier, the higher priority the scale has in terms of being selected for measurement in the next forced-choice block. When two scales have the same scale selection tier, the one with higher information deficiency to the ideal information target is prioritised. If the tie is still not broken, the one with lower total information (sum of current test information and prior information) is prioritised. This is summarised into scale selection operative ranks which show no ties across scales, and it defines the prioritisation of scales within scale selection tiers.

Once the priorities of individual scales are determined, the prioritisation of scale combinations for the next forced-choice block can be considered. That is, when the priority of scales ([Rank_ScaleSelect]) is determined, a search for the best scale combination for the next triplet can begin. Depending on the measurement situation of the test generated so far, there are several scale selection phases with tailored scale selection methodologies that differ slightly from each other. The measurement aim is to eliminate scales with scale selection tiers of 1, 2 or 3, so scale combinations involving scales from lower scale selection tiers are searched first.

For triplets, the priorities of scale combinations (in terms of scale selection tier combinations) are shown below, with higher priority combinations being considered in earlier scale selection phases, as described below.

| Group | Scale Selection Tier Combinations | Scale Selection Phase |
|---|---|---|
| Tier 1 only | 1, 1, 1 | 2 |
| Tier 1, 2 only | 1, 1, 2; 1, 2, 2 2, 2, 2 | 2 |
| Tier 1, 2, 3 only | 1, 1, 3; 1, 2, 3; 1, 3, 3 2, 2, 3; 2, 3, 3 3, 3, 3 | 2 |
| Tier 1, 2, 3, 4 only | 1, 1, 4; 1, 2, 4; 1, 3, 4; 1, 4, 4 2, 2, 4; 2, 3, 4; 2, 4, 4 3, 3, 4; 3, 4, 4 | 2 |
| Tier 1, 2, 3, 4, 6 | 1, 1, 6; 1, 2, 6; 1, 3, 6; 1, 4, 6; 1, 6, 6 2, 2, 6; 2, 3, 6; 2, 4, 6; 2, 6, 6 3, 3, 6; 3, 4, 6; 3, 6, 6 | 2 |
| Tier 4, 6 only | 4, 4, 4; 4, 4, 6; 4, 6, 6 | 3 |
| Tier 6 only | 6, 6, 6 | 4 |

The test construction process goes through scale combinations one by one according to the priorities as set out above, for each scale combination trying to find a feasible triplet satisfying all content constraints by calling the item selector (details below). The search procedure is controlled by scale selection phases, designed to handle different scenarios in a test construction process:

Scale Selection Phase

| | |
|---|---|
| 0 | When a content plan (i.e. which scales to administer for the triplet in question) is entered by the user. |
| 1 | During the first few triplets in the test (specified by user, e.g. at least 5), randomisation is implemented so that candidates don't all get the same form. |
| 2 | When some of the scales have not reached their minimum measurement targets yet and can still be improved (i.e. some scales have scale selection tiers of 1, 2 or 3). |
| 3 | When all scales have either satisfied minimal measurement requirement or cannot be improved further (i.e. all scales have scale selection tiers of 4, 6 or 9). |
| 4 | When all scales have either satisfied ideal measurement requirement or cannot be improved further (i.e. all scales have scale selection tiers of 6 or 9). |
| 9 | When none of the scales can be improved further (i.e. all scales have scale selection tier 9). |

Example A provides details of an exemplary implementation of the different scale selection phases.

Example A: Scale Selection Phases Details of an Exemplary Implementation

Scale Selection Phase: 0
Qualitative Description: Content plan (i.e. user-specified scale combination for triplet in question) available.
Quantitative Description: Scale combination entered by user.
Scale Combination Search Process:
1. Pass scale combination to Item Selector, WITHOUT checking content constraints at scale level.
2. A feasible triplet is found?
   a. Yes->go to 5
   b. No->go to 3
3. Content constraints can be relaxed further?
   a. Yes->go to 4
   b. No->go to 6
4. Relax content constraints and go to 2.
5. Scale selection phase completed and successful. Reset content constraints to starting values and move onto administering/stopping rule checking.
6. Scale selection phase completed and unsuccessful. Abandon content plan, reset content constraints to starting values and launch automated scale selection (i.e. call a different scale selection phase suitable for the current measurement scenario).
Notes:
When a content plan is specified, it is assumed that the content plan entered is a reasonable one and scale level content constraints are not imposed.
The default is not to specify any content plan, but to allow the process to proceed and determine a content plan. Alternatively, the process can be configured so that scale level content constraints are imposed for user-specified content plans.
Scale Selection Phase: 1
Qualitative Description: First few triplets with scale selection randomisation.
Quantitative Description: When the triplet number is less than or equal to the number of randomised initial triplets entered by user (alternatively according to a default setting).
Scale Combination Search Process:
1. Shuffle all the scales and put them into a randomly ordered list (using a random rank NOT based on measurement situation).
2. One by one, consider scale combinations with random ranks 1,2,3; 1,2,4; 1,2,5; . . . ; 2,3,4; 2,3,5; . . . .
   A. The scale combination satisfies content constraints at scale level?
      a. Yes->go to 2B
      b. No->go to 2E
   B. Pass scale combination to Item Selector. A feasible triplet is found?
      a. Yes->go to 2C
      b. No->go to 2E
   C. Triplet construction successful. More triplets with randomised scale selection needed?
      a. Yes->go to 2D
      b. No->go to 3
   D. Remove the selected scales from the list of randomly ordered scales.
   E. More scale combinations available in remaining list of scales?
      a. Yes->move on to next combination, go to 2A
      b. No->go to 2F
   F. At least one triplet is generated from the last round of search?
      a. Yes->go to 1
      b. No->go to 4
3. Scale selection phase completed and successful. Reset content constraints to starting values and move onto administering/stopping rule checking.
4. Scale selection phase completed and unsuccessful. No scale combinations satisfy initial content constraints specified by user. Terminate test construction with warning message asking user to reconsider content constraints.
Notes:
The number of initial triplets with randomised scale selection shouldn't be too high (reduced measurement accuracy) or too low (risk of repeating forms across candidates). As a rough guide, it is recommended to use:
At least 5
About the number of triplets required to cover every scale at least once (i.e. number of selected scales/3)
Content constraints are NOT relaxed at this stage of test construction. They should not be so strict that finding a feasible scale combination become a difficult task. The suitability of content constraints is checked at assessment design stage.
Once test configurations are determined, this phase of test construction can happen before candidate sign-on (i.e. pre-generate the initial triplets with randomised scale selection and randomly assign them to candidates as they log on), so as to save test generation time on the fly.
Scale Selection Phase: 2
Qualitative Description: Some of the scales have not reached their minimum measurement targets yet and can still be improved.
Quantitative Description: Some scales have scale selection tiers of 1, 2 or 3.
Scale Combination Search Process:
1. Take all scales with scale selection tier 1. One by one, search through all scale combinations according to scale selection operative ranks. A feasible triplet is found?
   a. Yes->go to 6
   b. No->go to 2
2. Take all scales with scale selection tier 1/2. One by one, search through all scale combinations according to scale selection operative ranks, skipping over combinations with tier 1 only. A feasible triplet is found?
   a. Yes->go to 6
   b. No->go to 3
3. Take all scales with scale selection tier 1/2/3. One by one, search through all scale combinations according to scale selection operative ranks, skipping over combinations with tier 1/2 only). A feasible triplet is found?
   a. Yes->go to 6
   b. No->go to 4
4. Take all scales with scale selection tier 1/2/3/4. One by one, search through all scale combinations according to scale selection operative ranks, skipping over combinations with tier 1/2/3 only or 4 only. A feasible triplet is found?
   a. Yes->go to 6
   b. No->go to 5

5. Take all scales with scale selection tier 1/2/3/4/6. One by one, search through all scale combinations according to scale selection operative ranks, skipping over combinations with tier 1/2/3 only or 4/6 only. A feasible triplet is found?
   a. Yes->go to 6
   b. No->go to 7
6. Scale selection phase completed and successful. Reset content constraints to starting values and move onto administering/stopping rule checking.
7. Content constraints can be relaxed further?
   a. Yes->relax constraints and go to 1
   b. No->go to 8
8. Scale selection phase completed and unsuccessful. Reset content constraints to starting values and launch scale selection phase 3 to try to find a feasible triplet (if this is still unsuccessful, scale selection phase 4 is called, see phase 3 process for more details).

The search though scale combinations mentioned in the process above is conducted as follows:
   A. The scale combination satisfies content constraints at scale level?
      a. Yes->go to B
      b. No->go to C
   B. Pass scale combination to Item Selector. A feasible triplet is found?
      a. Yes->return 'yes' to feasible triplet found
      b. No->go to C
   C. More scale combinations available in list of scales?
      a. Yes->move on to next combination, go to A
      b. No->return 'no' to feasible triplet found Notes:
Scale selection phase 2 is designed for when some of the scales still require improvement to hit the minimum measurement target. Therefore, attention is limited to scale combinations involving these scales (i.e. where at least one scale has tier 1/2/3). However, there may be situations when no such combinations yield feasible triplets even when content constraints have been relaxed to their limits. In such cases, other scale combinations are considered (i.e. scale selection phase 3 and 4). If a feasible triplet is found, the content constraints relating to scale and item recycling would have been weakened for the next triplet and hopefully the process can pick scales with tier 1/2/3 again.

Scale Selection Phase: 3
Qualitative Description: All scales have either satisfied minimal measurement requirement or cannot be improved further.
Quantitative Description: All scales have scale selection tiers of 4, 6 or 9. Some scales have scale selection tier 4.
Scale Combination Search Process:
1. Take all scales with scale selection tier 4. One by one, search through all scale combinations according to scale selection operative ranks. A feasible triplet is found?
   a. Yes->go to 3
   b. No->go to 2
2. Take all scales with scale selection tier 4/6. One by one, search through all scale combinations according to scale selection operative ranks, skipping over combinations with tier 4 only/6 only. A feasible triplet is found?
   a. Yes->go to 3
   b. No->go to 4
3. Scale selection phase completed and successful. Reset content constraints to starting values and move onto administering/stopping rule checking.
4. Content constraints can be relaxed further?
   a. Yes->relax constraints and go to 1
   b. No->go to 5
5. Scale selection phase completed and unsuccessful. Reset content constraints to starting values and launch scale selection phase 4 to try to find a feasible triplet.

The search though scale combinations mentioned in the process above is conducted as follows (as per Scale Selection Phase: 2):
   A. The scale combination satisfies content constraints at scale level?
      a. Yes->go to B
      b. No->go to C
   B. Pass scale combination to Item Selector. A feasible triplet is found?
      a. Yes->return 'yes' to feasible triplet found
      b. No->go to C
   C. More scale combinations available in list of scales?
      a. Yes->move on to next combination, go to A
      b. No->return 'no' to feasible triplet found Notes:
Scale selection phase 3 is designed for when all the scales have either hit the minimum measurement target or cannot be improved further. Therefore, attention is limited to scale combinations involving the scales which can be improved further towards the ideal (i.e. where at least one scale has tier 4). However, there may be situations when no such combinations yield feasible triplets even when content constraints have been relaxed to their limits. In such cases, other scale combinations are considered (i.e. scale selection phase 4). If a feasible triplet is found, the content constraints relating to scale and item recycling would have been weakened for the next triplet and hopefully the process can pick scales with tier 4 again.

Scale selection phase 3 can also be called in a situation where some scales have yet to meet the minimum measurement target but no feasible triplet can be found in scale selection phase 2.

Scale Selection Phase: 4
Qualitative Description: All scales have either satisfied ideal measurement requirement or cannot be improved further.
Quantitative Description: All scales have scale selection tiers of 6 or 9. Some scales have scale selection tier 6.
Scale Combination Search Process:
1. Take all scales with scale selection tier 6. One by one, search through all scale combinations according to scale selection operative ranks. A feasible triplet is found?
   a. Yes->go to 2
   b. No->go to 3
2. Scale selection phase completed and successful. Reset content constraints to starting values and move onto administering/stopping rule checking.
3. Content constraints can be relaxed further?
   a. Yes->relax constraints and go to 1
   b. No->go to 4
4. Scale selection phase completed and unsuccessful. No scale combinations can produce a feasible triplet even when content constraints have been relaxed to their limits. Terminate test construction and move onto final test form quality assurance/administering procedures.

The search though scale combinations mentioned in the process above is conducted as follows (as per Scale Selection Phase: 2):

D. The scale combination satisfies content constraints at scale level?
   a. Yes->go to B
   b. No->go to C
E. Pass scale combination to Item Selector. A feasible triplet is found?
   a. Yes->return 'yes' to feasible triplet found
   b. No->go to C
F. More scale combinations available in list of scales?
   a. Yes->move on to next combination, go to A
   b. No->return 'no' to feasible triplet found Notes:
Scale selection phase 4 is designed for when all the scales have either hit the ideal measurement target or cannot be improved further. When this is the case, the test can be instructed to
   Terminate (if minimum test length has been reached), in which case scale selection phase 4 is not called;
   Continue, in which case scale selection phase 4 is called, and the test goes on until maximum test length is reached or until no feasible triplets can be found.
Scale selection phase 4 can also be called in situations where
   some scales have yet to meet the minimum measurement target but no feasible triplet can be found in scale selection phase 2 or 3;
   some scales have yet to meet the ideal measurement target but no feasible triplet can be found in scale selection phase 3.

Scale Selection Phase: 9
Qualitative Description: None of the scales can be improved further.
Quantitative Description: All scales have scale selection tier 9.
Scale Combination Search Process:
None of the scales can be selected. No additional blocks can be generated. Terminate test.

Broadly, combinations of three scales are searched one by one and the scale-level content constraints are checked for each combination. If a three-scale combination satisfying all scale-level content constraints is found, the combination is passed onto the item selector to generate a triplet. If no suitable triplet is found by the item selector, the scale combination search continues. If all combinations have been checked and still no feasible triplet is found, scale and/or item constraints are relaxed (according to the constraint relaxation strategy specified in the process settings) and the search is repeated. If constraints cannot be relaxed further and the search is still futile, test construction terminates because no feasible triplet exists. The content constraints, process settings and stopping rules are described in more detail below.

The process outlined above with scale selection tiers and scale selection phases is intended to provide an efficient scale selection process. The scale selector may be adapted to produce different block sizes, for example for constructing pairs or quads instead of triplets.

Figure 16:
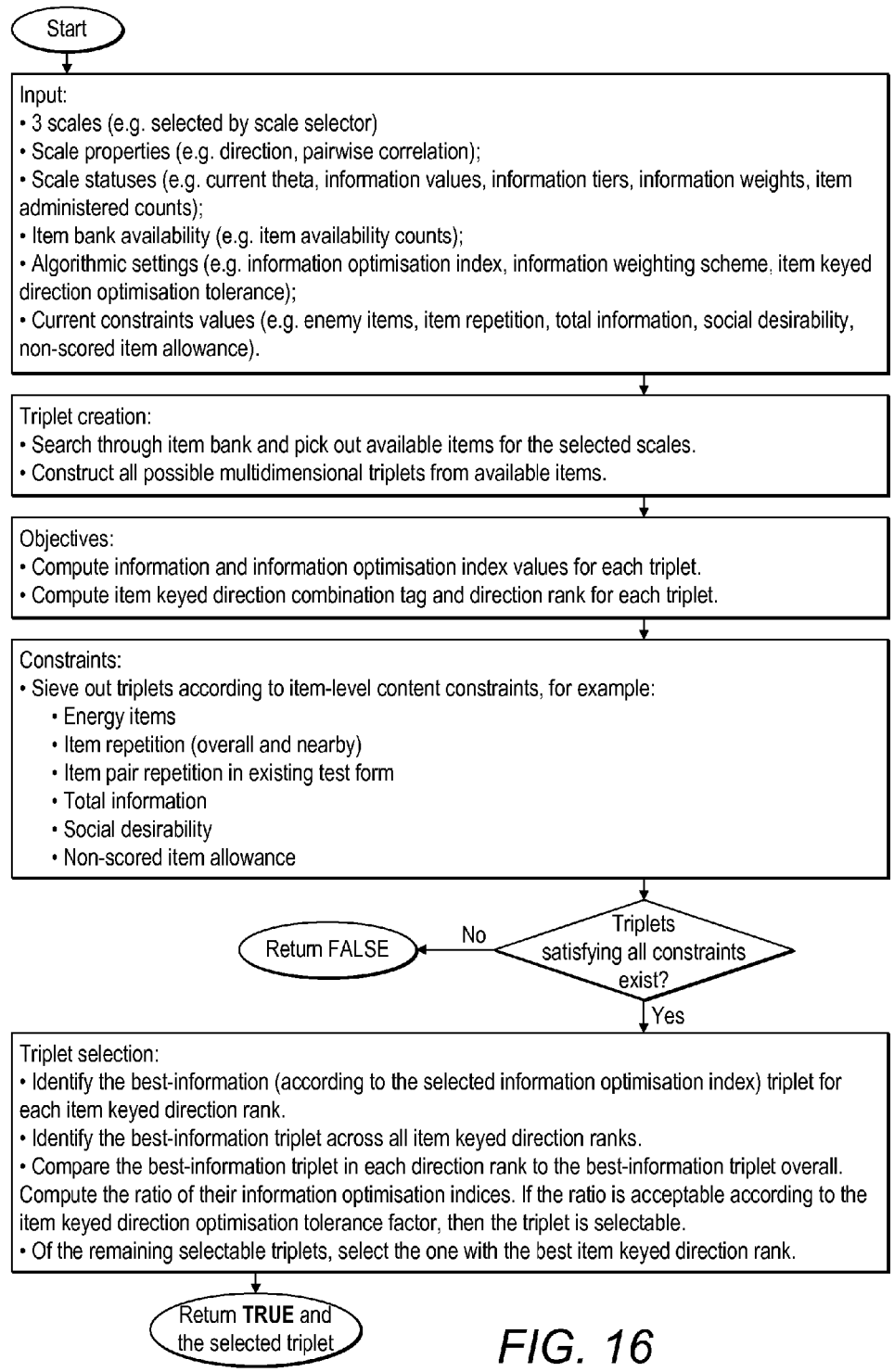
FIG. 16 shows another example of the triplet selection process.

Item Selector (Triplets)
FIG. 16 shows another example of the triplet selection process.

When three scales are passed to the item selector (also referred to as 'triplet selector' in the case of triplet item blocks), it constructs a triplet to optimize measurement, taking into account measurements from the test constructed so far, content constraints, and item bank availability.

When generating and selecting triplets, the item selector not only optimises IRT information but also balances the combination of positively and negatively keyed items in the test, according to measurement settings specified during the assessment configuration stage (e.g. specified in a test configuration input frontend).

Measurement settings
   information optimisation index
   Target item keyed combination proportion
   Item keyed direction optimisation tolerance factor Often the triplet with the best (RI information is not a triplet with the desired combination of positive and negative keyed items. In such cases, a decision is made as to which target to prioritise. If the sacrifice of IRT information is not large, then the item keyed direction combination is prioritised. Otherwise, IRT information is prioritised. This decision is based on the item keyed direction optimisation tolerance factor, which takes values between 0 and 1 and represents the threshold proportion of IRT information beyond which sacrifice of the IRT information is not acceptable. A value of 1 means that IRT information is not to be sacrificed at all and should always be prioritised; a value of 0 means that IRT information can be sacrificed completely and item keyed direction combination should always be prioritised (and the best-information triplet with that item keyed direction combination is subsequently selected). In practice, such extreme values are rarely optimal for measurement and a more reasonable value between 0 and 1 is chosen. The optimal value for a particular assessment is determined using simulations (e.g. with the simulation engine described below).

The item selector may be adapted to produce different block sizes, for example for constructing pairs or quads instead of triplets. The item selector may also provide further methods for balancing the priorities between IRT information and item keyed direction combination.

Optionally, instead of always picking the best triplet, the item selector may randomly select a triplet from a specific group of optimal or candidate triplets, for example, the best 5 triplets. This can provide an additional layer of randomness and potentially reduce exposure of particular optimal triplets across test forms, at the expense of measurement efficiency.

Content Constraints
The scale selector and the item selector attempt to pick the best scale and item combinations according to measurement targets, but content constraints are required to balance test contents. Content constraints exist at test, scale and item levels and their values can be adjusted to suit each project; some examples of content constraints include (hard/soft types are described below):

| Constraint | Description | Level | Type |
| --- | --- | --- | --- |
| Job complexity level | Task and people complexity levels, for selecting appropriate contents for the levels of the job in question. For example, 5 levels for people/task complexities may be used, but more or fewer levels may also be used. | Scale, Item | Hard |
| Test length | Minimum and maximum number of forced-choice blocks in test. | Test | Hard |
| Scale recycling - overall | The number of times a scale can be picked in a test, i.e. the maximum number of items allowed in a test from the given scale. | Scale | Hard |
| Scale recycling - nearby blocks | Minimum number of intermediate blocks between two blocks containing the same scale. | Scale | Soft |
| Scale pair recycling - overall | The number of times a scale pair can be selected in a test, to limit the number of times any two scales are compared in a test. | Scale | Soft |
| Scale pair recycling - nearby blocks | Minimum number of intermediate blocks between two blocks containing the same scale pairs. | Scale | Soft |
| Item recycling - overall | The number of times an item can be picked in a test. | Item | Soft |
| Item recycling - nearby blocks | Minimum number of intermediate blocks between two blocks containing the same item. | Item | Soft |
| Item pair recycling - overall | Each item pair can only appear once in any test session. | Item | Hard |
| Retest recycling | Scale and item recycling constraints placed on a second test session to avoid repetition of contents in the first test session. | Test, Scale, Item | Hard |
| Scale enemies | Scales which should not be paired under any circumstances in the test session. | Scale | Hard |
| Item enemies | Items which should not be paired under any circumstances in the test session. Note that items under the same scale are by default not going to be compared and hence don't need to be entered as item enemies. | Item | Hard |
| Non-scored items allowance | Whether non-scored items are allowed, and if so how many are allowed per test form. Non-scored items can be, for example, experimental items that we wish to collect data for. Note that even when non-scored items are allowed, selection of such items is only permitted from scales with selection tier 6 (i.e. ideal information has been achieved and there is still capacity to administer more items). | Test, Item | Hard |
| Scale correlation | Maximum absolute scale correlation allowed in a forced-choice block, to avoid comparing scales which are too similar. | Scale | Soft |
| Maximum social desirability difference | Maximum social desirability difference allowed between items in a forced-choice block, to minimise response biases due to some items being more/less desirable than others in the same block. | Item | Soft |
| Minimum block information | Minimum total information required from a forced-choice block, to deal with situations where even the best triplet is not satisfactory. | Item | Soft |

Content constraints are classified into two types: hard and soft. Hard constraints are set at the beginning of the test session and remain unchanged throughout the test. Soft constraints start off strict at the beginning of a test session, and are gradually relaxed if the process struggles to create forced-choice blocks satisfying all constraints. To control the relaxation of test constraints, each soft constraint requires three values: start, adjustment and end. Start value is the ideal constraint value set at the beginning of the test, adjustment value is the size of adjustment to the constraint on each relaxation, and end value is the worst case scenario acceptable in a test session beyond which no relaxation is allowed.

Constraint options include for example a constraint deactivation option, and a constraint format changing option. Further possible constraints include for example retest constraints, a similar items constraint, and a constraint for word count balancing of items in a block.

Process Settings

The test construction process has several settings. They function under the same structure but offer slightly different measurement options to suit the need of each project. Process settings include for example:

| Process Settings | Description |
| --- | --- |
| Initial content randomization | This is the number of forced-choice blocks with randomised scale selection at the beginning of the test. If the item selector is set to always pick the best item block, this randomization is introduced at the beginning of the test so that candidates don't all get the same optimal form. |
| Information optimization index | A forced-choice block provides a piece of IRT information for each of the several scales being measured in that block. An information optimization index is a mathematical equation that combines these pieces of IRT information |

| Process Settings | Description |
|---|---|
| Scale information weighting scheme | relating to different scales into one single index, so that all forced-choice blocks can be ranked according to one single number in the item selector. Several exemplary information optimization indices are described above. Some of the information optimization indices use weighting of different scales according to their measurement status (e.g. according to their scale selection tiers). How the scales are weighted against each other is determined by the scale information weighting scheme. For example, scales can be weighted the same, or alternatively, scales requiring more information can be weighted over those requiring less information. |
| Constraints relaxation strategy | There are multiple soft content constraints which can be relaxed during a test session, and there are different orders in which these constraints can be relaxed. The constraint relaxation strategy determines how the multiple constraints are relaxed. For example, constraints can be relaxed one by one (with the advantage of better content selection) or simultaneous (with the advantage of reduced computational intensity). In general, scale-level constraints are relaxed before item-level constraints, as the latter have a greater impact on measurement. |
| CAT scoring frequency scheme (CAT only) | When generating a forced-choice block, the process looks for the optimal item bock, say, the best triplet, at a given theta location (default location: population average). In a non-adaptive test session, this theta location does not change. In an adaptive test session, this theta location is updated as the test session progresses by repeatedly scoring the responses collected so far. A higher scoring frequency produces better measurement accuracy at the expense of higher system and internet speed requirements. The frequency of the theta location update is controlled by a CAT scoring frequency scheme suitable for the project. For example, scoring can be conducted after every 10 blocks for the first 30 blocks and reduced to every 5 blocks thereafter. |
| Continuation pass ideal | When the ideal measurement target has been achieved (or, in sme embodiments, measurement cannot be improved with available items) for all scales, one may decide to:<br>Terminate the test as it is and minimise test length; or<br>Continue until maximum test length is reached, so as to improve measurement further and/or collect more data on trial items, for example.<br>The assessment designer can specify whether to continue the test session once ideal measurement has been reached. |
| Final test form quality assurance scheme | For non-adaptive tests, when the test construction reaches termination point, some final test form quality assurance checks are conducted. Multiple quality assurance criteria can be adopted, such as checking whether minimum test length has been reached, whether minimum number of items per scale has been reached, whether minimum IRT information per scale has been reached, and any other additional quality assurance schemes specified by the assessment designer. Prematurely terminated test forms failing the quality assurance criteria can be dropped and a better test form regenerated for the candidate. For adaptive tests, the test construction process and the candidate responding process are inseparable, so the test form constructed and administered so far cannot be dropped as in the case of non-adaptive tests. However, the quality assurance checks are still applied, and prematurely terminated forms flagged. Rescue strategies such as automatically launching a re-test session or continue test generation while lowering test constraints further (i.e. beyond the satisfactory threshold input by the test designer) may be implemented. |

Optionally, CAT scoring frequency scheme may display a lag to buffer Internet streaming. For example, while the candidate responds to the nth set of questions, the system scores responses from the first (n−1) sets and generate the (n+1)th set.

Example B provides details of an exemplary implementation of the process settings.

Example B: Process Settings Details of an Exemplary Implementation

Initial Content Randomization

Because the Item Selector can be configured to always pick the best forced-choice block, if no randomization was introduced into the test generation process then under the same test configurations the Test Construction Process would always create the same optimal form. To ensure that candidates get different test forms, randomisation is required in the test generation process. Randomisation can be introduced in a number of ways:

1. Introduce randomization in the Item Selector, so that it picks one of the best forced-choice blocks. For example, instead of always picking the best forced-choice block, it could:
    a. Randomly select one of the best 5% (figure variable) forced-choice blocks;
    b. Randomly select one of the best 10 (figure variable) forced-choice blocks;
    c. Randomly select one of the forced-choice blocks which were performing at least 80% (figure variable) as well as the best forced-choice block.
2. Introduce randomization at the beginning of the test, so that after a set number of forced-choice blocks the starting points for generating the remaining of the test are sufficiently different across candidates and such differences permeates to the rest of the test forms. This could be achieved by:
    a. Randomizing the starting theta value, so instead of having all candidates starting at the population average they start at slightly different theta locations (resulting in different initial best forced-choice blocks);

b. Randomizing scale selection at the beginning of the test so that it is not entirely based on measurement targets. Above Scale Selection Phase 1 provides an example of this approach.
  c. Randomise item selection at the beginning of the test so that it is not entirely based on measurement targets. This involves applying randomization in the Item Selector (as detailed above) for the beginning of the test only.
3. Use a combination of the methods above.

Information Optimization Index

Items in the same forced-choice block often contribute to measuring different scales. Using the Thurstonian IRT model, IRT information for each of the scales involved could be computed, providing a measure of the amount of information gained by the forced-choice block for each scale respectively. For example, in a triplet where the three items I, J and K contribute to measuring scales A, B and C respectively, the forced-choice block provides three pieces of IRT information, $InfoBlock_a$, $InfoBlock_b$ and $InfoBlock_c$, for each of the scales A, B and C.

IRT information for each scale allows the measurement efficiency of forced-choice blocks to be ranked with respect to a single scale. However, IRT information from all the scales involved in a forced-choice block need to be combined into a single index if the forced-choice blocks are ranked with respect to all scales involved. The Information Optimization Index is a mathematical equation for combining IRT information from different scales into a single index for this ranking purpose. This ranking operation is essential for identifying the best forced-choice block to select in the Item Selector.

A number of different example Information Optimization Indices are described in the table below. The examples given below are for triplets, and the same principle can be extended to pairs, quads and forced-choice blocks of any size. The Test Construction Process can utilise any of these indices (as well as other indices not specifically listed, as long as they are not fundamentally incompatible with the Thurstonian IRT model). For example, an assessment designer can select an Information Optimization Indices by selecting it from a drop-down box in the Test Configuration Input Frontend. New Information Optimization Indices can be added into the Test Construction Process.

| Inf Opt Ind # | Description | Equation | Direction |
|---|---|---|---|
| 1 | Maximise total block information | $sum(InfoBlock_a, InfoBlock_b, InfoBlock_c)$ | MAX |
| 2 | Minimising total ideal information deficiency (maximise capped total block information) | $sum(max(InfoIdeal_a - InfoTotal\_T_a - InfoBlock_a, 0), max(InfoIdeal_b - InfoTotal\_T_b - InfoBlock_b, 0), max(InfoIdeal_c - InfoTotal\_T_c - InfoBlock_c, 0))$ | MIN |
| 3 | Minimise total squared ideal information deficiency (gives priority to larger deficiencies) | $sum(max(InfoIdeal_a - InfoTotal\_T_a - InfoBlock_a, 0)^2, max(InfoIdeal_b - InfoTotal\_T_b - InfoBlock_b, 0)^2, max(InfoIdeal_c - InfoTotal\_T_c - InfoBlock_c, 0)^2))$ | MIN |
| 4 | Maximise weighted total block information | $sum(w_a*InfoBlock_a, w_b*InfoBlock_b, w_c*InfoBlock_c)$ | MAX |
| 5 | Minimising weighted total ideal information deficiency (maximise weighted capped total information) | $sum(w_a*max(InfoIdeal_a - InfoTotal\_T_a - InfoBlock_a, 0), w_b*max(InfoIdeal_b - InfoTotal\_T_b - InfoBlock_b, 0), w_c*max(InfoIdeal_c - InfoTotal\_T_c - InfoBlock_c, 0))$ | MIN |
| 6 | Maximise product total information (minimising volume of confidence ellipsoid) | $product((InfoTotal\_T_a + InfoBlock_a), (InfoTotal\_T_b + InfoBlock_b), (InfoTotal\_T_c + InfoBlock_c))$ | MAX |
| 7 | Maximise capped product total information | $product(min(InfoTotal\_T_a + InfoBlock_a, InfoIdeal_a), min(InfoTotal\_T_b + InfoBlock_b, InfoIdeal_b), min(InfoTotal\_T_c + InfoBlock_c, InfoIdeal_c))$ | MAX |

Keys:
$InfoBlock_a$ = information for scale A from the current forced-choice block
$InfoTotal\_T_a$ = information for scale A from pre-assessment prior information and previous forced-choice blocks already in the test form
$InfoIdeal_a$ = ideal information target for scale A (specified by assessment designer as measurement target)
$w_a$ = information weight for scale A (see Scale Information Weighting Scheme section)

Scale Information Weighting Scheme

Some Information Optimization Indices apply weighting by scales according to their measurement status. In general, 'weaker' scales requiring more measurement attention are given higher weights than 'stronger' scales where sufficient information has already been collected. The different weighting methods are captured under different Scale Information Weighting Schemes. Some examples for triplets are given below, and the same principle can be extended to pairs, quads and forced-choice blocks of any size. For example, an assessment designer can select a Scale Information Weighting Schemes by selecting it from a drop-down box in the Test Configuration Input Frontend. New Scale Information Weighting Schemes can be added into the Test Construction Process.

| Description | Equation | Relevant Inf Opt Ind # |
|---|---|---|
| Unit weight (all scales weighted the same) | $w_a = 1$ for all scales | 1, 2, 3, 6, 7 |
| Banded weight by Scale Information Tier (scales weighted differently according to their IRT information status in the test constructed so far) | $w_a = 0.1$ if scale has information tier = 3<br>$w_a = 1.0$ if scale has information tier = 2<br>$w_a = 2.0$ if scale has information tier = 1.<br>(actual weight values can be variable) | 4, 5 |

Constraints Relaxation Strategy

In the Test Construction Process, there are multiple soft Content Constraints which can be relaxed during a test session. When, how much and in what order these soft constraints are relaxed are controlled by Constraint Relaxation Strategies. Some examples are given below. For example, an assessment designer can select a pre-defined Constraints Relaxation Strategy by selecting it from a drop-down box in the Test Configuration Input Frontend. Moreover, additional bespoke methods can be easily engineered into the Test Construction Process (providing for example flexibility in terms of changing how and in what order constraints are relaxed, and/or the time point for constraint relaxation).

| Description | Pros & Cons |
|---|---|
| Relax one constraint at a time and one adjustment at a time. Relax scale-level constraints before relaxing item-level constraints (with some default constraint order). | Good for test optimization, but very computationally intensive. |
| Relax all scale-level constraints together one adjustment at a time, if no more relaxation can be done then move onto relaxing all item-level constraints together one adjustment at a time. | More computationally economical but constraints are relaxed quickly and measurement can be compromised. |

CAT Scoring Frequency Scheme (Only Relevant for CAT Tests)

When the Test Construction Process generates a forced-choice block during a test construction session, it searches for the optimal triplets at a given theta location. In a non-adaptive test construction session (LOFT and MPTF), this theta location does not change (default location: target population average). In an adaptive test session involving tailoring the test to the candidate (CAT), this theta location is updated repeatedly by scoring the candidate responses collected so far. The frequency of scoring and updating the theta location can be configured, with higher scoring frequencies producing better measurement accuracy at the expense of higher system and internet speed requirements. This frequency is controlled by CAT Scoring Frequency Schemes, some examples of which are provided below. For example, an assessment designer can select a CAT Scoring Frequency Schemes by selecting it from a drop-down box in the Test Configuration Input Frontend. Moreover, new CAT Scoring Frequency Schemes can be added into the Test Construction Process.

| Description | Scoring interval (number of forced-choice blocks until next scoring point) |
|---|---|
| Run scoring after a fixed number of blocks. For example, if the scoring interval is specified to be 5 blocks, scoring is conducted after block 5, 10, 15, etc. | A fixed number specified by user input |
| Run scoring after a dynamic number of blocks depending on how many scales are still requiring additional information. This results in less frequent scoring at the beginning of the test, and more frequent scoring later on. For example, if scoring was conducted after K triplets and 18 scales still require additional information, then the scoring interval would be 18/3 = 6 triplets, resulting in the next scoring point being after triplet K + 6. | (Number of remaining scales requiring information)/(block size) |
| Run scoring after every i (e.g. 10) blocks for the first n (e.g. 30) blocks and reduced to every j (e.g. 5) blocks thereafter | Two or more fixed numbers specified by user input |
| Run scoring with a time lag to buffer the impact of slow computational/internet speed - e.g. while scoring is being conducted for the first K triplets, the candidate sees and responds to the (K + 1)th triplet generated from theta scores recovered from the first K − 1 triplets. | Specified by user input and/or dependent on computational/internet speed |

Final Test Form Quality Assurance Schemes

For non-adaptive tests (LOFT and MPTF), when the test construction reaches termination point, some final test form quality assurance (QA) checks are conducted and the forms failing the QA checks can be dropped and regenerated. The QA checks are controlled by Final Test Form QA Schemes, For example, a list of available Final Test Form QA Schemes is presented to the test designer in the Test Configuration Input Frontend, and the test designer can choose which ones to switch on (the test designer can switch on none, one, some, or all QA schemes, unlike the case of most other process settings where one and only one of many options must be selected). New Final Test Form QA Schemes can be added into the Test Construction Process. Some examples of Final Test Form QA Schemes are:

Minimum test length reached
Minimum number of items reached for all scales
Minimum information reached for all scales
Content balancing is acceptable
Item keyed direction combination proportions are acceptable For adaptive tests (CAT), the test construction process and the candidate responding process are inseparable, so the test form constructed and administered so far cannot be dropped as in the case of non-adaptive tests (LOFT and MPTF). However, the QA checks are still applied, and prematurely terminated forms flagged and documented. Strategies for improving prematurely terminated adaptive tests include:

a) Automatically launching a re-test session to collect more information from the candidate;
b) Continue test generation while lowering test constraints further (i.e. beyond the satisfactory thresholds specified by the test designer);
c) Terminate measurement and flag the issue in the assessment output, leaving the judgement call to professional test users.

Stopping Rules

After the construction (and administration and scoring in adaptive tests) of each forced-choice block (i.e. at the end of each loop in the test construction process), the stopping rules are checked to decide whether to generate the next block ('continue') or stop further test construction (germinate):

1. Maximum test length reached. (Yes->Terminate; No->2)
2. Minimum test length reached. (Yes->3; No->Continue)
3. Minimum number of items reached for each scale. (Yes->5; No->4)
4. For each scale where the minimum number of items has not been reached, there is no more item available for selection. (Yes->5; No->Continue)
5. Minimum information reached for each scale. (Yes->7; No->6)
6. For each scale where the minimum information has not been reached, there is no more item available for selection or the maximum number of items has been reached. (Yes->7; No->Continue)
7. Now all scales have selection tier values of 4 or above. Log it on test generation log. Move onto 8.
8. Ideal information reached for each scale. (Yes->10; No->9)
9. For each scale where the ideal information has not been reached, the maximum number of items has been reached, or there are no more items available for selection. (Yes->10; No->Continue)
10. Now all scales have selection tier values of 6 or above. Log it on test generation log. Move onto 11.
11. Check stopping logic setting on continuing to collect data after reaching measurement ideal (to improve measurement further or collect experimental item data). (Yes->Continue; No->Terminate)

A test construction session can also reach termination point in the middle of a forced-choice block construction loop:

1. The number of scales available for selection meets or exceeds the size of the forced-choice block. (Yes->2; No->Terminate)
2. One of the selectable scale combinations produces a feasible forced-choice block. (Yes->block generation successful; No->Terminate)

Termination suggests that the generated test form has reached measurement target (mature termination) or cannot be improved further given the test constraints (premature termination). The proportion of premature terminations should be minimised, by, say, repeatedly adjusting test configurations and running simulations (for example in the assessment designer described in more detail below) until the estimate proportion of premature termination is under an acceptable threshold (the threshold value may be a predetermined value, say under 5%). The type of termination is flagged by final test form quality assurance results. Optionally, on premature termination a retest session may be automatically initiated).

Test Administration, Scoring and Reporting

As illustrated in FIG. 5, once test construction is complete (or in CAT in parallel with test construction) candidate responses are collected, the responses are scored, in the scoring engine 120, and the scores are reported with the Reporting structure module 130.

FIG. 17 shows an example of a candidate response.

FIG. 18 shows an example of the scoring of a candidate's responses.

FIG. 19 shows an example of a test report of a candidate's scores. In the illustrated example some parameters relating to the test generation are shown, the test generated and the candidate responses are shown, and the evaluated scores (theta estimate) for the scales are shown along with further information relating to the test and its evaluation (number of items administrated, information estimate, theta standard error, consistency metrics).

Potential Test Construction Improvements/Upgrades

A few assumptions are made in the design of the system described above; one or more of these may be relaxed in alternative embodiments:

The assessments adopt a multidimensional forced-choice design. Alternative measurement architectures may be required for uni-dimensional forced-choice or rating scale designs.

Each assessment utilises one and only one item bank. Different assessments can be combined at solution level.

Each item contributes to one and only one scale within each construct framework. IRT scoring is conducted at the scale level.

An item's IRT parameters stay the same over time. The psychological constructs being measured stay the same over time.

Due to the nature of items concerned (i.e. non-cognitive), item re-use will be constrained within candidate but item exposure control will not be imposed across candidates.

When the assessment is delivered online, skipping of questions is not allowed.

Block Sizing and Composition

The process may be easily modified to generate multidimensional pairs/quads or blocks of any size and/or a structural change will allow the construction of uni-dimensional forced-choice blocks as well as multidimensional ones.

Prioritisation of Item Keyed Direction

Research has shown that the IRT information formula may have some weakness in differentiating the two types of information from questions involving different item keyed direction combinations (i.e. information on theta score differences from ++ or -- pairs; information on theta score sums from +- or -+ pairs). In some embodiments the process structure may therefore be changed to allow prioritisation of item keyed direction over IRT information in some situations. This prioritisation may be automatic in the test construction process, potentially switching between the two options based upon IRT information and item keyed directions in the test constructed so far. Other processes may also be used.

Item Keyed Direction Balancing

The current process balances item keyed direction across all scales. In some embodiments, in order to improve measurement accuracy, the item keyed direction for each scale may be considered and balanced individually (this would also ensure balance across all scales). In such embodiments, the preferred proportions of item keyed directions may vary by scales.

In some embodiments, one or more preferred proportions of item keyed directions may also be set.

Content Balancing

Content balancing involves ensuring the numbers of comparisons between any two scales are more or less balanced across all scales being measured. Where this may add value in addition to test construction based on IRT information, it may be provided for example by means of a plug-in.

Social Desirability Balancing

Social desirability balancing is an important consideration in forced-choice test construction. This may be introduced by means of an automated social desirability estimation plug-in, taking into account general desirability of the items and any application-specific variation (e.g. job role, culture, assessment stake, etc, information may come from subject expert and/or mining of existing datasets)—without necessarily impacting on the structure of the current process. The social desirability estimation of items may be dynamic.

Triplet Selection by IRT Information

In some embodiments, a crude information check, such as one using a minimum total information constraint $I_{min}$, may be used at the initial filter stage to drop a proportion of bad triplets to reduce the amount of calculations required at the optimisation stage. Alternatives to the minimum total information constraint may be used.

At the optimisation stage, alternative information optimisation indices may be used.

Test Quality Check

For LOFT testing especially, some additional checks may be included at the end of the test construction to check overall test quality. Such checks may involve looking at content balancing, individual scale measurement accuracy, overall item keyed direction balancing, suitability of the test to the population and not just the average person, etc. For CAT testing, tests are tailored to each candidate but logging the results of such checks may still be informative, for example, for flagging content deficit in the item bank and/or conducting further test construction research.

Test Termination Criteria

Various alternative test termination criteria may be used.

Triplet Searching Optimisation

Searching through all possible triplets and comparing them becomes computationally intensive when the item bank grows larger (e.g. 10 items per scale give $10^3=1000$ triplets, 20 items per scale give $20^3=8000$ triplets). To improve computational efficiency, alternative discrete multidimensional optimisation methods may be used. These may involve first finding some good locations in the item parameter space and then searching for items from these good locations to make up good triplets.

Item Banding

In some embodiments, a further gain in computation efficiency may be achieved by allocating items to bands according to item properties. This allows for a quick initial selection of suitable items for the scales of interest.

For example, in a simplified scenario the 5 items listed in the table below are available for a scale. One of these items is to be combined with items from other scales to form a triplet. The item parameters (loading, threshold) of items 1, 2 and 3 are similar, therefore items 1, 2 and 3 are treated as functionally similar; and analogously items 4 and 5. Hence the 5 items are grouped into 2 bands as shown, each band having associated parameters (loading, threshold).

| Item | Loading | Threshold | Band | Band loading | Band threshold |
|---|---|---|---|---|---|
| 1 | 0.7 | 1.2 | 1 | 0.75 | 1.25 |
| 2 | 0.7 | 1.3 | | | |
| 3 | 0.8 | 1.3 | | | |
| 4 | −0.7 | −0.5 | 2 | −0.75 | −0.6 |
| 5 | −0.8 | −0.7 | | | |

If the other two scales in the triplet have 8 and 12 items available and if no banding is performed, then 5×8×12 combinations would need to be considered. With the banding shown in the table above, only 2×8×12 combinations would need consideration.

Banding can be applied to all three scales. For example, if all three scales have 5 items grouped into 2 bands similar to the table above, then without banding there are 5×5×5=125 combinations to consider. But after banding, there are 2×2×2=8 combinations to consider for band selection, followed by, say if there are 3 items in the selected bands of each scales, there are 3×3×3=27 combinations to consider to select a triplet.

The exact form and boundaries of bandings may be defined to optimise efficiency of comparison without significantly reducing the quality of the item block selection process.

CAT optimisation

In some embodiments, an initial mini-LOFT test may be used to obtain some initial theta score estimates for a candidate before moving into full adaptive testing. Moreover, adaptation and scoring may run at mini-LOFT level rather than at triplet level. Various combinations of the above are also possible.

Where computational and/or internet transmission time proves to be a problem for CAT testing, various time-reduction shortcuts may be used. For example, an embodiment using a series of mini-LOFTs may typically use a procedure as follows:
1. Present the $N^{th}$ mini-LOFT (created based on scores on the first (N−1) mini-LOFTs) to the candidate
2. Collect candidate responses (system waits)
3. After candidate responding, system scores the first N mini-LOFTs (candidate waits)
4. Then system generates the $(N+1)^{th}$ mini-LOFT based on scores on the first N mini-LOFTs (candidate waits)
5. Present the $(N+1)^{th}$ mini-LOFT to the candidate An alternative shortcut to reduce testing time would be as follows:
1. Present the $N^{th}$ mini-LOFT (created based on scores on the first (N−2) mini-LOFTs) to the candidate
   a. Collect candidate responses
   b. At the same time, the system:
      i. scores the first (N−1) mini-LOFTs
      ii. generates the $(N+1)^{th}$ mini-LOFT based on scores on the first (N−1) mini-LOFTs
2. When ready, present the $(N+1)^{th}$ mini-LOFT to the candidate Such a process may reduce system idle time and/or computational load to speed up the testing process.

Automating the Test Configuration

The system may be adapted to receive requirements data directly from external and/or third party requirements generation systems.

Other Components Interacting within the System

Now some of the other components that may interact within the system are described in more detail. Components can for example provide structures for storing inputs for and outputs from the system.

The components, sub-components and interfacing between components are as follows:

| Primary Components | Secondary Components | Interface with Other Primary Components | Interface with Databases |
|---|---|---|---|
| Assessment Designer | Test Configuration Input Frontend Simulation Engine | Test Generator Test Scoring Component | Item Bank Configuration Database Project Database Test Form Database |
| Test Generator (as described above) | Test Construction Process | Assessment Designer Online Test Delivery Component Offline Test Delivery Component Test Scoring Component | Item Bank Configuration Database Project Database Candidate Database Test Form Database |
| Online Test Delivery Component Offline Test Delivery Component Test Scoring Component | Online Test Delivering Platform Offline Test Delivering Platform Response Reader Forced-choice Pair Converter IRT Scoring Process IRT Consistency Ratio Calculator | Test Generator Test Scoring Component Test Generator Test Scoring Component Assessment Designer Test Generator Online Test Delivery Component Offline Test Delivery Component | Item Bank Test Form Database Item Bank Test Form Database Item Bank Test Form Database Candidate Database |

The primary components are separate entities, with linkage through data transmitting interfaces. This is so that the primary components can be upgraded or expanded individually without the need of re-engineering the whole system (provided that the data transmitting interfaces are kept the same or updated accordingly).

Supporting databases are required to provide input to and store outputs from the system. To facilitate further research, easy and reliable data extraction functionalities are built into each of these databases. Databases required for assessments include (but are not necessarily limited to):

Item Bank(s)
Configuration Database
Test Form Database
Project Database
Candidate Database The above components, sub-components and databases are now described in more detail (the test generator is described above).

Item Bank(s)

The system can accept different psychological (or other) content, as long as it is suitable for forced-choice Thurstonian IRT measurement. Contents are provided to the system in the form of item banks (or content banks). There can be more than one item bank (e.g. one for each of: personality, motivation, interest, values, etc). Therefore the system has the ability to accept different item banks for different tests. Typically (but not necessarily) each assessment utilises items from only one item bank. The different item banks are constructed with the same architecture, for standardising the interface with the system.

An item bank stores properties and statuses of items and scales, and any relationships among them. Information to be stored in item banks includes (but is not limited to) the following:

General
  Unique item bank tag (for calling the item bank within the system);
Items and Item Properties
  Unique item tags for identifying the same item across multiple versions;
  Multiple versions of item texts:
    Unique item text version tags for identifying different versions of the same item (e.g. different trial versions, language versions);
    Item text for each version;
    Status flag for each version of each item:
      Published: published/still in trial;
      Active: currently active and can be used/currently turned off;
      Scored: scoring allowed/scoring not allowed;
  Multiple sets of item parameters:
    Unique item parameter set tags for identifying different sets of parameters of the same item;
    Suitability of item for each job complexity level (people and task);
    Item parameters:
      Unique tag of scale measured by item;
      Item loading;
      Item threshold;
      Item uniqueness;
      Item social desirability;
  Item Enemies pairs of items which must not appear in the same forced-choice block;
Scales and Scale Properties
  Multiple scale sets that the items can map into:
    Unique scale set tag;
    For each scale:
      Unique scale tag;
      Scale name;
      Scale direction;
      Suitability for each job complexity level (people and task);
      Social desirability level/scale importance level;
    Covariance matrix of scales within this scale set;
Supporting Structures
  Item text version/parameter set uploading functionality;
  Item text version/parameter set extraction functionality;
  Change tracking functionality.

An item may come in several versions with minor edits, and the final version may be translated into multiple languages. All versions of the same item are stored under the same unique item tag so that they can be identified together quickly, whilst additional item text version tags are used to set them apart. Therefore, an item is identified by the combination of item unique tag and item text version tag. Item versions which are always used together (e.g. UKE English final version) have the same item text version tag so that they can be extracted together easily. Some items may become obsolete or may not be suitable in a particular language/culture, so there may in some cases be no associated item texts in that item text version.

An item bank can be designed to measure multiple psychological frameworks. Moreover, an item bank can be designed to measure the same psychological framework differently in different settings. For example, it might be desirable to score US and UK versions differently. In both situations, although the items are the same, different sets of parameters are required for IRT scoring. Item parameter set tags allow the appropriate set of item parameters to be extracted easily. Note that some items may not be suitable for certain situations, so their parameters in that parameter set would be empty.

In addition to information associated with items, an item bank also stores properties of different psychological frameworks, or sets of scales. Unique scale set tags are used to identify the scale set concerned, and unique scale tags are used to identify individual scales.

The interface between the item bank and other components is able to work with different form creation mechanisms (uploaded pre-assembled fixed forms/dynamic test generation) and different scoring processes (CCT scoring for fixed forms/IRT scoring for fixed or dynamic forms).

An item bank can contain hundreds or even thousands of items. To save manual effort and minimise potential human error, an automated item uploading functionality is provided.

An item bank summary report functionality is provided in some embodiments for exploring item bank properties, for example:
  Item availability report (e.g. count, mean and spread of
    IRT parameters)
    by job complexity (people and task)
    by a scale set
    by a language version
  Item usage report
    for exploring item exposure The item bank structure can be designed to work with one respondent type only (e.g. self-rating only or line manager rating only, but not both). Alternatively matching assessments involving multiple respondent types (e.g. 360 assessments) are implemented. To do so matching versions of items for different respondent types are stored and coordinated (e.g. "I keep a tidy sock drawer" and "He/She keeps a tidy sock drawer").

An item bank may also be used for other measurements and/or assessments in addition to multidimensional forced-choice assessment by the system.

Test Generator

The test generator reads configurations from the test configuration input frontend and dynamically generates tests accordingly using a test construction process. The test construction process interfaces with the item bank and generates forced-choice blocks one by one by first selecting a set of scales and then selecting items within those scales. It also interfaces with the online test delivery component or the offline test delivery component for test administration, and with the test scoring component to construct computer adaptive tests. Test forms generated are stored in the test form database. Sub-components of the test construction process include the item (or triplet) selector and the scale selector, which are described in detail above.

Assessment Designer

The Assessment Designer is the gateway to and control panel for the system. It consists of two secondary systems, a test configuration input frontend and a simulation engine. Assessment configurations are entered into the test configuration input frontend. Once all configurations are entered, the user can then run them through the simulation engine (which is in communication with the test generator and test scoring component) to verify the assessment design. If the simulation results are unsatisfactory, the user can go back to the test configuration input frontend to change the configurations. The assessment may go live when the user is satisfied with both the configurations and the simulation results.

To minimise repetition and for future reference (e.g. when setting up a similar project), each set of test configuration and subsequent simulation results are automatically saved in a configuration database. When an assessment goes live, the final assessment design stored in the configuration database is referenced from the project database.

Test Configuration Input Frontend:

for an assessment, the test configurations are entered manually and/or uploaded using a standard configuration template and/or retrieved from configuration recommendation tools. For well-researched assessment situations, it is desirable to have the functionality of recycling existing configurations (in some embodiments, this may, for example, be achieved by either using a standard configuration uploading template or by copying configurations from an existing assessment from the configuration database).

A list of possible design configuration entries includes:
  Item bank
    Item bank unique tag
    Scale set unique tag
    Item text version unique tag
    Item parameter set unique tag
    Scale selection
    Scale enemy specification
    Item selection and scoring statuses (default from item
      bank, alteration possible at project level)
    Item enemy specification (default from item bank,
      alteration possible at project level)
  Test design scenario
    Usage scenarios
      CAT, online, real responding
      CAT, online, simulated responding
      LOFT, online, real responding
      LOFT, online, simulated responding
      MPTF, online, real responding
      MPTF, online, simulated responding
      MPTF, offline, P&P responding
      Fixed form, online, real responding
      Fixed form, online, simulated responding
      Fixed form, offline, P&P responding
    Question format (for dynamic form generation only)
      Pairs
      Triplets
      Quads
  Test generation
    General conditions
      Starting theta by scale
      True theta by scale (for simulated responding only)
      Customised content plan
    Measurement targets
      Standard error target for each scale
        Maximum allowed standard error
        Ideal standard error
      Item target for each scale
        Minimum number of items
        Maximum number of items
      Target item keyed combination proportion
      Item keyed direction optimisation tolerance factor
    Constraints
      Job complexity level (by task and people)
      Test length constraints
        Minimum test length
        Maximum test length
      Non-scored items (experimental items) allowance
        Allowed or not
        Maximum number of non-scored items Scale selection constraints
   Scale recycling nearby blocks
   Scale pair recycling overall
   Scale pair recycling—nearby blocks
   Scale correlation
Item selection constraints
   Item recycling overall
   Item recycling nearby blocks
   Item pair recycling overall
   Maximum social desirability difference
   Minimum block information
ReTest recycling constraints (ReTest only)
   Recycling of scales and items in a retest session
Process Settings:
   Initial content randomization
   Information optimization index
   Scale information weighting scheme
   Scale and item constraints relaxation strategy
   CAT scoring frequency scheme (CAT only)
   Continuation pass ideal
   Final test form quality assurance scheme The need to update the test configuration input frontend can arise due to updates made to the test generator.

Additional configuration entries may be required (e.g. additional scale information weighting scheme/additional IRT information optimization index/additional constraint relaxation strategy/additional final test form quality assurance scheme/additional CAT scoring frequency scheme/additional content constraints/additional measurement targets/etc).

The test configuration input frontend may require a test designer to enter assessment design configurations, for example which scales are selected for measurement. Alternatively or in addition the user may draw on one or more configuration recommendation tool for test design to supply one or more assessment design configurations.

For example a scale recommendation tool (with plug-in functionality) may utilise information determined by a requirements characterisation or job analysis tool (such as described in international PCT patent application WO2013/045949 in the name of the applicant—in particular on pages 11 to 15—which is incorporated herein by reference in its entirety) and can provide competency (scale) selection, levelling and weighting. This can help the user determine important scales and hence can provide ease of use and a more automated workflow. For example, the scale recommendation tool may identify and output a set of 15 core competency scales which are important for a particular job. These competencies are then passed to the test configuration input frontend and the associated scales in relevant item banks are automatically selected for testing. Once the scale selection by the scale recommendation tool is in the test configuration input frontend, expert test designers can manually set realistic measurement targets, specify content constraints suitable for the setting and purpose of the assessment, and input any other configurations required by the test configuration input frontend. The scale recommendation tool may be extended to assemble other assessment configurations in addition to scale selections, potentially linking with project database and/or configuration database to make such recommendations. For example, when a selection of scale is determined, the project and configuration databases may be searched for similar designs, and the associated simulated and live responding data summarised to produce realistic measurement target and configuration setting recommendations.

Another example of a configuration recommendation tool is a tool for multiple assessment recommendation. Such a tool orchestrates the combined designing and reporting of multiple forced-choice schemes and/or other assessments in the same solution, boosting measurement parsimony, efficiency and validity. Such a tool for multiple assessment recommendation may for example analyse the validity of combined results of a number of assessments, and suggest particular favourable solutions. The tool can also provide for example score compositing weights and equations.

An assessment configuration decision flowchart (in document and/or software form) may be provided to aid assessment design.

Simulation Engine:

there are a large number of configurable points that can be adapted during assessment design input in the test configuration input frontend. To ensure that the combination of all these configurations leads to a reasonable assessment design, the simulation engine can help a designer to explore how a combination set of configurations interplay and affect the performance and/or functioning of an assessment. Using the theoretical forced-choice comparative judgement responding process as detailed in the Thurstonian IRT model, the simulation engine predicts how an assessment design is likely to function in real life for a target population (the assessment design is characterised by the set of configurations entered into the test configuration input frontend as described above). The target population is characterised by the distribution of theta scores of the selected scales for that population. To run a simulation, the simulation engine requires the following user inputs:

Assessment design as detailed in the test configuration input frontend
   A sample (e.g. 500 or more subjects) of true theta scores for response simulation The simulation engine then carries out simulations as follows:

1. Feed the assessment design through to the test generator;
2. For each subject in the sample:
   a. Generate test using the test generator just like in a live test;
   b. When responses are required, simulate responses using the true theta scores for this subject;
   c. When the test is completed, feed the generated test form and simulated responses into the test scoring component to recover theta scores;
   d. Record the results;
   e. Repeat for the next subject until the entire sample is covered
3. Collate results and create a simulation report.

The output of the simulation engine can include for example:

Recovered theta scores for the sample
   Summary of differences between true and recovered theta scores
   Recovered profile locations for the sample
   Summary of differences between true and recovered profile locations
   Scale reliabilities
   Profile similarities
   Percentage of mature/premature terminations in test construction The simulation engine may be updated to allow additional simulation result outputs. A synthetic data generation plug-in may be provided, so that the sample of true theta scores used for response generation is automatically generated based on the covariance structure of scales stored in the item bank, freeing the user from needing to generate and upload a sample manually.

The simulation engine can significantly improve assessment design, for example by shortening the time and human effort required for the design of an assessment. For example, it acts as a gatekeeper for verifying assessment designs, and can prevent unrealistic assessment designs from being pursued or reaching real candidates. Also, the simulation engine is a powerful tool for research into test construction optimization.

The simulation engine interfaces with test generator and test scoring component to run its predictions.

Figure 20A:
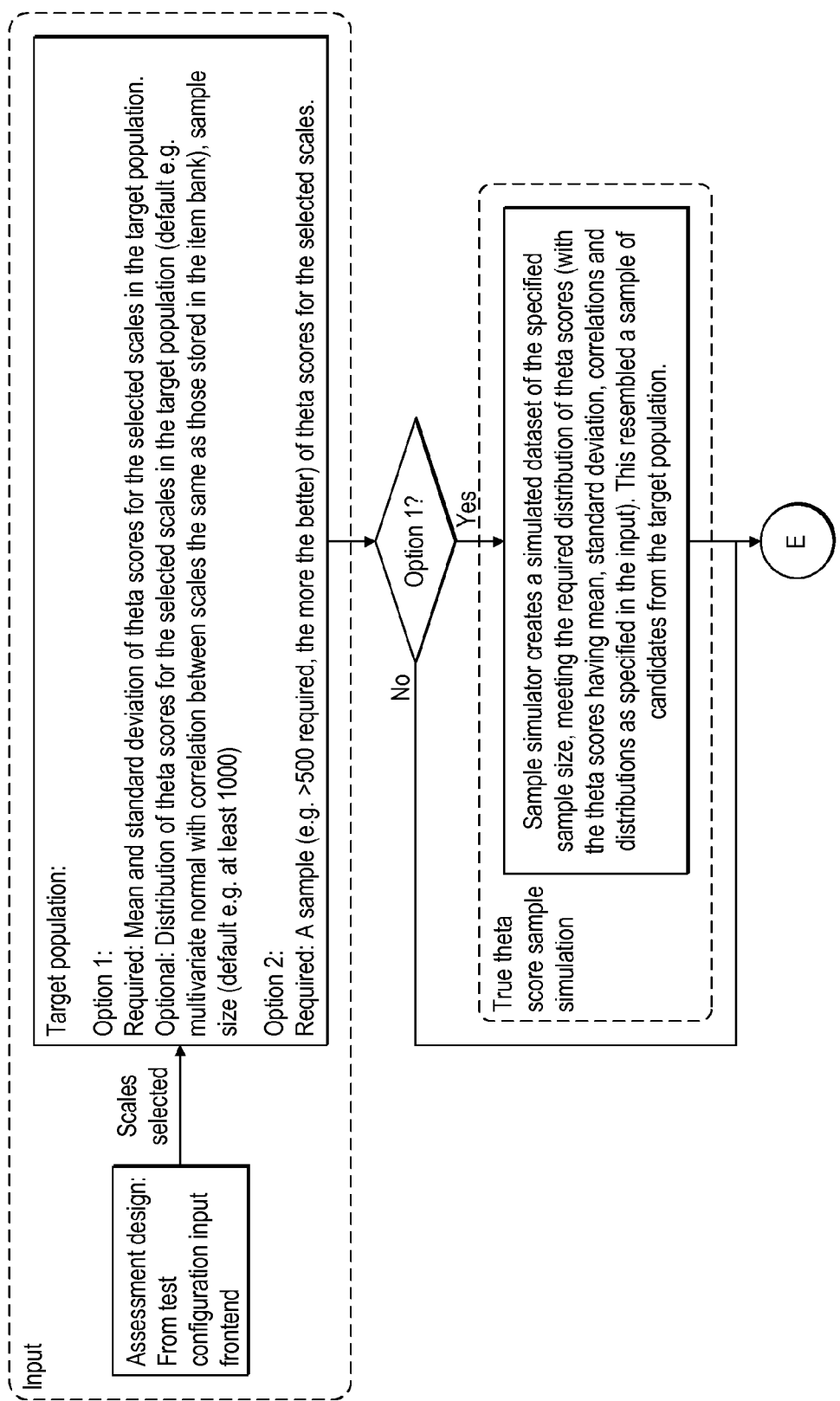
FIGS. 20 (a-c) show an example of the simulation process in the simulation engine.
Figure 20B:
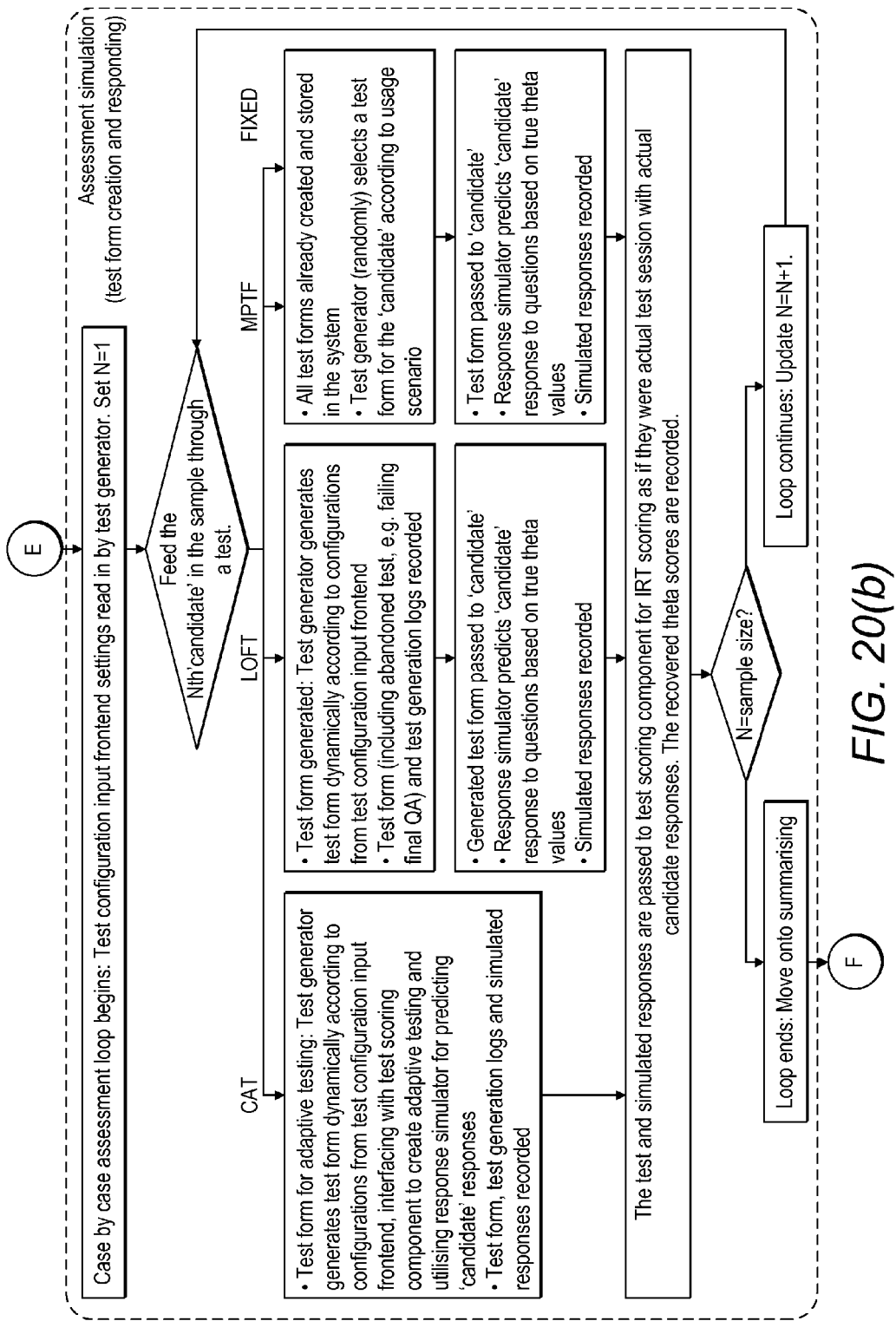
Figure 20C:
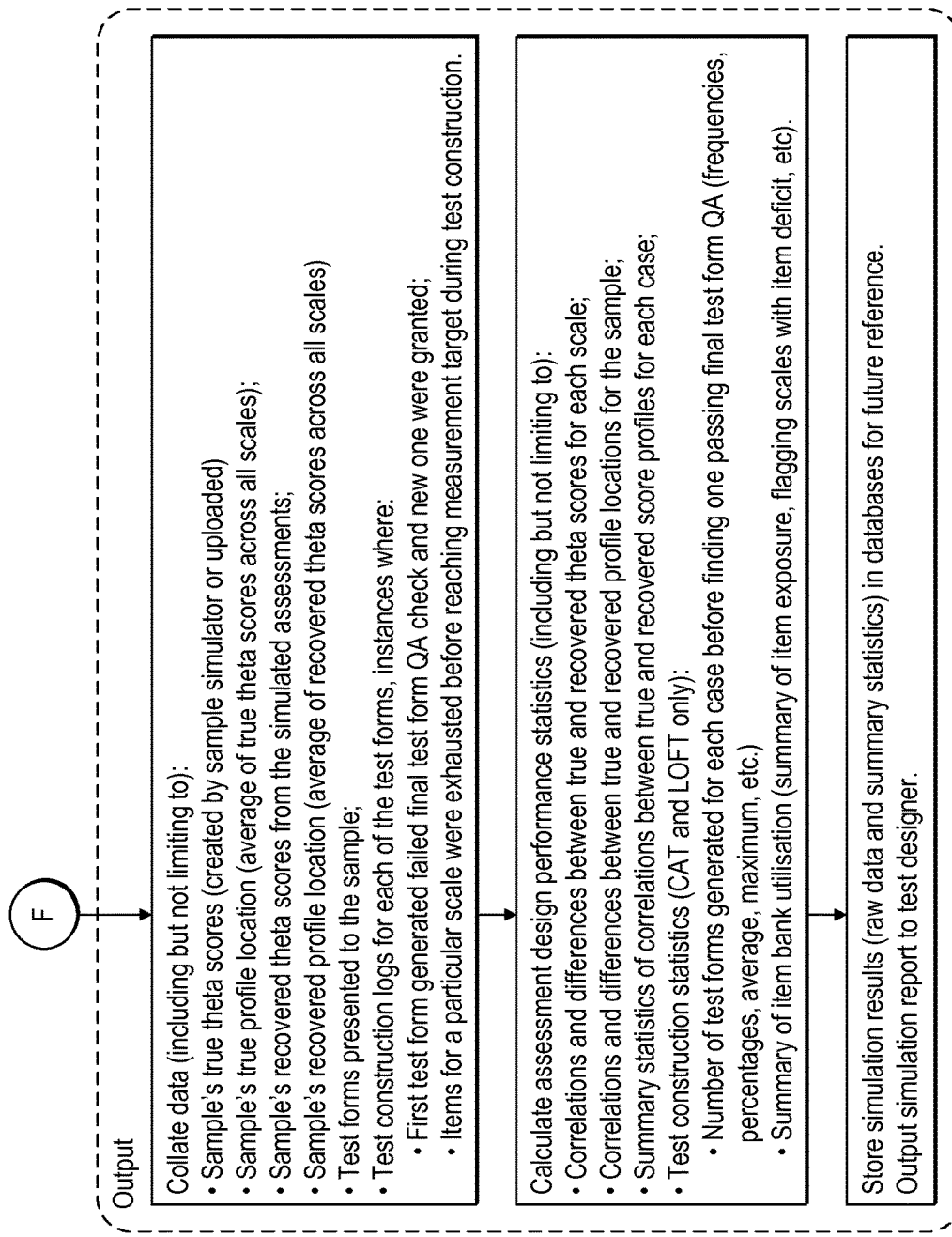

FIGS. 20 (a-c) show an example of the simulation process in the simulation engine, specifically a flowchart that outlines how the simulation engine works. The main steps are:
1. Prepare a sample of true theta scores resembling a target population (optionally using the sample simulator described below to create this sample);
2. Feed subjects in the sample one by one through the assessments:
    a. Use the test generator to create test forms if needed;
    b. Use the response simulator (described below) to simulate responses to the test forms based on the true theta scores;
    c. Use the test scoring component to score the simulated responses;
3. Collate, store and present simulation results.

When provided with the true score profile (i.e. the true theta scores on the scales selected) of a subject, the response simulator generates their likely responses to forced-choice blocks according to the Thurstonian IRT model. For example, if a triplet and a subject are passed to the response simulator with inputs as follows:

| Forced-Choice Block | | | | |
|---|---|---|---|---|
| Item (ID tag) | Scale Measured by Item (ID tag) | Item Threshold (IRT parameter from Item Bank) | Item Loading (IRT parameter from Item Bank) | Item Uniqueness Distribution (variances are IRT parameter from Item Bank) | Subject True Theta Score |
| I | A | $-\mu_i$ | $\lambda_i$ | Normal $(0, \psi_i^2)$ | $\theta_a$ |
| J | B | $-\mu_j$ | $\lambda_j$ | Normal $(0, \psi_j^2)$ | $\theta_b$ |
| K | C | $-\mu_k$ | $\lambda_k$ | Normal $(0, \psi_k^2)$ | $\theta_c$ |

The response simulator generates responses according to Thurstonian IRT as follows:
1. For item I:
    a. Simulate random variations in real life responding by sampling a value $\varepsilon_1$ from the item uniqueness distribution Normal $(0,\psi_i^2)$;
    b. Calculate the utility of the item for the subject according to Thurstonian IRT: $t_i=\mu_i+\lambda_i\theta_a+\varepsilon_i$ (for simplicity, in this example it is assumed that the IRT parameters are calibrated onto a metric so that $\theta a=\eta a$)
2. For the other items J and K, repeat the process to obtain utilities of the items for the subject:
    a. Sample $\varepsilon_j\sim$Normal $(0,\psi_j^2)$, then calculate: $t_j=\mu_j+\lambda_j\theta_b+\varepsilon_j$;
    b. Sample $\varepsilon_k\sim$Normal $(0,\psi_k^2)$, then calculate: $t_k=\mu_k+\lambda_k\theta_c+\varepsilon_k$.
3. Simulate the responses of this individual to this forced-choice block by comparing item utilities:
    a. The ranking of the values $t_i$, $t_j$ and $t_k$ provides the ranking responses required by the forced-choice block (higher values=higher preference);
    b. It is unlikely to get ties in item utilities. But if there are ties among two or more items, assign rank orders between the ties randomly.

Using this method, the response simulator can simulate responses to forced-choice blocks of any size (pairs, triplets, quads, or other—for example larger—multiplets), resembling behaviours of subjects with any true score profile. For test forms involving multiple forced-choice blocks, the responses to the blocks are independently simulated. This method can be extended for the response simulator to cover other analytical and/or measurement models, including classical test theory and/or item response theory models other than the Thurstonian IRT model.

To simulate responses to forced-choice blocks resembling the behaviours of a subject, the response simulator requires the subject's true score profile to be provided. By varying the true score profile input, the response simulator can resemble behaviours of subjects with different characteristics. By aggregating the simulated results across a sample of subjects with different true score profiles, the simulation engine can then form predictions on the functioning of assessment designs for a target population. The test designer can upload a sample of true theta scores (often acquired from empirical samples or created manually offline) to the simulation engine. Alternatively, for standard theta score distributions, the test designer can utilise the sample simulator to generate a synthetic sample of theta scores fitting the distribution required. Some examples of possible samples include:

A representative sample of the target population: The sample of theta scores is likely to be multivariate normally distributed, or having a realistic distribution reflecting that in the target population. Example usages of simulations with such a sample include:
  Predict likely performance and/or functioning of the assessment design for the target population in real life, providing statistics for:
    Fine-tuning and verifying assessment designs before they go live;
    Writing assessment instructions (e.g. test length and time required).
  Research the effects and interactions on measurement of:
    Item Banks with different compositions;
    Populations with different theta score distributions;
    Different assessment designs.
  Identify the types of items (for example, in terms of IRT parameters) that were over-exposed across multiple test forms, so that new items could be developed to reduce item exposure.

A uniform sample covering all practical theta scores: The multidimensional theta space would be sliced into equallysized grids, and a sample of size 100 (for example) would be drawn from each grid, so the whole multidimensional theta space is covered evenly. Example usages of simulations with such a sample include:

Research the effects and interactions on measurement of:
  Item Banks with different compositions;
  Different locations in the multidimensional theta space;
  Different assessment designs.
Identify the type of true theta score profiles (i.e. locations in the multidimensional theta space) that an Item Bank fails to measure accurately irrespective of assessment design, so that new items could be developed to fill the gaps.

A repeated sample of the same true score profile: The same true score profile repeated over and over again, to resemble the same subject taking the assessment multiple times. Example usages include gauging the robustness of test generation and the stability of score recovery for a subject with a particular true score profile.

In an example, the test designer provides estimates for the means and standard deviations of theta scores for the target population. The sample simulator can then extract the scale correlation matrix from the item bank and simulate a multivariate normally distributed sample of true score profiles, which satisfies both the covariance structure and the required means and standard deviations. The simulation method used by the sample simulator depends on the multivariate distribution of the required sample. Standard mathematical methods widely published in the field can be adopted for this purpose. For example, a standard method to simulate multivariate normally distributed data is detailed here http://web.as.uky.edu/statistics/users/viele/sta601s03/multnorm.odf (the content of which is herein incorporated by reference).

Regarding simulation results, the simulation engine can be programmed to produce a vast range of data and statistics on the functioning of an assessment design on a target population. For example, the test designer may be interested in the following types of statistics:

Predicted measurement accuracy, including (but not limiting to):
  Correlations and differences between true and recovered theta scores for each scale;
  Correlations and differences between true and recovered profile locations for the sample;
  Summary statistics of correlations between true and recovered score profiles for each subject;
Predicted measurement efficiency, including (but not limiting to):
  Frequency and distribution of generated test lengths for the sample;
  Frequency and distribution of time required to sit the assessment;
Predicted test generation stability (CAT and LOFT only), including (but not limiting to):
  and distribution of the number of test forms generated before hitting one passing the Final Test Form QA Scheme;
  Frequency and distribution of time required to generate a test form;
  Frequency and type of constraint relaxations required during test construction;
  Proportion of mature and premature test terminations;
Predicted Item Bank utilisation (CAT and LOFT only), including (but not limiting to):
  Item exposure;
  Item deficit.

As discussed with reference to the response simulator, the simulation engine in general can be adapted to work with assessment systems other than Thurstonian IRT systems. For example:

By linking the simulation engine to a test scoring system adopting the classical test theory (historical scoring method for forced-choice blocks), test designers can examine the effect on measurement accuracy and efficiency of using a different scoring model. This may be convenient for assessments where Thurstonian IRT scoring is not available due to administrative limitations (e.g. in paper and pencil MPTF or FIXED usage scenarios).

By linking the simulation engine to an alternative test generation system adopting the Thurstonian IRT, test designers can examine the efficiency of this alternative test generation system against the test generator described here. This is useful for example when a different alternative test construction method is implemented.

By linking the simulation engine to a test generation and scoring system using a different IRT model for forced-choice responding (e.g. Ideal Point IRT, an alternative to the Thurstonian IRT), and updating the response simulator to handle response behaviours accordingly, assessment functioning under the alternative IRT model can be modelled.

By linking the simulation engine to a test generation and scoring system for rating scale question formats (using either classical test theory or Item Response Theory as the measurement model), and updating the response simulator to handle response behaviours accordingly, rating scale assessment functioning can be predicted.

Configuration Database

When the simulation engine is called and/or when an assessment goes live, test configurations and simulation results pass on from the assessment designer to be automatically stored in the configuration database. The configuration database provides an ever growing library of assessment design decisions and associated measurement predictions. Over time, this database, together with actual assessment data subsequently collected, can provide data for:

Creating assessment design recommendations
  using configurations from a few similar projects in the database
  using design recommendation functionality based on analysing and summarising configuration decisions in all existing projects
  Providing data to a configuration recommendation tool to produce design recommendations
Flagging areas of weak measurement to improve and/or areas of high usage to expand, and adjust content pool accordingly
  by scales
  by locations in the theta space The database is likely to include, but is not limited to, the following fields:

Unique configuration ID (for referencing the configuration from Project Database/Test Form Database/Candidate Database, and for assessment delivery in the Test Generator)
All inputs to the assessment designer
All simulation outputs from the simulation engine
Date and time the configuration was created and last modified
Unique ID of the user who created the configuration Unique project and assessment IDs that the configuration was created for
Final status of the configuration (i.e. beta/five)

As the body of assessment data increases, the level of customisation of assessments can increase.

Project Database

When an assessment goes live, the final assessment design stored in the configuration database is flagged as 'live' and the unique configuration ID is also logged into the project database. Moreover, during test delivery, the unique project and assessment IDs are logged into the candidate database. This is so that there is a good record of linkages between projects, assessments in projects, design of these assessments, and candidates taking these assessments.

The following fields are needed:
Unique project ID
For each assessment within a project
  Unique assessment ID
  Unique configuration ID
All the other fields that are already stored in our current project databases, including other necessary project-specific information (for example project name, client name, industry sector, etc.)
Additional fields may be stored in the project database.

Test Form Database

Test forms created by the test generator are saved in the test form database. This happens in a number of situations:
1. When a fixed form is entered by the user. In FIXED usage scenarios where one single fixed form is used for all candidates, the test form is uploaded by the user into the test form database directly. This way, manually uploaded and automatically generated instruments are stored under the same database structure.
2. When dynamic test forms are generated during simulations: In CAT/LOFT/MPTF simulation scenarios, beta test forms generated are stored in the test form database. This way, a growing library of simulation data is available for further research into dynamic form generation. It is also possible to save computational power by reusing the forms generated during simulations (such as simulated MPTF forms generated with the final test configurations) in real tests where the test configurations are the same.
3. When dynamic test forms are generated prior to test sessions: In MPTF testing scenarios, test forms are generated prior to test sessions and stored in the test form database. These test forms can then be picked up by the online test delivery component for computerised testing or by the offline test delivery component for paper and pencil administration.
4. When dynamic test forms are generated during test sessions: In CAT/LOFT testing scenarios, test forms are generated during live test sessions and stored in the test form database. This way, records of all on-the-fly test forms are stored and the form generated for each candidate can be tracked.

The following fields are included in the test form database:
Unique test form ID
Unique project ID
Unique assessment ID
Unique configuration ID
The test form
  Items (Unique item tag, unique item bank tag, unique item text version tags, unique item parameter set tags)
  The order items appear in the test form
  How items form forced-choice blocks Test form status flags
  Manually uploaded/dynamically generated
  CAT/LOFT/MPTF/FIXED scenario
  Beta (from simulations/instrument trials)/live (for real candidates)
  Used/unused
Test generation log (for dynamically generated tests only)
Unique candidate ID (for used LOFT and CAT tests only)

Typically unique project, assessment, configuration and test form. IDs are all required because there can be multiple assessments under each project, multiple configurations (e.g. several beta configurations and one live configuration) for the same assessment, and multiple test forms generated from the same configuration. For standard fixed instruments used in more than one projects these ID variable fields are empty or set to a suitable standard value.

CAT and LOFT forms generated in live test sessions are typically used for only one candidate. For these test forms, the unique candidate IDs may be stored in the test form database too. This is especially relevant for CAT as the test forms are tailored to individual candidates.

Apart from the variables listed above, additional fields may be included in the test form database.

Online Test Delivery Component

The online test delivery component is the system that administers online assessments. It streams the test to candidates via the internet and streams back responses to servers for scoring and reporting.

The following features are included (additional features can be added):
  The ability to administer CAT/LOFT/MPTF/FIXED forms;
    Interfacing with various components, such as assessment systems, at various times as shown in the usage scenario flowcharts
    Displaying forced-choice blocks, ideally allowing forced-choice blocks of any size coupled with any kind of full or partial ranking (with the heading of the choices customisable). For example:
      Pairs, select most (or 'best' or other customised labels)
      Triplets, select most (or 'best' or other customised labels)
      Triplets, select most and least (or 'best'/'worst' or other customised labels)
      Quads, select most and least (or 'best'/'worst' or other customised labels)
      Quads, complete ranking (with customised labels)
    Shuffling the item order within a forced-choice block before displaying and/or responding, so that scales do not always appear in the same order
    Displaying multiple forced-choice blocks on the same screen
    Capturing and recording ranking responses from forced-choice blocks (and make sure the match between items and responses is not affected by the shuffling of items before displaying the block)
  System and connection stability and speed, especially for CAT and LOFT scenarios;

Given the range of possible assessment settings, some automation may be built into the candidate instruction pages before delivery of forced-choice blocks (e.g. automated update of test length/test time according to assessment design, automated example question).

In the event of unexpected test disruption or termination (e.g. internet connection broken), the online test delivery component can allow the test session to be resumed where it was interrupted.

Offline Test Delivery Component

The offline test delivery component is the system that streamlines the administration of assessments offline, for example when online administration is not a feasible option. It publishes assessments into paper and pencil formats, and captures the responses back into the system for scoring and reporting. The offline test delivery component is an optional component, for example only online test administration may be required.

To streamline offline assessment, the following features are desirable:
  Pre-assessment test-form publisher
    Extract test forms from the Test Form Database
    Publish offline administration package for each test form
      Unique test form ID
      The test form
      Responding sheet (with test form or separate)
      Any other response capturing tools (TBD)
  Post-assessment response capturer
    Scan in unique test form ID automatically
    Scan in responses from responding sheet automatically
    Pass test form and responses onto Test scoring component Test Scoring Component The test scoring component takes responses from the online test delivery component, the offline test delivery component or the simulation engine and produces theta scores based on IRT calibrations from the relevant item bank. The results are then stored in the candidate database or the configuration database in the case of simulations.

Response Reader:

the response reader is the input channel of the test scoring component. Input can come from different sources, for example:
  From the online test delivery component (linking to the test generator)
  From the offline test delivery component
  From the simulation engine
  Through a data input/upload functionality (this functionality can for example also be built as part of offline test delivery component)

The built-in data input/upload functionality provides a channel for feeding in data collected through other channels (e.g. SurveyMonkey®) into the test scoring component for scoring. In some embodiments, an input-output system functioning check can be conducted easily and independently from other system components.

Typically, the following data are picked up by the response reader:
  The test form
    Items (unique item tag, unique item bank tag, unique item parameter set tags)
    The order items appear in the test form
    How items form forced-choice blocks
  Candidate responses to test form The response reader interfaces with the relevant item bank to obtain the right set of IRT parameters to use for subsequent scoring.

The response reader may be updated in response to changes in the online test delivery component, the offline test delivery component, the simulation engine and/or the structure of item banks. In the case of ReTest usage scenarios, data from multiple test sessions are available and the test designer can configure the response reader to obtain responses from previous test sessions for joint IRT scoring.

Forced-Choice Pair Converter:

data captured by the response reader is passed onto the forced-choice pair converter. The forced-choice pair converter takes response data of forced-choice blocks of any size and format, and converts them to pairwise comparison format, for example:

| Forced-Choice Block | Converted Pairwise Comparisons |
|---|---|
| A B | AB |
| A B C | AB, AC, BC |
| A B C D | AB, AC, AD, BC, BD, CD |
| A B C D E | AB, AC, AD, AE, BC, BD, BE, CD, CE, DE |

This conversion of forced-choice block responses into pairwise comparisons (the format required for Thurstonian IRT scoring) is in this example not part of the IRT scoring process (detailed below). This can provide the advantage that test forms using different forced-choice block designs can all use the same IRT scoring process once the responses are converted to pairs.

IRT Scoring Process:

Pairwise comparison responses from the forced-choice pair converter are passed to the IRT scoring process. Theta scores and associated standard errors are calculated. The mathematical methods of the IRT Scoring Process are described in more detail in the academic papers cited in this document.

The IRT scoring process outputs theta scores, IRT information and standard errors. These results can be passed back to the test generator for CAT testing, or recorded in the candidate database (or the configuration database in the case of simulations) if the test has finished.

IRT Consistency Ratio Calculator:

when the final round of IRT scoring is completed and the final theta scores are determined, the IRT consistency ratio calculator is called and the consistency ratio is calculated using suitable consistency metrics. The consistency ratio is recorded in the candidate database (or the configuration database in the case of simulations).

Further sub-components may be included, for example for formula-based calculation of additional statistics.

Candidate Database

Candidate-level assessment data from test generator, the online test delivery component, the offline test delivery component and the test scoring component are stored in the candidate database. These data are then accessed for a range of purposes:
  Reporting
    Stand-along reporting at assessment level
    Composite scoring and reporting at solution level
  Maintenance and research
    Norm creation
    Item bank maintenance (IRT parameter drift, item exposure, etc)
    Localisation studies (construct equivalence, item DIF, etc)
    Validation studies
    Other research studies
  For example the following fields are included:
  Unique candidate ID
  Candidate status flag Real/simulated (alternatively, the simulated candidates are stored in the configuration database alongside simulation results)

For each test taken by the candidate
  Unique project ID (to link up to the project database)
  Unique assessment ID (to link up to the project database)
  Unique configuration ID (to link up to the configuration database)
  Unique test form ID (to link up to the test form database)
  CAT/LOFT/MPTF/FIXED
  Online responding/paper and pencil responding
  Test date
  Test start and end time
  Candidate responses to test form
  Test results
    Theta scores for each scale
    IRT information for each scale
    SE for each scale
    Consistency ratio of responses Additional fields may also be provided in the candidate database.

Score Compositing and Norming Component

The theta scores recovered from the assessments may not be easily interpretable. To enhance the usefulness of the system, the data may optionally be processed for reporting. In this case, before feeding data into a report, one or more transformations are possible, for example:

Theta scores from one assessment are composited and/or normed against a relevant population (e.g. to produce Sten scores and/or percentile scores);

Theta scores from several assessments in the same solution are composited to produce a composite score, which can optionally be normed against a relevant population;

Theta scores from one or several assessments are composited with scores, preferably using a different metric than the theta metric, from other assessments in the same solution, which can then optionally be normed against a relevant population;

Theta scores from one or several assessments are normed independently against a relevant population, and reported in parallel in a solution;

These theta score transformations are carried out in a score compositing and norming component. The user may be able to choose how data is composited as part of the test configuration. The test configuration recommendation tools, particularly the tool for multiple assessment recommendation described above, may inform the compositing. The compositing and/or the population to norm against may also or alternatively be configured post-assessment.

Other Applications

Although the system described has particular relevance to the personality assessment of individuals, it also has potential applications further afield.

In commerce, a system such as the one described may be used to determine customer preferences for particular product features. Constructing a set of analogous scales only based on various product features rather than personality trait may allow a ranking of products to be determined for different types of customers, say according to demographic, and consequently lead to a recommendation of which product meets the majority of a customer's requirements for product features, for example price and quality.

This may be particularly advantageous for selection of products where there exists a multiplicity of options. Some retailers, particularly e-commerce ones, currently attempt to guide the customer selection process by providing a selectable category tool (such as a drop-down menu or feature check-list).

Using a system such as the one described can be advantageous for design and production of products to meet market need as well. For example, the system may help to predict that 80% of potential customers are likely to buy design A, and 60% are likely to buy design B, and hence design A should be produced. Or in another example, 80% of potential customers are likely to buy design A and the remaining 20% are likely to buy design B, and hence 80% of the production should be design A and 20% design B.

In the following, a simple example of use of a system such as the one described for car design and production to meet market need is described.

The following 3 scales are considered: importance of speed, importance of look, importance of safety. A possible underlying covariance structure for these scales is that speed is negatively correlated with safety, and look is not related to speed or safety.

A possible triplet measuring the three scales is:
  I like to have good acceleration power (speed)
  I consider the colour when selecting a car (look)
  Airbag and seat-belt designs should meet the highest industry standard (safety)

By collecting responses from such triplets across a sample population of car buyers, the distribution of the buyer population in terms of these scales is produced.

Further, if buy/non-buy information is available for this population (for example from existing car sales/non-sales where speed/safety/look scores for the cars are known), then this information can be linked to the three scales to characterise how the three scales drive the buy/non-buy decision.

Now suppose two new designs A and B with known speed/look/safety scores are given, and only one of them can be selected for production. Then with the population distribution recovered from the sample population response data, the proportion of the population that will buy/not buy each design can be predicted. If for example design A passes the buying threshold for 80% of the buyers and design B only for 60% of the buyers, then design A is preferred.

Now suppose instead, two new designs C and D with known speed/look/safety scores are given, and both of them will be produced, but it is unknown how many units of each can be sold. The distribution of the buyer population proved information such as that 70% of the population prefers design C, 20% prefers design D, and the remaining 10% would buy neither. These proportions provide information regarding:
  how many cars of each design to produce to maximise sale/production ratios;
  which design to promote to which sub-population.

The above consideration are applied to new designs, but can equally be applied to other situations. For example in the case of a planned expansion of sales of an existing product into a new market, recovering the underlying buyer population distribution can provide valuable information for marketing and promotion decisions.

Further, the use of a forced-choice questionnaire in accordance with a system based on the one herein described may allow for a different way to narrow the choice to a suitable product.

In such embodiments, the system described may be said to act as an advanced customised searching and/or recommendation tool, enhanced according to one or more determined traits of the user. This could require the user participating in a preliminary forced-choice questionnaire. Alternatively, previous decisions made by the same—or possibly other users—could be factored in, particularly where a choice has been made from a limited selection (movies being screened at a particular cinema, for example).

A previous selection or purchasing decision may potentially be considered as a forced-choice response, with the selection expressing an underlying preference and non-selection a rejection of the presented alternatives. Potentially, by constructing forced-choice questions around the selections an underlying preference may be determined from the choices made. This could even be determined from say browsing history.

For the system to work in such a way requires constructing a suitable underlying model or construct space and determining of suitable triplets or other multiplets of items. Generally, scales may directly represent product groups. For example, a set of scales for movie viewing or book purchasing may be according to genre or category e.g. action, comedy, romance, series, modern, classic etc.

Other examples of where aspects of the system described may potentially be used include:
- the recommendation of television programmes according to likely preferences determined from previous viewing selections
- enhanced targeting of offers and/or loyalty rewards based on determined traits.
- the design of health questionnaires to determine underlying health issues from forced-choice responses
- use in fraud detection and risk assessment It will be understood that the invention has been described above purely by way of example, and modifications of detail can be made within the scope of the invention.

Each feature disclosed in the description, and (where appropriate) the claims and drawings may be provided independently or in any appropriate combination.

Reference numerals appearing in any claims are by way of illustration only and shall have no limiting effect on the scope of the claims.

The invention claimed is:

1. One or more devices for constructing a test for assessing psychological traits of a subject by means of a forced-choice assessment test, the one or more devices comprising:
   an assessment server, adapted to interact with the subject to be tested over a computer network;
   wherein the assessment server comprises one or more computers and one or more computer-readable media storing instructions that are executable by the one or more computers, wherein the one or more computers and one or more computer-readable media implement:
      a test construction engine for constructing a test, the test comprising a plurality of item blocks, wherein each item block comprises a plurality of items, each item relating to a psychological trait, and at least two of the items in an item block relating to different psychological traits, to which the subject is required to respond by at least partially ranking items from the item block, comprising:
         an interface that provides access to a database, the database adapted to store information pertaining to a plurality of scales, each scale being related to a psychological trait of the subject to be assessed, and a plurality of items, each item being associated with at least one scale and representing a stimulus to which the subject may respond;
      a test generator module adapted to generate a plurality of item blocks from items obtained from the database;
      a test configurator module for receiving a request for an item block; and
      a selector adapted to select, from among multiple item blocks, an item block to include in the test, the selector adapted to select the item block in dependence on the request and an information optimization index, wherein the selector is adapted to determine the information optimization index for each item block from a potential information gain from the subject being required to respond to the item block;
   a test administrator module for applying the test to the subject via a user terminal for displaying the test to the subject and receiving a response from the subject; and
   a scoring engine for scoring the subject response to each item block of the test and assessing a psychological trait of the subject based on the subject item block response score; and
   wherein the item block response score of the subject for a first item block is used to determine a second item block.

2. The one or more devices of claim 1, in which the information optimization index is determined from one or more of:
   i) maximising total information;
   ii) maximising capped total information;
   iii) minimising total squared information deficiency;
   iv) maximising weighted total information;
   v) maximising product information;
   vi) maximising capped product information.

3. The one or more devices of claim 1, in which the selector is adapted to rank the plurality of item blocks in dependence on the information optimization index, and to discard from consideration those item blocks for which the information optimization index is below a threshold.

4. The one or more devices of claim 1, in which the selector is adapted to rescale and/or relax determination of the information optimization index in the event that no item block that satisfies one or more criteria can be determined.

5. The one or more devices of claim 1, in which the selector is adapted to randomly select an item block.

6. The one or more devices of claim 1, in which the selector is adapted to filter the plurality of item blocks in order to remove undesirable item blocks in dependence on one or more of:
   i) whether constituent items of the item block have been used previously;
   ii) a last time the item was used;
   iii) whether constituent pairs of items have been used previously;
   iv) social desirability range/maxima;
   v) total information/minima;
   vi) a number of times an item can be picked in a test;
   vii) a minimum number of intermediate blocks between two blocks containing the same item;
   viii) recycling constraints placed on a second test session to avoid repetition of content from a first test session;
   ix) items which should not be paired in a test session; and
   x) whether non-scored items are allowed, and if so how many are allowed per test form.

7. The one or more devices of claim 1, in which the selector is adapted to construct the item blocks from which the item block is to be selected from items obtained from the database.

8. The one or more devices of claim 1, in which the selector is adapted to check for item suitability in dependence on one or more of:
   i) a number of times a scale can be picked in a test;
   ii) a minimum number of intermediate blocks between two blocks containing the same scale;
   iii) a number of times a scale pair can be selected in a test;
   iv) a minimum number of intermediate blocks between two blocks containing the same scale pairs;
   v) constraints placed on a second test session to avoid repetition of content from a first test session;
   vi) scales which should not be paired under any circumstances in the test session; and
   vii) a maximum absolute scale correlation allowed in a forced-choice block.

9. The one or more devices of claim 1, in which the selector is adapted to select items in dependence on a correlation between tolerances or limits of scales.

10. The one or more devices of claim 1, in which the selector is adapted to select item blocks in dependence upon item keyed direction combinations corresponding to the item blocks.

11. The one or more devices of claim 10, in which the selector is adapted to:
   select a desired item keyed direction combination from a plurality of item keyed direction combinations; and
   select an item block with the desired item keyed direction combination.

12. The one or more devices of claim 10, in which the selector is adapted to select a desired item keyed direction combination from a plurality of item keyed direction combinations according to a plurality of selection probabilities, each of the selection probabilities being associated with a respective one of the plurality of item keyed direction combinations.

13. The one or more devices of claim 10, in which the selector is adapted to modify a selection probability for an item block in response to selection of the item block, the selection probability corresponding to the item keyed direction combination of the selected item block.

14. The one or more devices of claim 1, in which the selector is adapted to rank the scales.

15. The one or more devices of claim 14, in which the selector is adapted to determine an information deficiency and to rank the scales according to the determined information deficiency.

16. The one or more devices of claim 14, in which the selector is adapted to generate a plurality of scale combinations in dependence on the scale ranking.

17. The one or more devices of claim 16, in which the selector is adapted to generate an item block for a most highly-ranked scale combination or for a plurality of ranked scale combinations in order of ranking.

18. The one or more devices of claim 1, wherein the test constructed by the test construction engine is a psychometric assessment test comprising a forced-choice assessment that requires the subject to indicate, for each item block in a series of item blocks, a full or partial ranking of the plurality of items in the item block in which the ranking indicates relative preferences of the subject with respect to the plurality of items in the item block, the series of item blocks being adapted to measure motivation, engagement, interests, or values of the subject; and
   wherein the selector is configured to dynamically select, during presentation of the test, at least some of the item blocks in the series of item blocks based on item block scores for previous item blocks in the series of item blocks, wherein item blocks in the series of item blocks are provided over the network at different times during the test for presentation at the user terminal.

19. A method of constructing and conducting a test for assessing psychological traits of a subject by means of a forced-choice assessment test, comprising:
   interacting, by one or more computers, with the subject to be tested over a computer network;
   constructing, by the one or more computers, a test, the test comprising a plurality of item blocks, wherein each item block comprises a plurality of items, each item relating to a psychological trait, and at least two of the items in an item block relating to different psychological traits, to which the subject is required to respond by at least partially ranking items from the item block, comprising:
      accessing, by the one or more computers, a database, the database adapted to store information pertaining to a plurality of scales, each scale being related to a psychological trait of the subject to be assessed, and a plurality of items, each item being associated with at least one scale and representing a stimulus to which the subject may respond;
      generating, by the one or more computers, a plurality of item blocks from items obtained from the database;
      receiving, by the one or more computers, a request for an item block;
      determining, by the one or more computers, an information optimization index for each of multiple item blocks from a potential information gain from the subject being required to respond to the item block; and
      selecting, by the one or more computers and from among multiple item blocks, an item block to include in the test, the item block being selected in dependence on the request and on the determined information optimization index for the item block;
   applying, by the one or more computers, the test to the subject by displaying the test to the subject and receiving a response from the subject;
   scoring, by the one or more computers, the subject response to each item block of the test;
   assessing, by the one or more computers, a psychological trait of the subject based on the subject item block response score; and
   determining, by the one or more computers, a second item block using the using the item block response score of the subject for a first item block.

* * * * *